United States Patent
Shuttleworth et al.

(10) Patent No.: US 8,614,193 B2
(45) Date of Patent: Dec. 24, 2013

(54) DEPSIPEPTIDES AND THEIR THERAPEUTIC USE

(75) Inventors: Stephen Joseph Shuttleworth, Hampshire (GB); Franck Alexandre Silva, Hampshire (GB); Cyrille Davy Tomassi, Hampshire (GB); Alexander Richard Liam Cecil, Hampshire (GB); Thomas James Hill, Hampshire (GB)

(73) Assignee: Karus Therapeutics Limited, Hampshire (GB)

( * ) Notice: Subject to any disclaimer, the term of this patent is extended or adjusted under 35 U.S.C. 154(b) by 238 days.

(21) Appl. No.: 12/991,491

(22) PCT Filed: May 22, 2009

(86) PCT No.: PCT/GB2009/050554
§ 371 (c)(1),
(2), (4) Date: Jan. 8, 2011

(87) PCT Pub. No.: WO2009/141658
PCT Pub. Date: Nov. 26, 2009

(65) Prior Publication Data
US 2011/0112090 A1 May 12, 2011

Related U.S. Application Data

(60) Provisional application No. 61/174,092, filed on Apr. 30, 2009.

(30) Foreign Application Priority Data

May 22, 2008 (GB) .................................. 0809324.7
May 22, 2008 (GB) .................................. 0809328.8

(51) Int. Cl.
*A61K 38/12* (2006.01)
*A61K 31/542* (2006.01)
*C07K 11/00* (2006.01)
*C07K 11/02* (2006.01)
*C07K 7/54* (2006.01)

(52) U.S. Cl.
USPC ........... 514/21.1; 514/1.1; 514/2.9; 514/19.4; 514/19.5; 530/317; 530/323

(58) Field of Classification Search
None
See application file for complete search history.

(56) References Cited

U.S. PATENT DOCUMENTS 8,247,372 B2 * 8/2012 Packham et al. ............... 514/2.9

FOREIGN PATENT DOCUMENTS

| EP | 1 547 617 | 6/2005 |
| WO | WO 2006/129105 | 12/2006 |

OTHER PUBLICATIONS

Definition of moiety from http://dictionary.refernce.com/browse/moiety, pp. 1-3. Accessed Aug. 26, 2010.*
Doi et al., "A total synthesis of spiruchostatin A", *Tetrahedron Letters*, Feb. 2006, vol. 47, No. 7, pp. 1177-1180.
Koch et al., "Synthesis of conformationally restricted cyclic pentadepsipeptides via direct amide cyclization", *Tetrahedron*, Mar. 2001, vol. 57, No. 12, pp. 2311-2326.

(Continued)

*Primary Examiner* — Julie Ha
(74) *Attorney, Agent, or Firm* — Saliwanchik, Lloyd & Eisenschenk

(57) ABSTRACT

The subject application pertains to a compound of structure IX or X:

Structure IX

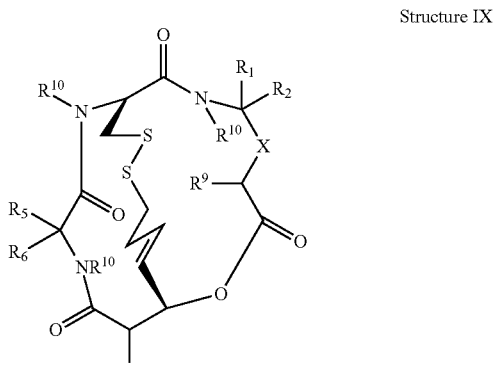

Structure X
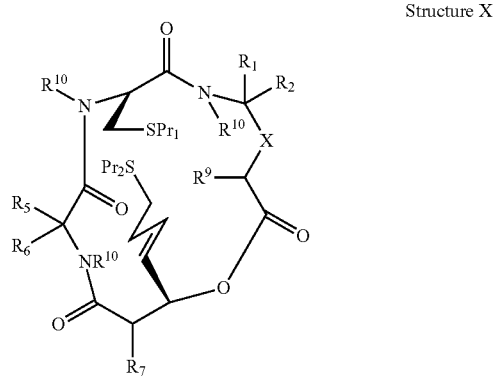

or a pharmaceutically acceptable salt thereof,
wherein:
X is $-C(=O)N(R_{10})-$ or $-CH(OPr_3)-$;
$R_7$, $R_9$ and $R_{10}$ are the same or different and represent hydrogen or an amino acid side chain moiety from either a natural or an unnatural amino acid;
$Pr_1$ and $Pr_2$ are the same or different and represent hydrogen or a thiol protecting group;
$Pr_3$ is hydrogen or an alcohol protecting group;
$R_1$, $R_2$, $R_5$ and $R_6$ are the same or different and represent hydrogen or an amino acid side chain moiety from either a natural or an unnatural amino acid, or $R_1$ and $R_2$ and/or $R_5$ and $R_6$, taken together with the carbon atom to which they are attached, form a spirocyclic moiety,
with the proviso that:
each of $R_1$ and $R_2$ is not hydrogen, or
each of $R_5$ and $R_6$ is not hydrogen.

15 Claims, No Drawings

(56) References Cited

OTHER PUBLICATIONS

Masuoka et al., "Spiruchostatins A and B, novel gene expression-enhancing substances produced by *Pseudomonas* sp.", *Tetrahedron Letters*, Jan. 2001, vol. 42, No. 1, pp. 41-44.

Yurek-George et al., "The first biologically active synthetic analogues of FK228, the depsipeptide histone deacetylase inhibitor", *Journal of Medicinal Chemistry*, Nov. 2007, vol. 50, No. 23, pp. 5720-5726.

Yurek-George et al., "Total synthesis of spiruchostatin A, a potent histone deacetylase inhibitor", *Journal of the American Chemical Society*, 2004, vol. 126, No. 4, pp. 1030-1031.

\* cited by examiner

DEPSIPEPTIDES AND THEIR THERAPEUTIC USE

CROSS-REFERENCE TO RELATED APPLICATIONS

This application is a National Stage Application of International Application Number PCT/GB2009/050554, filed May 22, 2009; which claims priority to Great Britain Applications No. 0809324.7, filed May 22, 2008 and 0809328.8, filed May 22, 2008; and claims the benefit of U.S. Provisional Application 61/174,092, filed Apr. 30, 2009; all of which are incorporated herein by reference in their entirety.

FIELD OF THE INVENTION

The present invention relates to depsipeptides which act as inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds that are able to modulate HDAC have important therapeutic potential.

The natural products FK228 (Structure I) and Spiruchostatin A (Structure II) are depsipeptides that have been reported to have potential as HDAC inhibitors. The term depsipeptide describes a class of oligopeptides or polypeptides that have both ester and peptide links the chain.

FK228 is a cyclic depsipeptide containing 4 monomer units together with a cross-ring bridge. This compound, under the trade name of ROMIDEPSIN®, has been tested as a therapeutic in human trials and shown that it has valuable effects on a number of diseases.

Spiruchostatin A is a cyclic depsipeptide that is structurally related to FK228: it is a cyclic depsipeptide containing a tri-peptide, a statine unit and a cross-ring bridge.

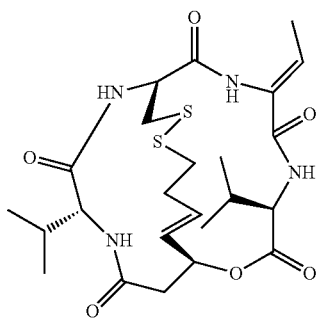

Structure I

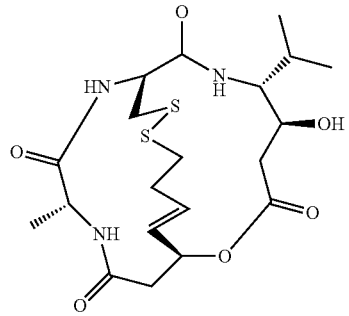

Structure II

However, because both FK228 and Spiruchostatin A are natural products, they are not amenable to optimization for use as a therapeutic agent.

Analogues of Spiruchostatin A are disclosed in PCT/GB2007/050709. They may have improved HDAC inhibitory properties with respect to Spiruchostatin A or FK228 or other drug-like properties that make them more useful as medicines. These compounds have the general structures shown in Structures III and IV wherein $R_1$, $R_5$, $R_7$ and $R_9$ are the same or different and represent hydrogen or an amino acid side chain moiety from either a natural or an unnatural amino acid, $R_2$ and $R_6$ are hydrogen, each $R_{10}$ is the same or different and represents hydrogen or $C_1$-$C_6$ alkyl, $C_2$-$C_6$ alkenyl or $C_2$-$C_6$ alkynyl, $Pr^1$ and $Pr^2$ are the same or different and represent hydrogen or a thiol protecting group and $Pr^3$ is hydrogen or an alcohol protecting group.

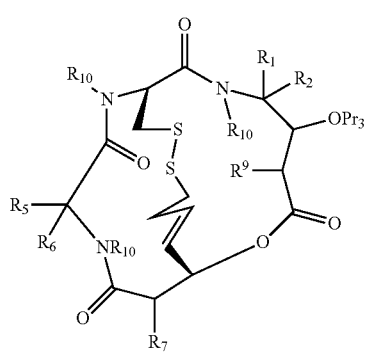

Structure III

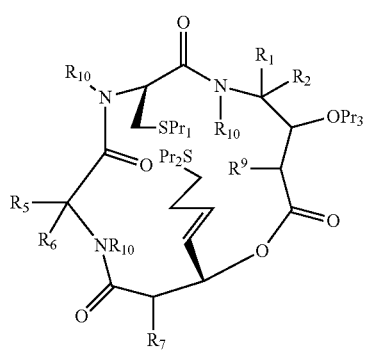

Structure IV

Analogues of FK228 are disclosed in WO2006/129105. They may have improved HDAC inhibitory properties with respect to FK228 or other drug-like properties that make them more useful as medicines. These compounds have the general structures shown in Structures V and VI wherein $R_1$, $R_5$, $R_7$ and $R_9$ are the same or different and represent hydrogen or an amino acid side chain moiety from either a natural or an unnatural amino acid, $R_2$ and $R_6$ are hydrogen, each $R_{10}$ is the same or different and represents hydrogen or $C_1$-$C_6$ alkyl, $C_2$-$C_6$ alkenyl or $C_2$-$C_6$ alkynyl, and $Pr_1$ and $Pr_2$ are the same or different and represent hydrogen or a thiol protecting group.

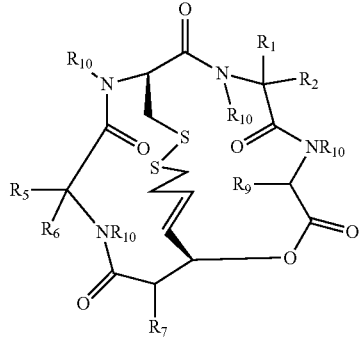

Structure V

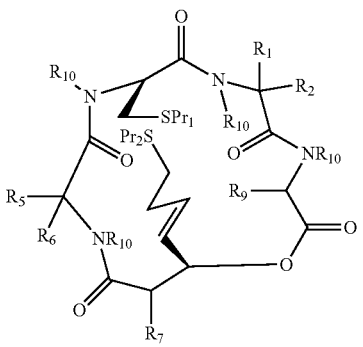

Structure VI

Analogues of FK228 and Spiruchostatin A with modifications in the disulfide containing bridge are disclosed in WO 2008/062201.

Without being constrained by theory, it is believed that Structures VII and VIII are formed inside the cell from Structures I and II respectively, by reduction of the disulfide bond, and that the 4-thio-butyl-1-ene so formed is a critical part of the mechanism of action of the compound, forming a metallophile capable of binding Zinc in the active site of HDAC.

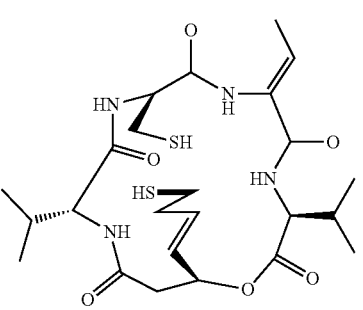

Structure VII

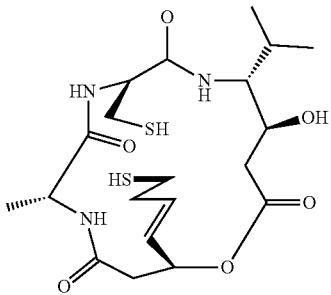

Structure VIII

This concept is supported by the observation that FR-901375, a cyclic depsipeptide HDAC inhibitor with quite a different ring structure, has the same disulfide-containing bridge across the ring as is seen in FK228 and Spiruchostatin A.

SUMMARY OF THE INVENTION

The present invention provides Structures III and IV, in which both $R_1$ and $R_2$ and/or both $R_5$ and $R_6$ are not hydrogen. In these compounds, either position 6 on the depsipeptide macrocycle (IUPAC nomenclature) and/or position 12 (IUPAC nomenclature) is bis-substituted, containing two amino acid side chain moieties (neither of which is hydrogen) or a spirocyclic moiety, The present invention also provides Structures V and VI, in which neither $R_1$ nor $R_2$ are hydrogen and/or neither $R_5$ nor $R_6$ are hydrogen. In these compounds, either position 6 on the depsipeptide macrocycle (IUPAC nomenclature) and/or position 12 (IUPAC nomenclature) is bis-substituted, containing two amino acid side chain moieties (neither of which is hydrogen) or a spirocyclic moiety, These compounds, surprisingly, are found to be effective inhibitors of HDAC enzymes, and have properties which indicate that they may have greater potential as treatments for human disease. These compounds are hereinafter designated members of the class of compounds called Bis-Substituted Depsipeptides (BSDs).

The compounds of the invention are defined by Structures IX and X:

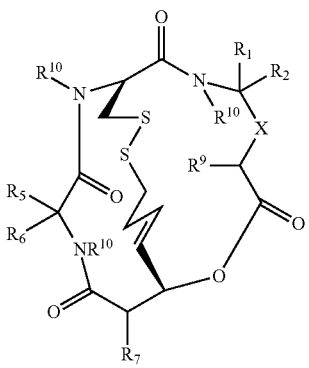

Structure IX

-continued

Structure X or a pharmaceutically acceptable salt thereof,
wherein:

X is —C(=O)N($R_{10}$)— or —CH(O$Pr_3$)—;

$R_7$, $R_9$ and $R_{10}$ are the same or different and represent hydrogen or an amino acid side chain moiety from either a natural or an unnatural amino acid;

$Pr_1$ and $Pr_2$ are the same or different and represent hydrogen or a thiol protecting group;

$Pr_3$ is hydrogen or an alcohol protecting group;

$R_1$, $R_2$, $R_5$ and $R_6$ are the same or different and represent hydrogen or an amino acid side chain moiety from either a natural or an unnatural amino acid or $R_1$ and $R_2$ and/or $R_5$ and $R_6$, taken together with the carbon atom to which they are attached, form a spirocyclic moiety, with the proviso that:
each of $R_1$ and $R_2$ is not hydrogen, or
each of $R_5$ and $R_6$ is not hydrogen.

The present invention further provides the use of the compounds of Structures IX and X defined above or a pharmaceutically acceptable salt thereof, in the manufacture of a medicament for use as an inhibitor of HDAC.

DESCRIPTION OF THE INVENTION

Synthesis of compounds of Structures IX and X is typically conducted using amino acids of which —(CO)—CR'R''—NH— forms part of the macrocycle and R' and R'' are side-chain moieties. $R_1$, $R_2$, $R_5$, and $R_6$ may be introduced in this way. $R_7$ and $R_9$ may be an amino acid side chain moiety but may not have been derived directly or indirectly from an amino acid as such.

The Structure IX or X must contain a bis-substituted carbon at either position 6 (IUPAC nomenclature) or position 12 (IUPAC nomenclature) on the depsipeptide macrocycle. In such bis-substituted compounds, either both of $R_1$ and $R_2$ are not hydrogen, or both of $R_5$ and $R_6$ are not hydrogen. Preferably, $R_1$ and $R_2$ and/or $R_5$ and $R_6$, taken together with the carbon atom to which they are attached, form a spirocyclic molecule. Preferably, the spirocyclic molecule has 3, 4, 5, 6, 7, or 8 carbon atoms. Alternatively, both $R_1$ and $R_2$ and/or $R_5$ and $R_6$ can be $C_1$-$C_6$ alkyl. As used herein, the term "amino acid side chain moiety" refers to any side chain that may be present in natural and un-natural amino acids, and therefore does not limit the nature of the group R. Examples of amino acid side chain moieties derived from unnatural amino acids, with the amino acids from which they are derived shown in brackets, are —($CH_2$)$_2$—C(O)—O—C($CH_3$)$_3$ (glutamic acid t-butyl ester), —($CH_2$)$_4$—NH—C(O)—O—C($CH_3$)$_3$ ($N_\epsilon$-(tert-butoxycarbonyl)-lysine), —($CH_2$)$_3$—NH—C(O)$NH_2$ (citrulline), —$CH_2$—$CH_2$OH (homoserine) and —($CH_2$)$_3NH_2$ (ornithine). Examples can also include $C_1$-$C_6$ alkyl, $C_2$-$C_6$ alkenyl, $C_2$-$C_6$ alkynyl, aryl, saturated and unsaturated heterocycles (functionalized & unfunctionalized).

A $C_1$-$C_6$ alkyl group or moiety can be linear or branched. Typically, it is a $C_1$-$C_4$ alkyl group or moiety, for example methyl, ethyl, n-propyl, i-propyl, n-butyl, sec-butyl and t-butyl. Preferred examples include methyl, i-propyl and t-butyl.

A $C_2$-$C_6$ alkenyl group or moiety can be linear or branched. Typically, it is a $C_2$-$C_4$ alkenyl group or moiety. It is preferred that the alkenyl radicals are mono or diunsaturated, more preferably monounsaturated. Examples include vinyl, allyl, 1-propenyl, isopropenyl, 1-butenyl, 2-butenyl and 3-butenyl.

A $C_2$-$C_6$ alkynyl group or moiety can be linear or branched. Typically, it is a $C_2$-$C_4$ alkynyl group or moiety.

Preferably the amino acid side chain moieties are those derived from natural amino acids. Examples of amino acid side chain moieties derived from natural amino acids, with the amino acids from which they are derived shown in brackets, are —H (Glycine), —$CH_3$ (Alanine), —CH($CH_3$)$_2$ (Valine), —$CH_2$CH($CH_3$)$_2$ (Leucine), —CH($CH_3$)$CH_2CH_3$ (Isoleucine), —($CH_2$)$_4NH_2$ (Lysine), —($CH_2$)$_3$NHC(=NH)$NH_2$ (Arginine), —$CH_2$-(5-1H-imidazolyl) (Histidine), —$CH_2CONH_2$ (Asparagine), —$CH_2CH_2CONH_2$ (Glutamine), —$CH_2$COOH (Aspartic acid), —$CH_2CH_2$COOH (Glutamic acid), —$CH_2$-phenyl (Phenylalanine), —$CH_2$-(4-OH-phenyl) (Tyrosine), —$CH_2$-(3-1H-indolyl) (Tryptophan), —$CH_2$SH (Cysteine), —$CH_2CH_2SCH_3$ (Methionine), —$CH_2$OH (Serine), and —CH(OH)$CH_3$ (Threonine).

Preferably each amino acid side chain is an amino acid side chain moiety present in a natural amino acid or is —($CH_2$)$_2$—C(O)—O—C($CH_3$)$_3$ (glutamic acid t-butyl ester), —($CH_2$)$_4$—NH—C(O)—O—C($CH_3$)$_3$ ($N_\epsilon$-tertbutoxycarbonyl)-lysine), —($CH_2$)$_3$—NH—C(O)$NH_2$ (citrulline), —$CH_2$—$CH_2$OH (homoserine) or —($CH_2$)$_2$—$CH_2NH_2$ (ornithine).

Preferably each amino acid side chain is an amino acid side chain moiety present in a natural amino acid or is —(C$R_{11}R_{11}$)$_x$—N$R_{11}$C(O)N$R_{11}R_{11}$, —(C$R_{11}R_{11}$)$_x$—N$R_{11}$C(O)N$R_{11}R_{13}$, —(C$R_{11}R_{11}$)$_x$—N$R_{11}$C(O)O$R_{14}$, —(C$R_{11}R_{11}$)$_x$—N$R_{11}$C(O)$R_{14}$, —(C$R_{11}R_{11}$)$_x$—N$R_{11}$C(O)$R_{13}$, —(C$R_{11}R_{11}$)$_x$—N$R_{11}$SO$_2$N$R_{11}R_{11}$, —(C$R_{11}R_{11}$)$_x$—N$R_{11}$SO$_2$N$R_{11}R_{13}$, —(C$R_{11}R_{11}$)$_x$—N$R_{11}$SO$_3R_{14}$, —(C$R_{11}R_{11}$)$_x$—N$R_{11}$SO$_2R_{14}$, —(C$R_{11}R_{11}$)$_x$—N$R_{11}$SO$_2R_{13}$, —(C$R_{11}R_{11}$)$_x$—C(O)N$R_{11}R_{11}$, —(C$R_{11}R_{11}$)$_x$—C(O)N$R_{11}R_{13}$, —(C$R_{11}R_{11}$)$_x$—CO$_2R_{11}$, —(C$R_{11}R_{11}$)$_x$—C(O)$R_{13}$, —(C$R_{11}R_{11}$)$_x$—SO$_2$N$R_{11}R_{11}$, —(C$R_{11}R_{11}$)$_x$—SO$_2$N$R_{11}R_{13}$, —(C$R_{11}R_{11}$)$_x$—SO$_2R_{13}$, —(C$R_{11}R_{11}$)$_x$—Ar. Where x is an integer between 1 and 10, where $R_{11}$ is hydrogen, $C_1$-$C_6$ alkyl, $C_3$-$C_7$ cycloalkyl, aryl, $C_2$-$C_6$ alkenyl, $C_2$-$C_6$ alkynyl, heteroaryl, where $R_{13}$ is N$R_{11-C}$(O) $R_{14}$, N$R_{11}$—SO$_2R_{14}$, where $R_{14}$ is $C_1$-$C_6$ alkyl, aryl, $C_2$-$C_6$ alkenyl, $C_2$-$C_6$ alkynyl, heteroaryl and where Ar is an aryl or a heteroaryl ring, including but not limited to thiazole, tetrazole, imidazole, oxazole, isoxazole, thiophene, pyrazole, pyridine, pyrimidine, pyrazine, pyridazine and functionalized derivatives.

Preferably one or both pairs of side-chain moieties, (wherein $R_1$ and $R_2$ form one pair and $R_5$ and $R_6$ form another pair), taken together with the carbon atom of the depsipeptide macrocycle to which they are attached, form spirocyclic moieties such that the carbon that is a part of the depsipeptide macrocycle is also part of a external cyclic moiety, the external cyclic moiety being cycloalkyl, or other cyclic group which preferably has 3 to 8 atoms, e.g. cyclopropyl.

As used herein "aryl" means a monocyclic, bicyclic or tricyclic monovalent aromatic radical, such as phenyl, biphenyl, naphthyl, anthracenyl, which can be optionally substituted with up to five substituents independently selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulphonyl, aminosulfonyl, mono $C_1$-$C_3$ alkyl aminosulfonyl and bis $C_1$-$C_3$-alkyl aminosulfonyl.

As used herein "heteroaryl" means a monocyclic, bicyclic or tricyclic monovalent aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents independently selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl) amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulphonyl, aminosulfonyl, mono $C_1$-$C_3$ alkyl aminosulfonyl and bis $C_1$-$C_3$-alkyl aminosulfonyl.

The groups $Pr_1$ and $Pr_2$ represents hydrogen or a thiol-protecting group. Said thiol-protecting group is typically:

(a) a protecting group that forms a thioether to protect a thiol group, for example a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamantyl, $C_1$-$C_6$ acyloxymethyl (for example pivaloyloxymethyl, tertiary butoxycarbonyloxymethyl);

(b) a protecting group that forms a monothio, dithio or aminothioacetal to protect a thiol group, for example $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl;

(c) a protecting group that forms a thioester to protect a thiol group, such as tertiary-butyloxycarbonyl (BOC), acetyl and its derivatives, benzoyl and its derivatives; or (d) a protecting group that forms a carbamic acid thioester to protect a thiol group, such as carbamoyl, phenylcarbamoyl, $C_1$-$C_6$ alkylcarbamoyl (for example methylcarbamoyl and ethylcarbamoyl).

Typically, $Pr_1$ and $Pr_2$ are the same or different and each represent hydrogen or a protecting group that forms a thioether, a monothio, dithio or aminothioacetal, a thioester or a carbamic acid thioester to protect a thiol group. Preferably, $Pr^1$ and $Pr^2$ are the same or different and each represent hydrogen or a protecting group selected from a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamantyl, $C_1$-$C_6$ acyloxymethyl (for example pivaloyloxymethyl, tertiary butoxycarbonyloxymethyl), $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl, tertiary-butyloxycarbonyl (BOC), acetyl and its derivatives, benzoyl and its derivatives, carbamoyl, phenylcarbamoyl and $C_1$-$C_6$ alkylcarbamoyl (for example methylcarbamoyl and ethylcarbamoyl). Most preferably, $Pr_1$ and $Pr_2$ are hydrogen.

The group $Pr_3$ represents hydrogen or a protecting group that forms an ether, an acetal or aminoacetal, an ester or a carbamic acid ester to protect a hydroxyl group. Preferably, $Pr_3$ represents hydrogen or a protecting group selected from a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamantyl, $C_1$-$C_6$ acyloxymethyl (for example pivaloyloxymethyl, tertiary butoxycarbonyloxymethyl), $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl, tertiary-butyloxycarbonyl (BOC), acetyl and its derivatives, benzoyl and its derivatives, carbamoyl, phenylcarbamoyl and $C_1$-$C_6$ alkylcarbamoyl (for example methylcarbamoyl and ethylcarbamoyl). Most preferably, $Pr_3$ is hydrogen.

Preferably, X is —$CH(OPr_3)$, and compound of the invention has one of Structures IXa and Xa:

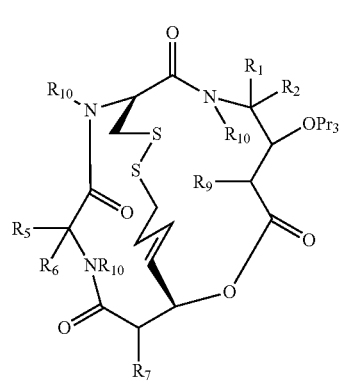

Structure IXa

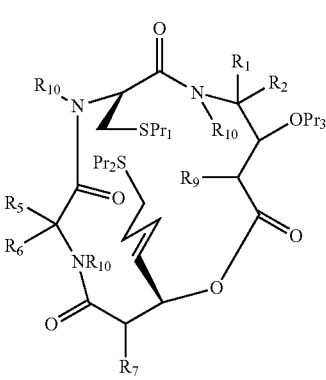

Structure Xa

Preferred embodiments include Compounds XI to XIII:
Compound XI
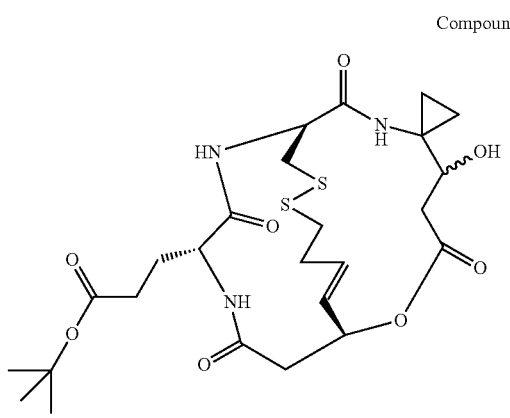
Compound XII
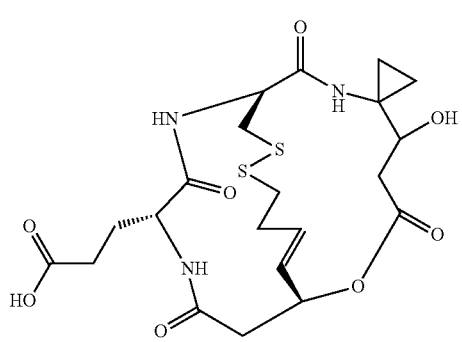
Compound XIII
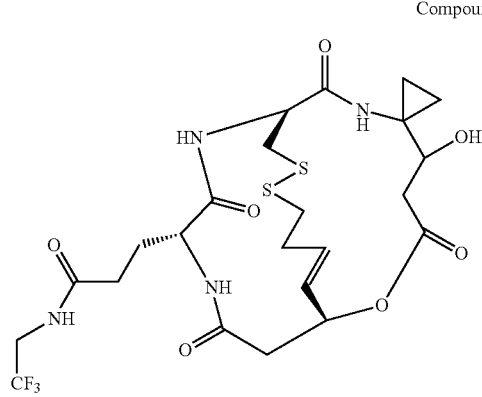
Preferably X is —C(=O)N(R$_{10}$)—, and a compound of the invention has either Structure IXb or Xb:
Structure IXb
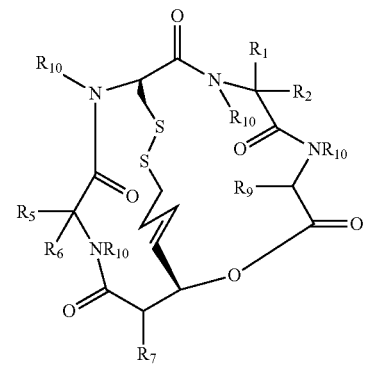
Structure Xb
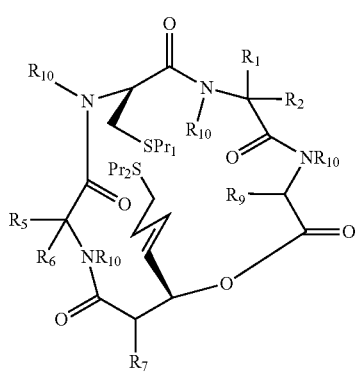
Preferred embodiments include Compounds XIV to XXXIV:
Compound XIV
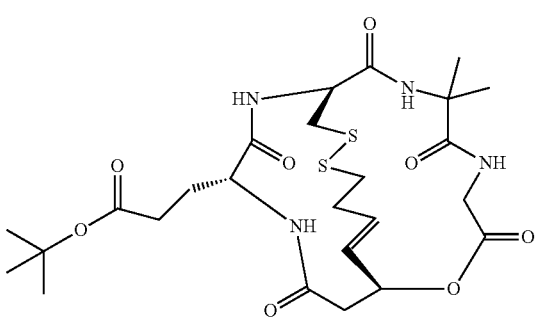
Compound XV
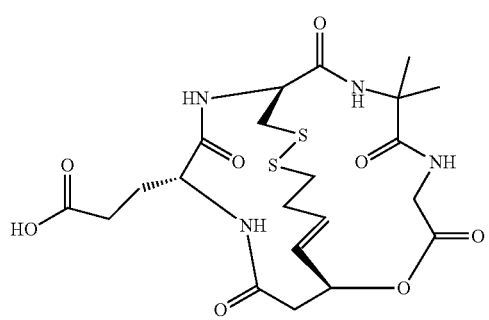

Compound XVI
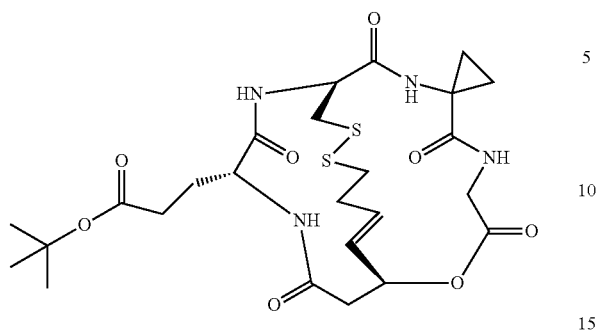
Compound XVII
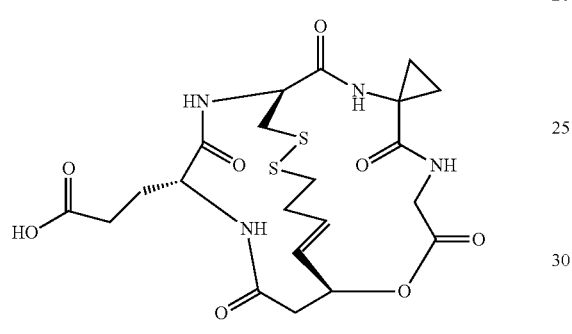
Compound XVIII
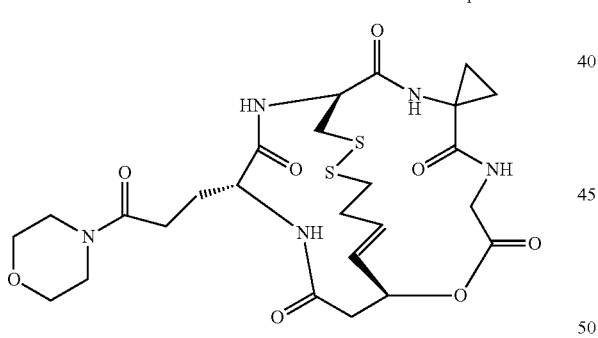
Compound XIX
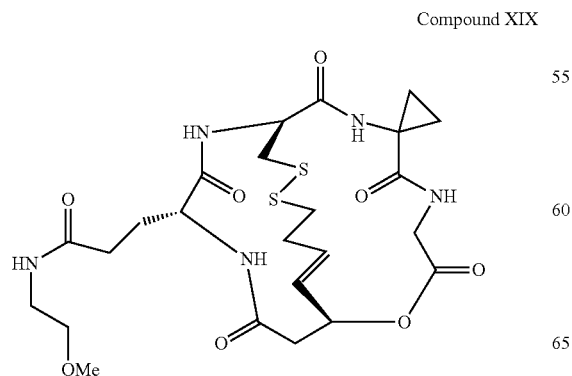
Compound XX
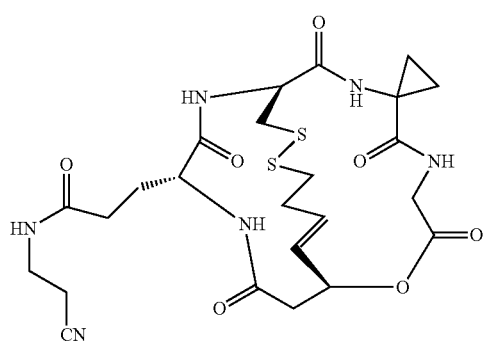
Compound XXI
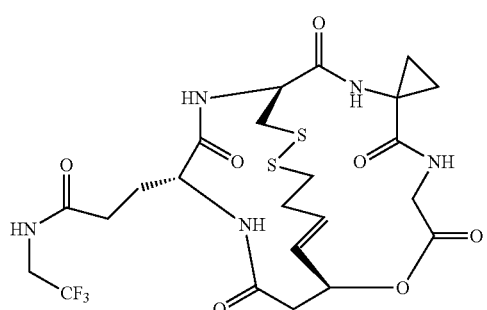
Compound XXII
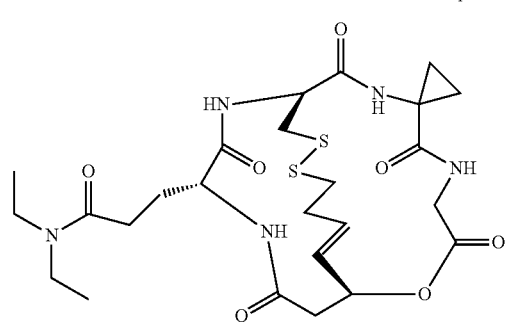
Compound XXIII
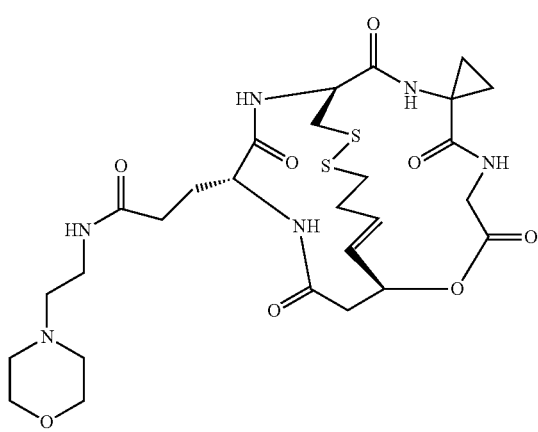

Compound XXIV
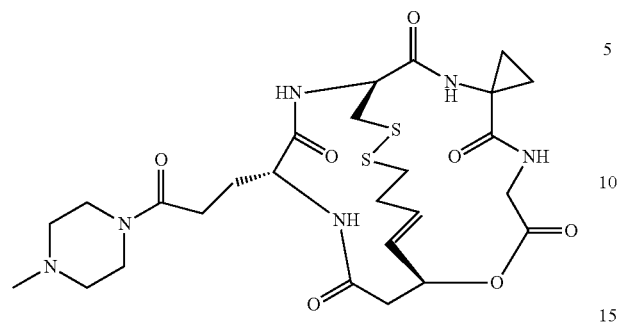
Compound XXIX
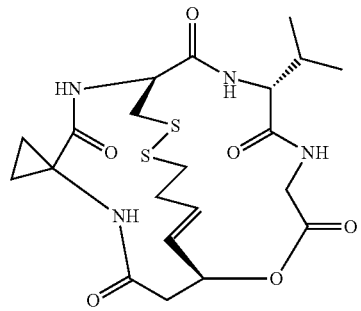
Compound XXV
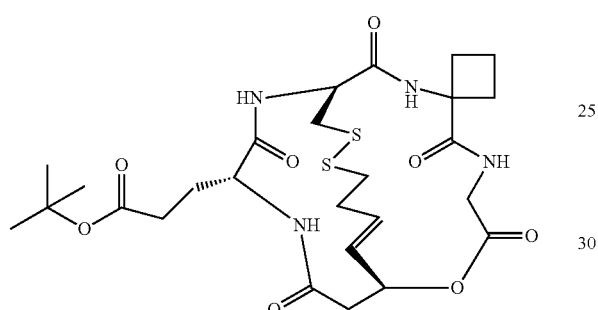
Compound XXX
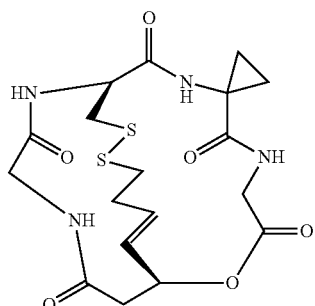
Compound XXVI
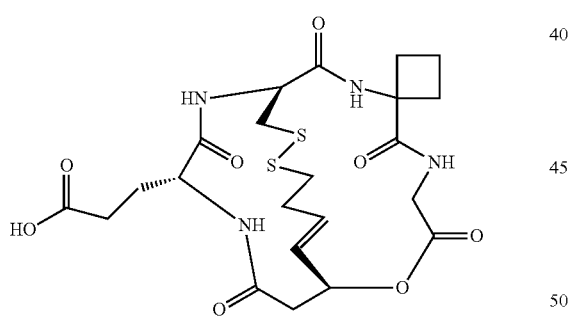
Compound XXXI
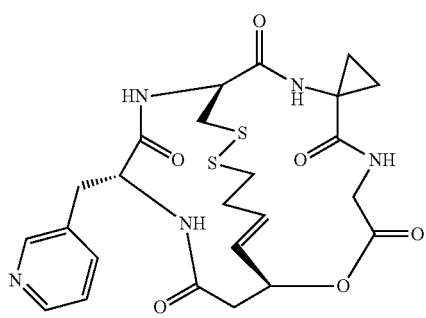
Compound XXVII
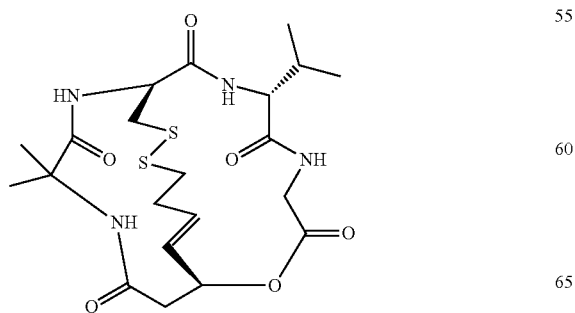
Compound XXXII
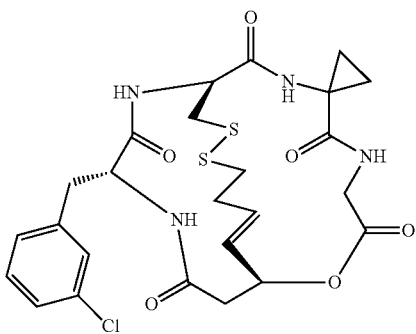

-continued

Compound XXXIII

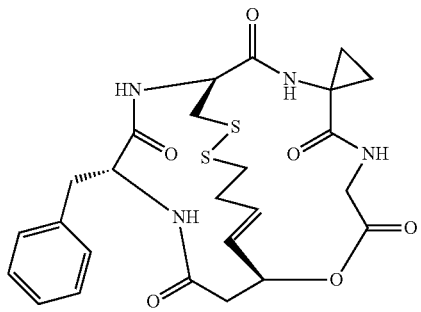

Compound XXXIV

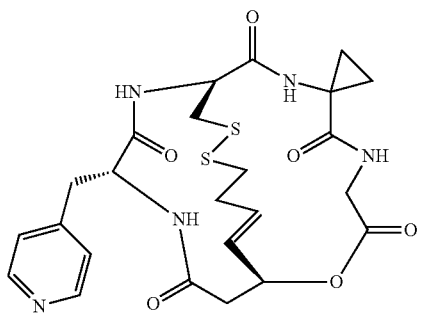

The present invention also provides a compound of formula IX or X, an isostere thereof or a pharmaceutically acceptable salt thereof and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt of a compound of Structure IX or X or an isostere thereof.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

As used herein, the term "isostere" refers to a compound resulting from the exchange of an atom or a group of atoms with another, broadly similar, atom or group of atoms. In the compounds of Structures IX or X, the moieties which contain isosteric groups are preferably —$NR_{10}$—$CHR_1$—CO—, —$NR_{10}$—$CHR_9$—CO—O— and —$NR_{10}$—CO—$CHR_5$—$NR_{10}$—CO—$CHR_7$—. Examples of such isosteres are compounds of Structures IX or X wherein the moiety —NH— has been replaced by —$CH_2$—, —O— or —S—, the moiety —CO— has been replaced by —CS— or —C(=NH)— and the moiety —O— has been replaced by —S—, —$CH_2$— or —NH—.

For the avoidance of doubt, the present invention also embraces pro-drugs which react in vivo to give a compound of the present invention or an isostere or pharmaceutically acceptable salt thereof.

The compounds of the invention wherein X is —CH($OPr_3$)— of Structure IXa and Xa can be prepared by conventional routes, for example using the following Scheme 1 wherein the functional groups are as defined above and PG represents a nitrogen protective group:

Scheme 1

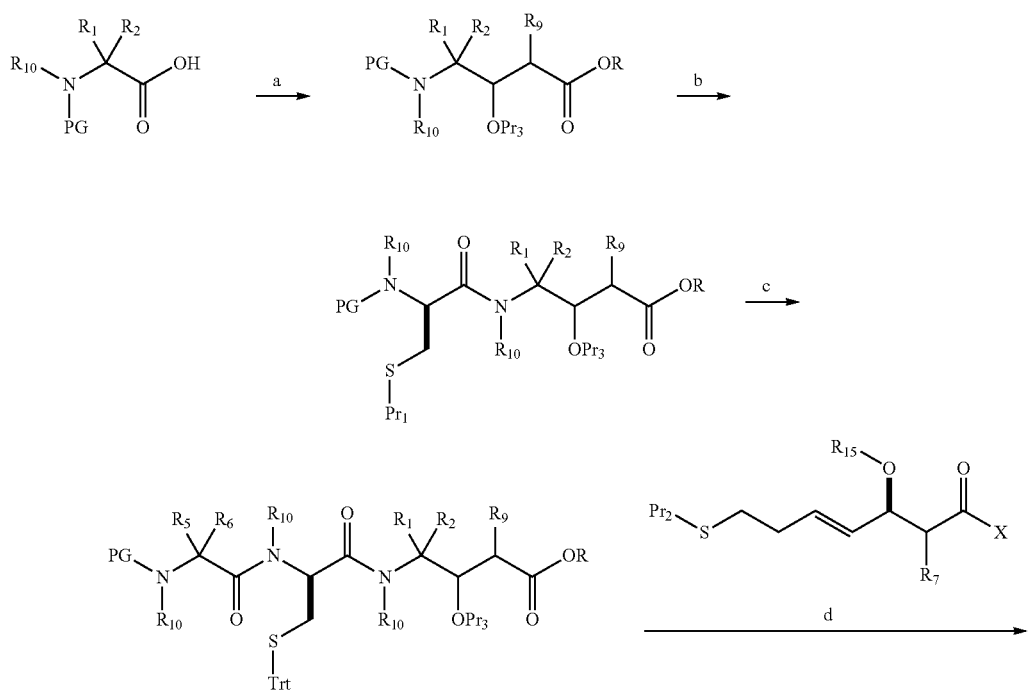

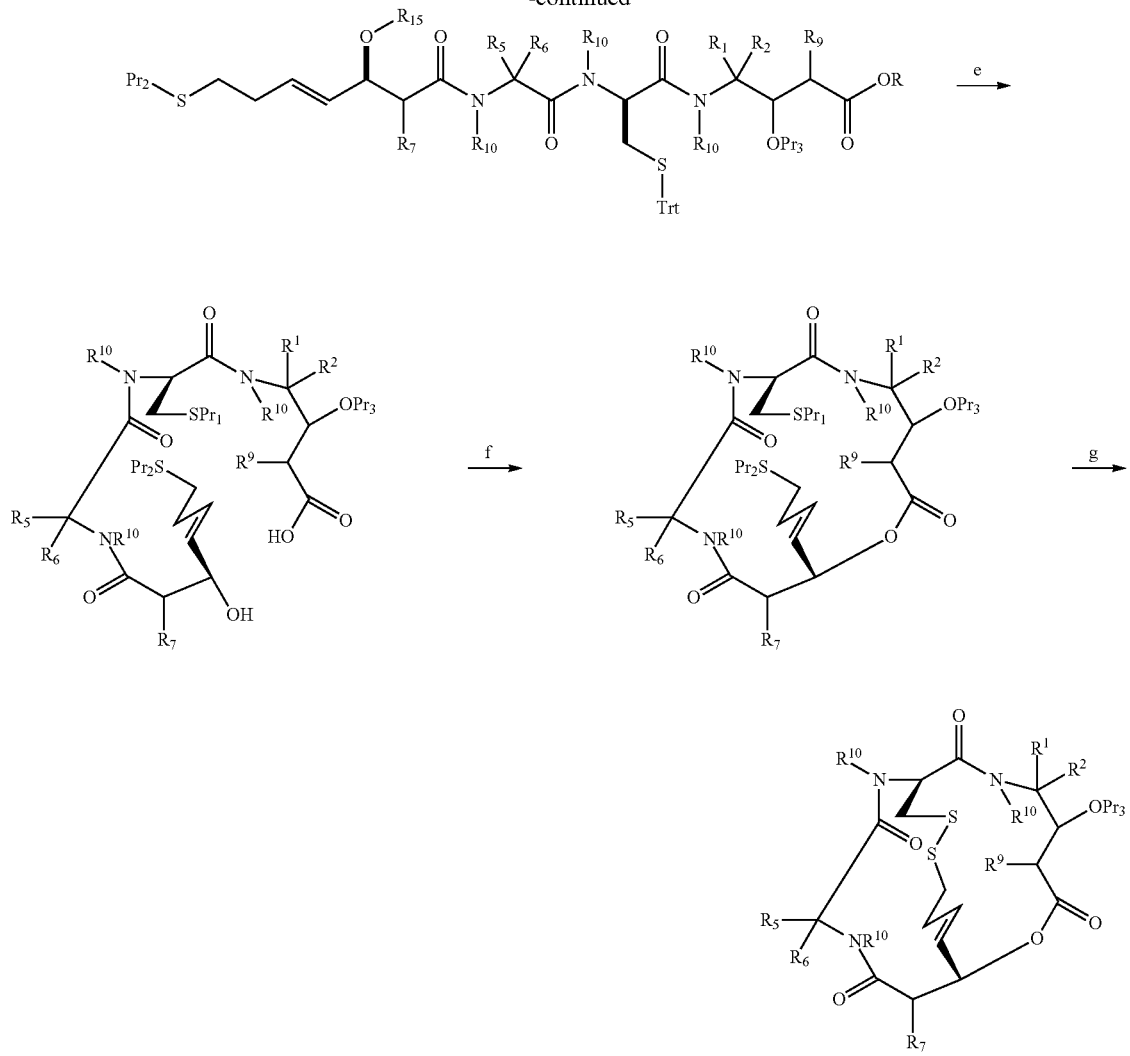

In Scheme 1 step (a), an N-protected amino acid bearing the side-chains $R_1$ and $R_2$ is condensed with an ester enolate bearing the side chain $R_9$ and the resulting intermediate 1,3-diketo-ester is then reduced to furnish a statine unit, wherein $Pr_3$ is H or a removable alcohol-protecting group. In step (b), the N-protecting group is removed, and the statine is coupled to a protected cysteine derivative to furnish a peptide isostere. In step (c), the N-protecting group is removed, and the peptide isostere is coupled with an N-protected amino acid bearing the side chains $R_5$ and $R_6$. In step (d), the N-protecting group is removed, and the resulting intermediate is coupled with a functionalised □hydroxy acid derivative wherein $R_{15}$ is a temporary blocking group which can be removed to produce a compound wherein $R_{15}$ is H, and X is a chiral auxiliary as reported in Yurek-George, A.; Habens, F.; Brimmell, M.; Packham, G.; Ganesan, A. *J. Am. Chem. Soc.* 2004, 126, 1030-1031. In step (e), the ester is hydrolysed, and cyclization is facilitated in step (f) to provide a compound of the invention wherein X is —CH(OPr$_3$)— of Structure Xa. Disulfide bond formation occurs in step (g) to provide a compound of the invention wherein X is —CH(OPr$_3$)— of Structure IXa.

The compounds of the invention wherein X is —C(=O)N(R$_{10}$)— of Structures IXb and Xb may be prepared by conventional routes, for example using the following Scheme 2 wherein the functional groups are as defined above:

Scheme 2

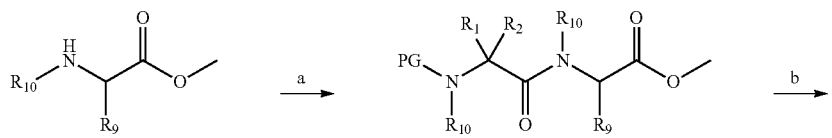

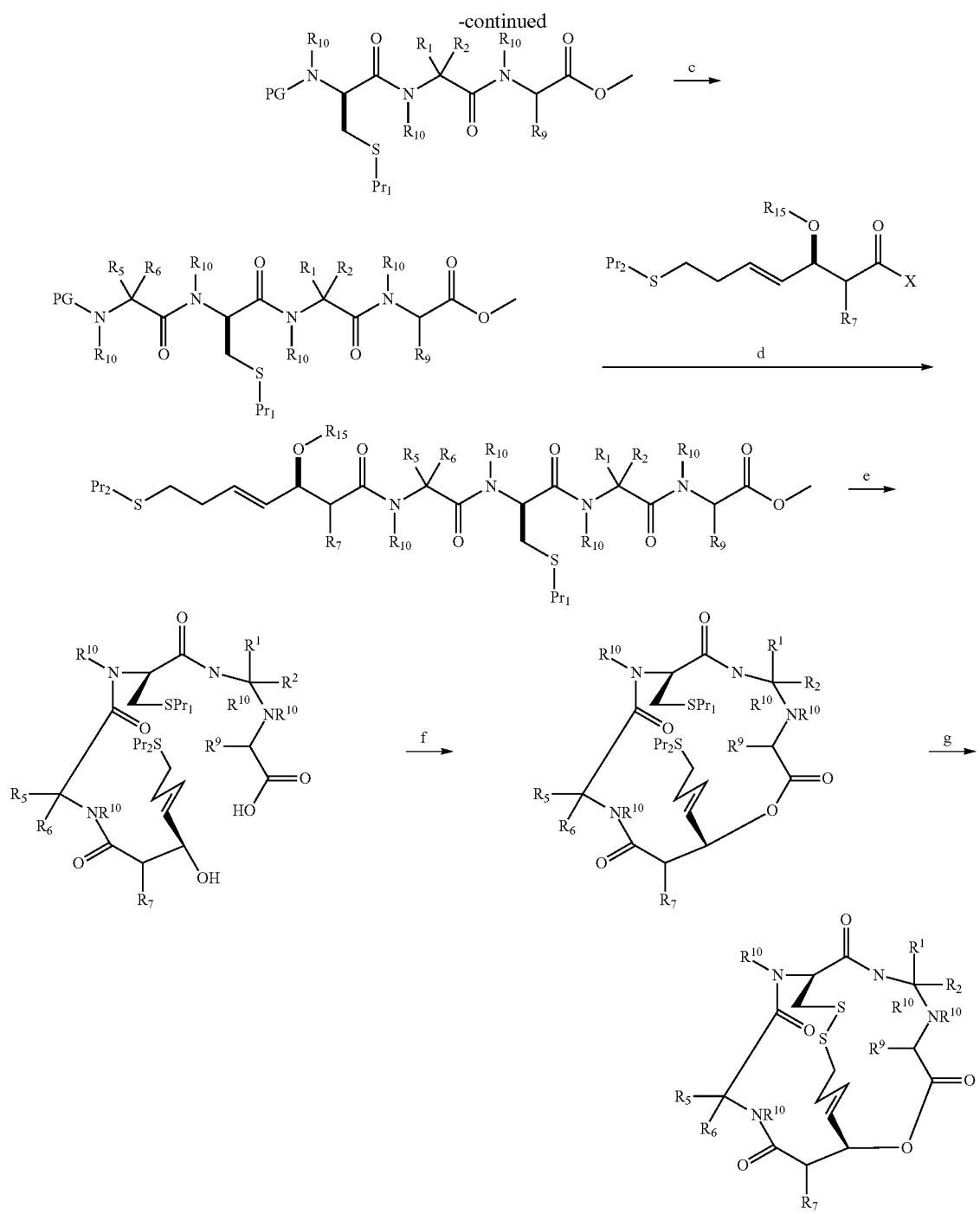

In Scheme 2 step (a), an amino acid ester bearing the side-chain $R_9$ is coupled with another, N-protected amino acid bearing the side chains $R_1$ and $R_2$ (where PG represents a conventional protecting group) to furnish the N-protected dipeptide ester. In step (b), the N-protecting group is removed, and the resulting dipeptide ester is coupled to a protected cysteine. In step (c), the N-protecting group is removed, and the resulting tripeptide is coupled with an amino acid bearing the side chains $R_5$ and $R_6$ to liberate an N-protected tetrapeptide ester. In step (d), the N-protecting group is removed and the resulting tetrapeptide ester is coupled with a functionalised beta-hydroxy acid derivative wherein $R_{15}$ is a temporary blocking group which can be removed to produce a compound wherein $R_{15}$ is H, and X is a chiral auxiliary as reported in Yurek-George, A.; Habens, F.; Brimmell, M.; Packham, G.; Ganesan, A. J. Am. Chem. Soc. 2004, 126, 1030-1031. In step (e), the ester is hydrolysed, and cyclization is facilitated in step (f) to provide a compound wherein X is —C(O)N($R_{10}$)— of the Structure Xb. Disulfide bond formation occurs in step (g) to provide a compound wherein X is —C(=O)N($R_{10}$)— of the Structure IXb.

Compounds of the invention of Structures IX and X in which $R_{10}$ is other than hydrogen can be obtained either by alkylating a corresponding compound of the invention or intermediate in which $R_{10}$ is hydrogen or by using appropriately substituted starting materials.

Compounds of Structure X may be obtained by reaction of the product of step (g) of the above Schemes 1 and 2, i.e. a compound of Structure IX, to cleave the disulfide bond. The cleavage of the disulfide bond is typically achieved using a thiol compound generally used for a reduction treatment of a protein having a disulfide bond, for example mercaptoethanol, thioglycol acid, 2-mercaptoethylamine, benzenethiol, parathiocresol and dithiothreitol. Preferably, mercaptoethanol and dithiothreitol are used. An excess thiol compound can be removed by for example dialysis or gel filtration. Alternatively, electrolysis, sodium tetrahydroborate, lithium aluminum hydride or sulfite may, for example, be used to cleave the disulfide bond.

Compounds of Structure X in which $Pr_1$ and/or $Pr_2$ is other than hydrogen may be prepared by introducing a thiol-protecting group into a corresponding compound in which $Pr_1$ and/or $Pr_2$ is/are hydrogen. In this aspect a suitable agent for introducing thiol-protecting group to be used in this reaction is appropriately determined depending on the protecting group to be introduced. Examples include chlorides of the corresponding protecting group (for example benzyl chloride, methoxybenzyl chloride, acetoxybenzyl chloride, nitrobenzyl chloride, picolyl chloride, picolyl chloride-N-oxide, anthryl methyl chloride, isobutoxymethyl chloride, phenylthiomethyl chloride) and alcohols of the corresponding protecting group (for example diphenylmethyl alcohol, adamanthyl alcohol, acetamidemethyl alcohol, benzamidomethyl alcohol), dinitrophenyl, isobutylene, dimethoxymethane, dihydropyran and t-butyl chloroformate.

As the skilled person will appreciate, when one of $R_1$, $R_5$, $R_7$, $R_9$, $R_{10}$ carries a functional group such as —OH, —SH, —NH$_2$ or —COOH, then it may be preferred for that group to be protected for one or more of the reaction steps following its introduction. In this case the group in question could be protected in a separate step after its introduction, or, it could be protected already at the time it is introduced. The skilled person will be aware of suitable protecting groups that can be used in this regard.

The compounds of the invention thus obtained may be salified by treatment with an appropriate acid or base. Racemic mixtures obtained by any of the above processes can be resolved by standard techniques, for example elution on a chiral chromatography column.

The skilled person will appreciate that various assays are suitable for testing for HDAC inhibition and may be used to measure the activity of a compound obtained from Scheme 1 compared to that of the known HDAC inhibitor SAHA. Thus, the $IC_{50}$ of a test compound against HDAC can, for example, be determined in an in vitro assay, and compared with the $IC_{50}$ of SAHA under the same assay conditions. If a test compound has an $IC_{50}$ value equal to or lower than that of SAHA it should be understood as having an HDAC inhibitory activity which is at least equal to that exhibited by SAHA.

In a preferred embodiment the present invention provides a process for selecting a compound which has an HDAC inhibitory activity which is at least equal to that exhibited by SAHA as defined above, wherein following completion of Scheme 1, the next step is a an in vitro HDAC assay. Typically, said assay comprises contacting a test compound and SAHA, at various concentrations, with diluted HeLa Nuclear Extract to determine the $IC_{50}$ of the test compound and of SAHA against HeLa Nuclear Extract. A test compound which has an $IC_{50}$ value measured against HeLa Nuclear Extract which is equal to, or lower than, the $IC_{50}$ of SAHA under the same assay conditions should be understood as having an inhibitory activity which is at least equal to that exhibited by SAHA. Typically said assay is performed using a HDAC fluorescent activity assay kit (Biomol, UK) and the test compounds are reduced prior to analysis.

In another embodiment the present invention provides a process for selecting a compound which has a human cancer cell growth inhibitory activity which is at least equal to that exhibited by SAHA, which process comprises preparing a compound of Structure IX or X via Scheme 1 as defined above followed by screening the thus obtained compound to measure its activity as a human cancer cell growth inhibitor.

The skilled person will appreciate that various assays are suitable for testing for human cancer cell growth inhibition and may be used to measure the activity of a compound obtained via Scheme 1 compared to that of SAHA. Thus, the $IC_{50}$ of a test compound against human cancer cell growth can, for example, be determined in an in vitro assay, and compared with the $IC_{50}$ of SAHA under the same assay conditions. If a test compound has an $IC_{50}$ value equal to or lower than that of SAHA it should be understood as having an inhibitory activity which is at least equal to that exhibited by SAHA. Typically in this embodiment this step comprises an in vitro assay which comprises contacting a test compound and SAHA, at various concentrations, with an MCF7 breast, HUT78 T-cell leukaemia, A2780 ovarian, PC3 or LNCAP prostate cancer cell line to determine the $IC_{50}$ of the test compound and of SAHA against the cell line. A test compound which has an $IC_{50}$ value measured against any of these cell lines which is equal to, or lower than, the $IC_{50}$ of SAHA under the same assay conditions should be understood as having an inhibitory activity at least equal to that of SAHA. Typically in this embodiment, said assay is performed using the CYQUANT™ assay system (Molecular Probes, Inc. USA).

In another preferred embodiment the present invention provides a process for selecting a compound which has an anti-inflammatory activity which is at least equal to that exhibited by SAHA, which process comprises preparing a compound of Structure IX or X via Scheme 1 as defined above followed by screening the thus obtained compound to measure its anti-inflammatory activity.

The skilled person will appreciate that various assays are suitable for assessing the anti-inflammatory activity of a compound. The anti-inflammatory activity of a test compound relative to SAHA may, for example, be determined by measuring the activity of a compound in inhibiting the production of TNFα from peripheral blood mononuclear cells (PBMCs) relative to SAHA. Thus, the ability of a test compound to inhibit the production of TNFα from PBMCs can, for example, be determined in an assay, and compared with the activity of SAHA under the same assay conditions. If a test compound has an in vitro inhibitory activity of TNFα production which is equal to or higher than that of SAHA under the same assay conditions it should be understood as having an anti-inflammatory activity which is at least equal to that exhibited by SAHA. Typically this step is performed using the QUANTIKINE® Human-α assay kit (R&D systems, Abingdon UK).

In another aspect of this embodiment, the anti-inflammatory activity of a test compound relative to SAHA may be determined by assessing the activity of a compound in inhibiting inflammation in Balb/c mice relative to SAHA. If a test compound has an in vivo inhibitory activity which is equal to or higher than that of SAHA under the same test conditions it should be understood as having an anti-inflammatory activity which is at least equal to that exhibited by SAHA. Typically, in this embodiment this step is performed by assessing the in vivo activity of a test compound and of SAHA in inhibiting inflammation in Balb/c mice induced by a chemical challenge. Typically, said chemical challenge involves the topical administration to the mice of oxalazone or acetone. In this embodiment, the compounds under investigation may be applied before or after the chemical challenge.

In another preferred embodiment the present invention provides a process for selecting a compound which has an activity in inducing a predominant G2/M phase arrest or cell death in MCF7 cells which is at least equal to that exhibited by SAHA, which process comprises preparing a compound of Structure I or X via Scheme 1 as defined above followed by screening the thus obtained compound to measure activity in inducing a predominant G2/M phase arrest or cell death in MCF7 cells relative to SAHA.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantages of inhaled medications are their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention, or a pharmaceutically acceptable salt thereof.

The compounds of the invention may also be administered by sublingual administration. The present invention therefore also provides a sub-lingual tablet comprising a compound of the invention or a pharmaceutically acceptable salt thereof.

A compound of the invention is typically formulated for administration with a pharmaceutically acceptable carrier or diluent.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention are therapeutically useful in the treatment or prevention of conditions mediated by HDAC. Accordingly, the present invention provides the use of a compound of the Structure IX or X, or a pharmaceutically acceptable salt thereof, in the manufacture of a medicament for use in the treatment or prevention of a condition materially affected by the activity of an HDAC. Also provided is a method of treating a patient suffering from or susceptible to a condition mediated by HDAC, which method comprises administering to said patient an effective amount of a compound of Structure IX or X, an isostere thereof or a pharmaceutically acceptable salt thereof.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The present invention therefore also provides the use of compounds according to Structure IX or X or an isostere or pharmaceutically acceptable salt thereof for use in the manufacture of a medicament for use in co-administration with another known inhibitor of HDAC, such as SAHA.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN 38 and DNA methylation inhibitors for example the DNA methylation inhibitors disclosed in WO 02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of a compound of Structure IX or X as defined above or an isostere thereof or a pharmaceutically acceptable salt thereof in the manufacture of a medicament for use in the alleviation of cancer by coadministration with another chemotherapeutic or antineoplastic agent.

The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein, and the use of compounds of the present invention described by Structure IX or X are included herein. It is noted that additional diseases beyond those disclosed herein may be later identified as applications of the compounds of the present invention, as the biological roles that HDAC play in various pathways becomes more fully understood.

One set of indications that HDAC inhibitors of the present invention may be used to treat are those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta.-minopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated 5 features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilms' tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of retina/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischemic heart disease, angina, arrhythmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumors, more preferably for the treatment of malignant tumors and most preferably for the treatment of CCL, breast cancer and T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes, osteoporosis, MDS, benign prostatic hyperplasia, oral leukoplakia, a genentically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genentically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S aureus, P acne, candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia, breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

A therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

EXAMPLES

Compound XIa and XIb

Diastereomers of 3-((E)-(1S,9S,20R)-5-Hydroxy-6,6-cyclopropyl-3,8,18,21-tetraoxo-2-oxa-11,12-dithia-7,19,22-triaza-bicyclo[7.7.6]docos-15-en-20-yl)-propionic acid tert-butyl ester

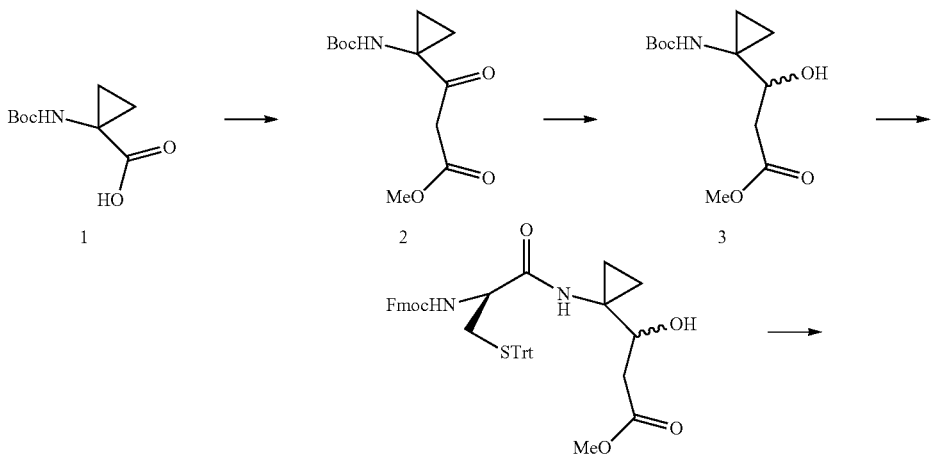

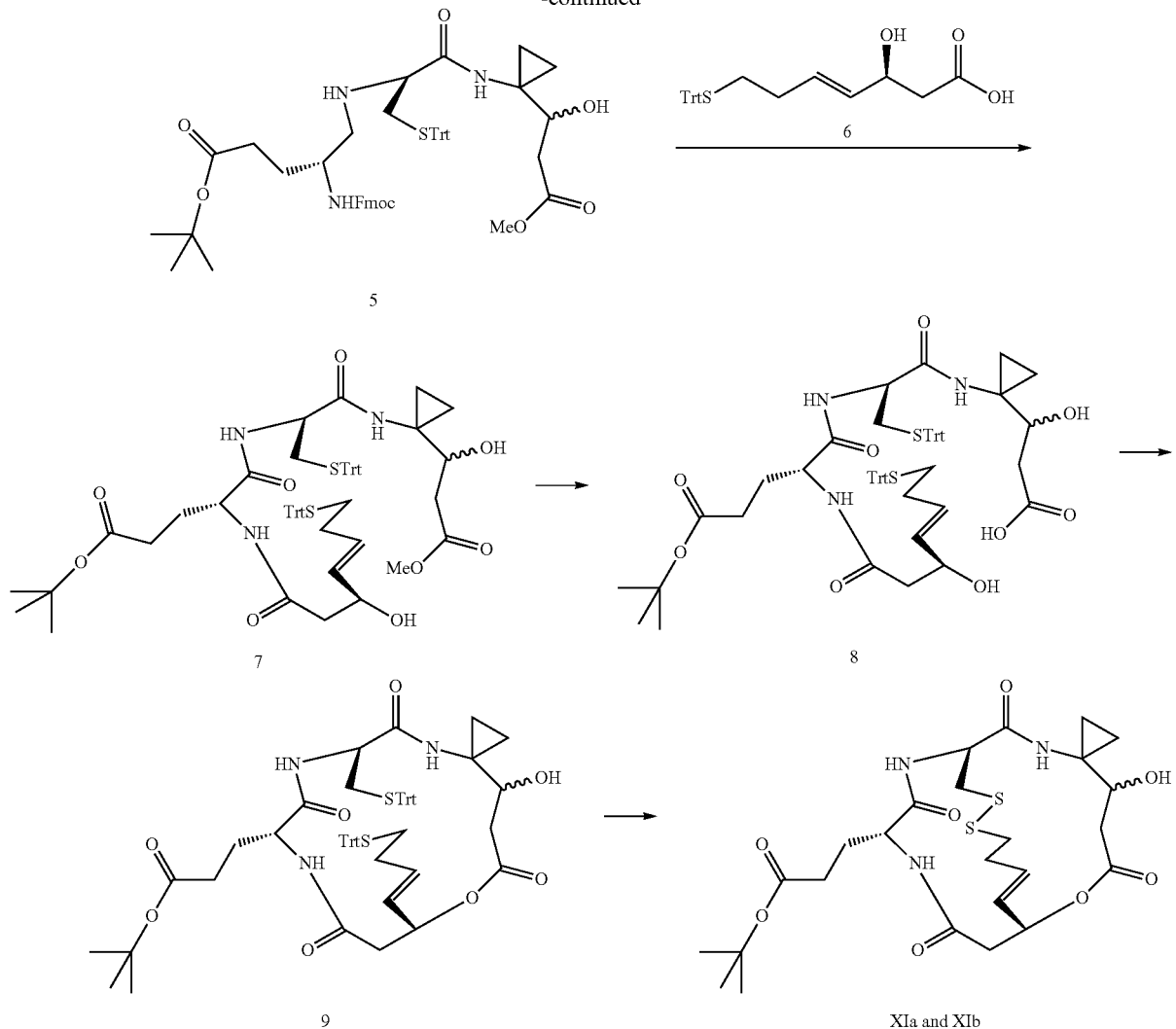

(2): 3-(1-tert-Butoxycarbonylamino-cyclopropyl)-3-oxo-propionic acid methyl ester To 1-tert-Butoxycarbonylamino-cyclopropanecarboxylic acid 1 (2.077 g, 10.3 mmol) in CH$_2$Cl$_2$ (44 mL) was added DMAP (258 mg, 2.11 mmol), pentafluorophenol (2.100 g, 11.4 mmol) and EDAC (2.369 g, 12.3 mmol) and the reaction mixture was stirred at rt for 1 h 50 min. 1M HCl (aq) (40 mL) was added, the layers were separated and, after washing with saturated NaHCO$_3$ (aq) (40 mL) and then with saturated brine (40 mL), the organic layer was dried (MgSO$_4$), concentrated in vacuo, and placed under high vacuum. To THF (12.5 mL) at −78° C. was added LDA (2.0 M, 17 mL, 34 mmol) followed by methylacetate (2.6 mL, 32.7 mmol) in dropwise fashion. The reaction was stirred for 30 min, and the intermediate ester of 1-tert-butoxycarbonylamino-cyclopropanecarboxylic acid was added in THF (35 mL), and the resulting mixture was stirred for 3 h 20 min. The mixture was quenched with 1M HCl (aq) (50 mL), the layers were separated and washed with saturated NaHCO$_3$ (aq) (50 mL) and brine (50 mL). Following extraction with EtOAc, the combined organics were dried (MgSO$_4$) and concentrated in vacuo. Purification was carried out by flash column chromatography on silica (eluant 3:7-4:6-1:1 EtOAc/Hexane) to give 2 (1.0526 g, 4.09 mmol, 40%) as a yellow oil.

$^1$H NMR (400 MHz, CDCl$_3$) δ$_H$: 5.24 (br s, 1H), 3.76 (s, 3H), 3.70 (s, 2H), 1.67-1.62 (m, 2H), 1.47 (s, 9H), 1.21 (br s, 2H). MS (ES$^+$) 279.8 (100%, [M+Na]$^+$). R$_f$ 0.40 EtOAc/Hexane (6:4).

(3): 3-(1-tert-Butoxycarbonylamino-cyclopropyl)-3-hydroxy-propionic acid methyl ester To 2 (1.053 g, 4.09 mmol) in HPLC MeOH (20 mL) at −78° C. was added portion-wise KBH$_4$ (764.3 mg, 14.2 mmol), and the resulting reaction mixture was stirred for 45 min before being warmed to −20° C., and being stirred for a further 30 min at that temperature. The mixture was then warmed to 0° C. and stirred for a further 2 h, after which the mixture was quenched with AcOH until the pH was below 7. The mixture was then concentrated in vacuo, and EtOAc (70 mL) was added followed by water (40 mL). The layers were separated and the aqueous phase was extracted with EtOAc (60 mL). The organic extracts were combined, washed with saturated brine (60 mL), dried (MgSO$_4$) and concentrated in vacuo. Purification was performed by flash column chromatography on silica (eluant 3:7-4:6-1:1 EtOAc/Hexane) to give 3 (436 mg, 1.68 mmol, 41%) as a white solid (diastereoisomers 1:1 ratio).

$^1$H NMR (400 MHz, CDCl$_3$) $\delta_H$: 5.08 (br s, 1H), 4.37 (d, J=4.27 Hz, 1H), 3.71 (s, 3H), 3.47 (m, 1H), 2.65 (dd, J=6.71, 3.33 Hz, 2H), 1.45 (s, 9H), 1.01 (m, 1H), 0.92 (m, 1H), 0.86-0.73 (m, 2H). MS (ES$^+$) 281.8 (100%, [M+Na]$^+$). R$_f$ 0.55 EtOAc/Hexane (6:4).

(4): 3-{1-[(S)-2-(9H-Fluoren-9-ylmethoxycarbonylamino)-3-tritylsulfanyl-propionylamino]-cyclopropyl}-3-hydroxy-propionic acid methyl ester To a solution of 3 (431.3 mg, 1.66 mmol) in CH$_2$Cl$_2$ (20 mL) at 0° C. under Ar(g) was added TFA (4 mL, 20% v/v) dropwise, and the reaction mixture was stirred for 2 h 35 min. The solvent was removed in vacuo below 30° C. and then placed under high vacuum for 2 h. To a solution of PyBOP (734 mg, 1.41 mmol) and Fmoc-D-Cys(STrt)-OH (825 mg, 1.41 mmol) in CH$_2$Cl$_2$ (15 mL) at 0° C. was added diisopropylethylamine (1.2 mL, 6.89 mmol) under Ar(g) and the mixture was stirred for 2 min. A solution of the crude amine of 3 in MeCN (15 mL) was then added, and the reaction was allowed to stir at 0° C. for 1 h, and at rt for 2 h, after which time the solvent was removed in vacuo. Purification by flash column chromatography on silica (eluant 4:6-4.5:5.5-5.5:4.5 EtOAc/Hexane) gave 4 (924 mg, 1.27 mmol, 90%) as a white solid, and as a mixture of diastereoisomers not resolved by $^1$H NMR $^1$H NMR (400 MHz, CDCl$_3$) $\delta_H$: 7.75 (t, J=6.78 Hz, 2H), 7.55 (d, J=6.65 Hz, 2H), 7.44-7.35 (m, 8H), 7.32-7.17 (m, 11H), 6.36 (d, J=7.65 Hz, 1H), 4.98 (m, 1H), 4.41-4.35 (m, 2H), 4.21-4.15 (m, 1H), 3.71 (m, 1H), 3.60 (s, 3H), 3.49-3.43 (m, 2H), 2.72-2.60 (m, J=13.72, 13.72, 6.90, 6.68 Hz, 1H), 2.60-2.49 (m, 3H), 1.01 (m, 1H), 0.83-0.73 (m, 3H). MS (ES$^+$) 749.5 (100%, [M+Na]$^+$). R$_f$ 0.41 EtOAc/Hexane (6:4).

(5): (R)-4-(9H-Fluoren-9-ylmethoxycarbonylamino)-4-{(S)-1-[1-(1-hydroxy-2-methoxycarbonyl-ethyl)-cyclopropylcarbamoyl]-2-tritylsulfanyl-ethylcarbamoyl}-butyric acid tert-butyl ester To 4 (908 mg, 1.28 mmol) in MeCN (10 mL) was added diethylamine (1 mL, 10% v/v), and the reaction mixture was stirred for 2 h. The mixture was then concentrated in vacuo, MeCN (3×20 mL) was added, then removed in vacuo, and the crude amine was placed under high vacuum for 2 h. Subsequently, to a solution of PyBOP (705 mg, 1.35 mmol) and Fmoc-D-Glu(O$^t$Bu)-OH (577.8 mg, 1.36 mmol) in CH$_2$Cl$_2$ (15 mL) at 0° C. was added diisopropylethylamine (0.70 mL, 4.02 mmol) under Ar(g) and the mixture was stirred for 2 min. A solution of the crude amine derivative of 4 in MeCN (15 mL) was added, and the mixture was stirred at rt for 16 h, and the solvent was then removed in vacuo. Purification by flash column chromatography on silica (eluant 4:6-6:4 EtOAc/Hexane) gave 5 (1.099 g, 1.20 mmol, 94%) as a white solid: R$_f$ 0.54 EtOAc/Hexane (6:4), and as a mixture of diastereoisomers not resolved by $^1$H NMR.

$^1$H NMR (400 MHz, CDCl$_3$+10% MeOD) $\delta_H$: 7.70 (d, J=7.44 Hz, 2H), 7.50 (br s, 2H), 7.38-7.28 (m, 6H), 7.26-7.07 (m, 12H), 4.35-4.21 (m, 2H), 4.10-3.92 (m, 3H), 3.55 (d, J=5.84 Hz, 3H), 3.45 (m, 1H), 2.69-2.36 (m, 4H), 2.32-2.22 (m, 2H), 1.92 (m, 1H), 1.79 (m, 1H), 1.38 (s, 9H), 0.91 (br s, 1H), 0.82-0.67 (m, 4H). MS (ES$^+$) 933.5 (100%, [M+Na]$^+$).

(7): (R)-4-{(S)-1-[1-(1-Hydroxy-2-methoxycarbonyl-ethyl)-cyclopropylcarbamoyl]-2-tritylsulfanyl-ethylcarbamoyl}-4-((E)-(S)-3-hydroxy-7-tritylsulfanyl-hept-4-enoylamino)-butyric acid tert-butyl ester To 5 (1.088 g, 1.19 mmol) in MeCN/CH$_2$Cl$_2$ (20 mL) was added diethylamine (1.5 mL, 7.5% v/v), and the resulting mixture was stirred for 1.5 h. The mixture was then concentrated in vacuo, and MeCN (4×20 mL) was added, then removed in vacuo, and the crude amine was placed under high vacuum for 2 h. Subsequently, to a solution of PyBOP (650 mg, 1.25 mmol) and the carboxylic acid 6 (506.5 mg, 1.21 mmol (prepared according to the procedure outlined in Yurek-George, A. et al, *J. Am. Chem. Soc.* 2004, 126, 1030)) in CH$_2$Cl$_2$ (15 mL) was added diisopropylethylamine (0.65 mL, 3.73 mmol) under Ar(g), and the mixture was stirred for 3 min. A solution of the resultant deprotected amine of 5 in MeCN (15 mL) was added, and the mixture was allowed to stir at rt for 16 h, after which time the solvent was then removed in vacuo. Purification by flash column chromatography on silica (eluant 4:6-1:1-6:4-7:3-8:2 EtOAc/Hexane) gave 7 (940 mg, 0.862 mmol, 72%) as a white solid, and as a mixture of diastereoisomers that were not resolved by $^1$H NMR.

$^1$H NMR (400 MHz, CDCl$_3$) $\delta_H$: 7.39-7.29 (m, 10H), 7.28-7.11 (m, 20H), 5.47 (m, 1H), 5.35 (m, 1H), 4.34 (m, 1H), 4.12 (m, 1H), 3.97 (td, J=6.85, 3.53 Hz, 1H), 3.57 (s, 3H), 3.49-3.31 (m, 2H), 2.54-1.79 (m, 14H), 1.37 (s, 9H), 0.96-0.63 (m, 4H). MS (ES$^+$) 1111.5 (100%, [M+Na]$^+$). R$_f$ 0.17 EtOAc/Hexane (6:4).

(8): (R)-4-{(S)-1-[1-(2-Carboxy-1-hydroxy-ethyl)-cyclopropylcarbamoyl]-2-tritylsulfanyl-ethylcarbamoyl}-4-((E)-(S)-3-hydroxy-7-tritylsulfanyl-hept-4-enoylamino)-butyric acid tert-butyl ester To 7 (927.1 mg, 0.850 mmol) in THF (12 mL) at 0° C. was added LiOH (30.6 mg, 1.28 mmol) in water (3 mL) and the reaction mixture was stirred for 3.25 h. The mixture was then quenched with 1M HCl (aq) (20 mL), diluted with water (20 mL), and treated with EtOAc (60 mL). The layers were separated, and the product was extracted with EtOAc (3×60 mL). The organic layers were combined, washed with saturated brine (50 mL), dried (MgSO$_4$), and concentrated in vacuo to give the product 8 (789.1 mg, 86%) as a white solid (diastereoisomers 1:1 ratio). Compound 8 was used in the next step further purification [MS (ES$^+$) 1097.4 (100%, [M+Na]$^+$)].

(9): 3-[(6S,9R,13S)-17-Hydroxy-5,8,11,15-tetraoxo-13-((E)-4-tritylsulfanyl-but-1-enyl)-6-tritylsulfanyl-methyl-14-oxa-4,7,10-triaza-spiro[2.14]heptadec-9-yl]-propionic acid tert-butyl ester To a solution of MNBA (303.7 mg, 0.882 mmol) and DMAP (215.6 mg, 1.76 mmol) in CH$_2$Cl$_2$ (135 mL) was added dropwise a solution of the acid 8 (787 mg, 0.731 mmol) in CH$_2$Cl$_2$ (550 mL) over 3 h, and the mixture was then stirred for 16 h; the mixture was subsequently concentrated in vacuo to furnish a brown solid. Purification by column chromatography on silica (eluant 0:1-1:99-2:98-3:97 MeOH/CH$_2$Cl$_2$) gave 9 (430.2 mg, 0.407 mmol, 56%) as a white solid. The diastereoisomers were separable by flash column chromatography, though were used as a mixture for the subsequent reaction.

$^1$H NMR (400 MHz, CDCl$_3$) δ$_H$: 7.90 (d, J=3.26 Hz, 1H), 7.85 (d, J=3.39 Hz, 1H), 7.44 (t, 23H), 7.37-7.17 (m, 37H), 7.11 (s, 1H), 6.49-6.37 (m, 2H), 5.73-5.57 (m, 3H), 5.42-5.28 (m, 3H), 4.63-4.54 (m, 2H), 4.45 (m, 1H), 4.00 (m, 1H), 3.50-3.37 (m, 2H), 3.12 (dd, J=11.98, 5.84 Hz, 1H), 2.91-2.33 (m, 14H), 2.29-1.88 (m, 15H), 1.47 (s, 9H), 1.47 (s, 9H), 1.16-0.99 (m, 4H), 0.92-0.81 (m, 3H), 0.79-0.67 (m, 2H). R$_f$ 0.39+0.35 (MeOH/CH$_2$Cl$_2$ (5:95).

Compounds XIa and XIb 3-((E)-(1S,9S,20R)-5-Hydroxy-6,6-cyclopropyl-3,8,18,21-tetraoxo-2-oxa-11,12-dithia-7,19,22-triaza-bicyclo[7.7.6]docos-15-en-20-yl)-propionic acid tert-butyl ester To a solution of iodine (1.045 g, 4.12 mmol) in CH$_2$Cl$_2$/MeOH (9:1) (0.84 L) was added dropwise a solution of 9 (430.2 mg, 0.410 mmol) in CH$_2$Cl$_2$/MeOH (9:1) (0.22 L) over 4 h 40 min. The e reaction mixture was then allowed to stir for a further 30 min after which time sodium thiosulfate (300 mL, 100 equiv) was added. The resulting layers were then separated, and the product was extracted with EtOAc (3×250 ml). The organic layers were then isolated, combined, and dried (MgSO$_4$), and the solvent was removed in vacuo. Purification was then performed using column chromatography on silica (eluant 1:99-2:98-3:97 MeOH/CH$_2$Cl$_2$) to give isomer 1, compound XIa (73.8 mg, 0.129 mmol, 32%) as a white solid and isomer 2, compound XIa (60.27 mg, 0.105 mmol, 26%) as a white solid.

Isomer 1 (Compound XIa):

$^1$H NMR (400 MHz, CDCl$_3$) δ$_H$: 8.35 (d, J=2.51 Hz, 1H), 7.59 (br s, 1H), 6.82 (d, J=8.66 Hz, 1H), 6.46 (br s, 1H), 5.80 (d, J=15.18 Hz, 1H), 5.47 (br s, 1H), 5.17 (d, J=10.16 Hz, 1H), 4.93 (br s, 1H), 4.01 (ddd, J=10.89, 3.92, 3.64 Hz, 1H), 3.59 (br s, 1H), 3.40 (td, J=10.60, 5.77 Hz, 1H), 3.22 (dd, J=13.18, 6.78 Hz, 2H), 3.08 (br s, 1H), 2.90 (dd, J=13.30, 5.77 Hz, 1H), 2.71 (ddd, J=18.26, 7.28, 2.45 Hz, 3H), 2.56 (d, J=11.29 Hz, 2H), 2.50 (dd, J=13.24, 1.32 Hz, 1H), 2.38 (ddd, J=18.35, 9.76, 2.51 Hz, 1H), 2.15-2.02 (m, 2H), 1.48 (s, 9H), 1.39-1.33 (m, 1H), 1.13-1.07 (m, 1H), 0.87-0.77 (m, 2H). MS (ES$^+$) 593.7 (100%, [M+Na]$^+$). R$_f$ 0.46 CH$_2$Cl$_2$/MeOH (95:5).

Isomer 2 (Compound XIb):

$^1$H NMR (400 MHz, CDCl$_3$) δ$_H$: 8.57 (d, J=3.14 Hz, 1H), 7.32 (s, 1H), 6.85 (d, J=9.79 Hz, 1H), 6.22 (m, 1H), 5.82 (br s, 1H), 5.77 (m, 1H), 4.92 (m, 1H), 4.39 (d, J=10.04 Hz, 1H), 4.11 (m, 1H), 3.80 (td, J=9.25, 3.58 Hz, 1H), 3.42 (dd, J=14.81, 8.41 Hz, 1H), 3.17 (ddd, J=7.75, 5.74, 5.58 Hz, 1H), 3.07 (dd, J=14.87, 3.45 Hz, 1H), 2.98 (dd, J=13.05, 6.78 Hz, 1H), 2.88 (dd, J=14.12, 3.70 Hz, 1H), 2.79-2.63 (m, 4H), 2.52 (dd, J=13.11, 1.32 Hz, 2H), 2.47-2.37 (m, 1H), 2.17-2.10 (m, 2H), 1.48 (s, 9H), 1.19 (m, 1H), 0.99-0.81 (m, 3H). MS (ES$^+$) 593.7 (100%, [M+Na]$^+$). R$_f$ 0.38 CH$_2$Cl$_2$/MeOH (95:5)

Compound XII 3-((E)-(1S,9S,20R)-5-Hydroxy-6,6-cyclopropyl-3,8,18,21-tetraoxo-2-oxa-11,12-dithia-7,19,22-triaza-bicyclo[7.7.6]docos-15-en-20-yl)-propionic acid

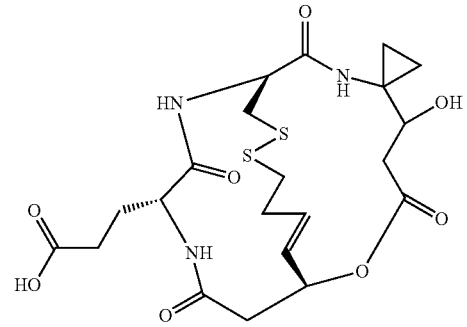

To compound XIa (35.94 mg, 0.0629 mmol) was added TFA (2 mL) and triethylsilane (100 μL, 0.626 mmol) at rt, and the reaction mixture was stirred for 1 h 40 min. The mixture was then concentrated in vacuo, and purification was performed by flash column chromatography on silica (eluant 1:99-2:98-3:97-4:96 MeOH/CH$_2$Cl$_2$) to give compound XII (14.1 mg, 0.0343 mmol, 44%) as a white solid.

$^1$H NMR (400 MHz, CDCl$_3$+10% MeOD) δ$_H$: 8.48 (d, J=2.51 Hz, 1H), 7.68 (s, 1H), 6.84 (d, J=8.78 Hz, 1H), 6.27 (m, 1H), 5.76 (d, J=15.18 Hz, 1H), 5.40 (br s, 1H), 4.83 (br s, 1H), 3.98 (td, J=7.22, 3.14 Hz, 1H), 3.45-3.27 (m, 6H), 3.13 (dd, J=13.05, 6.90 Hz, 2H), 2.83 (dd, J=13.36, 5.71 Hz, 1H), 2.75-2.38 (m, 6H), 2.10-2.03 (m, 2H), 1.31 (m, 1H), 1.04 (m, 1H), 0.84-0.73 (m, 2H). MS (ES$^+$) 538.2 (100%, [M+Na]$^+$). R$_f$ 0.17 CH$_2$Cl$_2$/MeOH (95:5).

Compound XIII 3-((E)-(1S,9S,20R)-5-Hydroxy-6,6-cyclopropyl-3,8,18,21-tetraoxo-2-oxa-11,12-dithia-7,19,22-triaza-bicyclo[7.7.6]docos-15-en-20-yl)-N-(2,2,2-trifluoro-ethyl)-propionamide

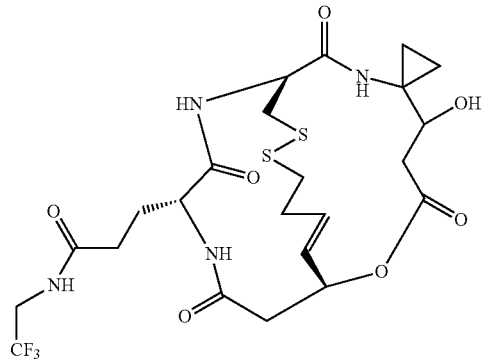

To compound XII (14.1 mg, 0.0273 mmol), EDC (21.23 mg, 0.111 mmol) and HOBt (4.40 mg, 0.0326 mmol) was added THF (0.32 mL) followed by CHCl$_3$ (1.3 mL) and the reaction mixture was stirred for 2 min. 2,2,2-Trifluoroethylamine (25 μL, 0.314 mmol) was added, and the mixture subsequently stirred for 18 h The mixture was then concentrated in vacuo, CH$_2$Cl$_2$ was added, then 1M HCl (aq), the layers separated and the crude product extracted with EtOAc. The organics were combined and dried (MgSO$_4$), and purification was carried out by flash column chromatography on silica (eluant 1:99-2:98-3:97-4:96 MeOH/CH$_2$Cl$_2$) to give XIII (9.49 mg, 0.0159 mmol, 58%) as a white solid.

$^1$H NMR (400 MHz, CDCl$_3$+10% MeOD) $\delta_H$: 8.97 (br s, 1H), 7.72 (s, 1H), 6.89 (d, J=7.40 Hz, 1H), 6.25 (br s, 1H), 5.87 (d, J=15.31 Hz, 1H), 5.45 (br s, 1H), 4.85 (br s, 1H), 3.97 (m, 1H), 3.94-3.76 (m, 2H), 3.40 (dd, J=10.85, 5.83 Hz, 1H), 3.17 (dd, J=13.05, 6.90 Hz, 1H), 2.88 (dd, J=13.43, 5.77 Hz, 1H), 2.71-2.56 (m, 3H), 2.56-2.45 (m, 3H), 2.43-2.32 (m, 6H), 2.19-2.02 (m, 2H), 1.34 (m, 1H), 1.08 (m, 1H), 0.87-0.76 (m, 2H). MS (ES$^+$) 619.2 (100%, [M+Na]$^+$). R$_f$ 0.17 CH$_2$Cl$_2$/MeOH (94:6).

Compound XIV 3-((E)-(1S,10S,21R)-7,7-Dimethyl-3,6,9,19,22-pentaoxo-2-oxa-12,13-dithia-5,8,20,23-tetraaza-bicyclo[8.7.6]tricos-16-en-21-yl)-propionic acid tert-butyl ester and Compound XV 3-((E)-(1S,10S,21R)-7,7-Dimethyl-3,6,9,19,22-pentaoxo-2-oxa-12,13-dithia-5,8,20,23-tetraaza-bicyclo[8.7.6]tricos-16-en-21-yl)-propionic acid

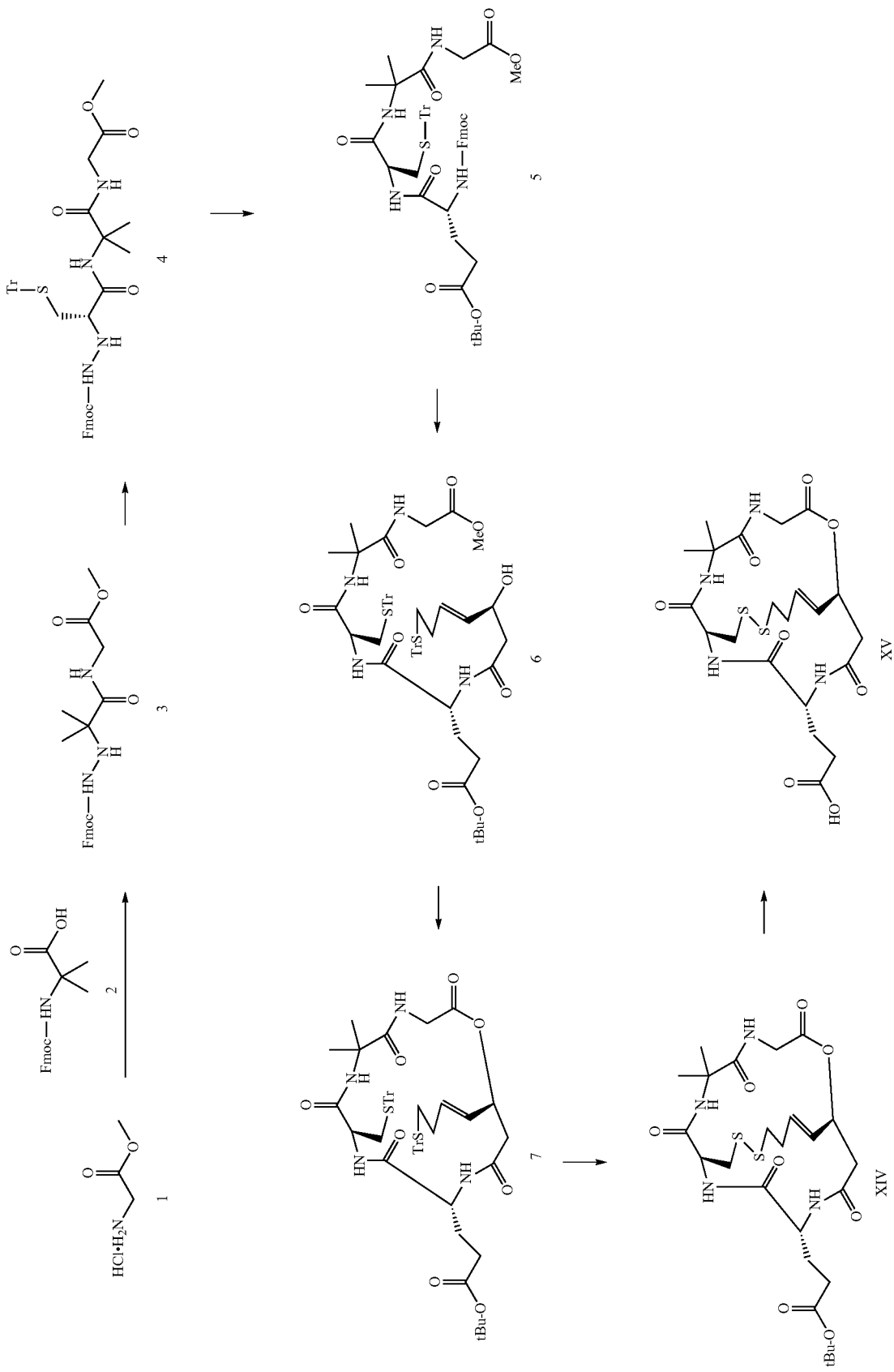

(3): [2-(9H-Fluoren-9-ylmethoxycarbonylamino)-2-methyl-propionylamino]-acetic acid methyl ester To a solution of commercially-available 2 (1.29 g, 3.96 mmol, 1.1 eq) and PyBOP (2.06 g, 3.96 mmol, 1.1 eq) in MeCN (60 mL) was added at 0° C. diisopropylethylamine (1.88 mL, 10.8 mmol, 3.0 eq) dropwise. After 5 min, a solution of H-Gly-(OMe).HCl, 1 (452 mg, 3.6 mmol, 1 eq) in $CH_2Cl_2$ (60 mL) was added to the reaction mixture dropwise. The solution was then warmed to rt overnight, and the solvent was subsequently removed in vacuo. Purification by column chromatography on silica (using hexane/EtOAc, 1:3) yielded 3 (1.42 g, 3.59 mmol, 99%) as a white solid.

$^1$H NMR (300 MHz, $CDCl_3$+10% MeOD) $\delta_H$: H 7.72 (d, J=7.4 Hz, 2H), 7.57 (d, J=7.3 Hz, 2H), 7.23-7.40 (m, 4H), 4.30-4.48 (m, 2H), 4.12-4.22 (m, 3H), 3.67 (s, 3H), 1.44 (br. s., 6H). MS (ES$^+$) 419.7 (100%, [M+Na]$^+$). $R_f$ (hexane/EtOAc, 1:3)=0.35.

(4): {2-[(S)-2-(9H-Fluoren-9-ylmethoxycarbonylamino)-3-tritylsulfanyl-propionylamino]-2-methyl-propionylamino}-acetic acid methyl ester To a solution of 3 (1.60 g, 4.04 mmol, 1 eq) in MeCN (80 mL) was added at rt diethylamine (8 mL, 10% v/v) dropwise. After 1 h, the solution was concentrated in vacuo and co-evaporated with MeCN (2×20 mL), then with $CH_2Cl_2$/hexane (10 mL). The resultant oil was then dried under high vacuum for 3 h. To a solution of Fmoc-D-Cys-(Trt)-OH (2.60 g, 4.44 mmol, 1.1 eq) and PyBOP (2.31 g, 4.44 mmol, 1.1 eq) in MeCN (60 mL) was added at 0° C. diisopropylethylamine (1.76 mL, 10.1 mmol, 2.5 eq) dropwise. After 5 min, the crude amine solution in $CH_2Cl_2$ (60 mL) was added dropwise to the reaction mixture. The solution was then warmed to rt overnight. The solvent was removed in vacuo. Purification by column chromatography on silica (hexane/EtOAc, 1:1) yielded 4 (2.79 g, 3.76 mmol, 93%) as a white solid.

$^1$H NMR (400 MHz, $CDCl_3$+10% MeOD) $\delta_H$: 7.69-7.74 (m, 2H), 7.53-7.59 (m, 2H), 7.31-7.38 (m, 8H), 7.16-7.27 (m, 11H), 4.26-4.38 (m, 2H), 4.15-4.19 (m, 2H), 3.75 (d, J=6.0 Hz, 2H), 3.59 (s, 3H), 2.46-2.62 (m, 2H), 1.45 (s, 3H), 1.44 (s, 3H). MS (ES$^+$) 764.6 (100%, [M+Na]$^+$). $R_f$ (hexane/EtOAc, 1:3)=0.45.

(5): (R)-4-(9H-Fluoren-9-ylmethoxycarbonylamino)-4-{(S)-1-[1-(methoxycarbonylmethyl-carbamoyl)-1-methyl-ethylcarbamoyl]-2-tritylsulfanyl-ethylcarbamoyl}-butyric acid tert-butyl ester To a solution of 4 (1.29 g, 1.74 mmol, 1 eq) in MeCN (35 mL) was added at rt diethylamine (3.5 mL, 10% v/v) dropwise. After 1 h, the solution was concentrated in vacuo and co-evaporated with MeCN (2×10 mL), then with $CH_2Cl_2$/hexane (5 mL). The resultant oil was then dried under high vacuum for 3 h. To a solution of Fmoc-D-Glu-(OtBu)-OH (814 mg, 1.91 mmol, 1.1 eq) and PyBOP (996 mg, 1.91 mmol, 1.1 eq) in MeCN (25 mL) was added at 0° C. diisopropylethylamine (0.76 mL, 4.4 mmol, 2.5 eq) dropwise. After 5 min, the crude amine solution in $CH_2Cl_2$ (25 mL) was added dropwise to the reaction mixture. The solution was then warmed to rt overnight. The solvent was removed in vacuo. Purification by column chromatography on silica (eluting with hexane/EtOAc, 2:3) yielded 5 (1.60 g, 1.73 mmol, 95%) as a white solid.

$^1$H NMR (300 MHz, $CDCl_3$+10% MeOD) $\delta_H$: 7.06-7.79 (m, 23H), 4.16-4.41 (m, 2H), 3.95-4.12 (m, 2H), 3.77-3.90 (m, 2H), 3.59 (br. s., 5H), 2.46-2.67 (m, 1H), 2.22-2.34 (m, 1H), 1.74-1.98 (m, 2H), 1.37 (s, 9H), 1.20 (br. s., 6H). MS (ES$^+$) 949.4 (100%, [M+Na]$^+$). $R_f$ (hexane/EtOAc, 2:3)=0.25.

(6): (R)-4-((E)-(S)-3-Hydroxy-7-tritylsulfanyl-hept-4-enoylamino)-4-{(S)-1-[1-(methoxycarbonylmethyl-carbamoyl)-1-methyl-ethylcarbamoyl]-2-tritylsulfanyl-ethylcarbamoyl}-butyric acid tert-butyl ester To a solution of 5 (1.60 g, 1.73 mmol, 1 eq) in MeCN (35 mL) was added at rt diethylamine (3.5 mL, 10% v/v) dropwise. One hour later, the solution was concentrated in vacuo and co-evaporated with MeCN (2×10 mL), then with $CH_2Cl_2$/hexane (5 mL). The resultant oil was then dried under high vacuum for 3 h. To a solution of (E)-(S)-3-hydroxy-7-tritylsulfanyl-hept-4-enoic acid (758 mg, 1.81 mmol, 1.05 eq) and PyBOP (988 mg, 1.90 mmol, 1.1 eq) in MeCN (25 mL) was added at 0° C. diisopropylethylamine (0.75 mL, 4.3 mmol, 2.5 eq) dropwise. After 5 min, the crude amine solution in $CH_2Cl_2$ (25 mL) was added dropwise to the reaction mixture. The solution was then warmed to rt overnight. The solvent was removed in vacuo. Purification by column chromatography on silica (eluting with hexane/EtOAc, 1:4) yielded 6 (1.61 g, 1.46 mmol, 85%) as a white solid.

$^1$H NMR (300 MHz, $CDCl_3$+10% MeOD) $\delta_H$: 7.09-7.44 (m, 30H), 5.28-5.58 (m, 2H), 4.23-4.38 (m, 1H), 4.02-4.14 (m, 1H), 3.73-3.94 (m, 3H), 3.64 (s, 3H), 3.60 (s, 2H), 2.01-2.59 (m, 10H), 1.43 (s, 3H), 1.39 (s, 3H), 1.37 (s, 9H). MS (ES$^+$) 1127.7 (100%, [M+Na]$^+$). $R_f$ (hexane/EtOAc, 1:4)=0.25.

(7): 3-[(9S,12R,16S)-6,6-Dimethyl-2,5,8,11,14-pentaoxo-16-((E)-4-tritylsulfanyl-but-1-enyl)-9-tritylsulfanylmethyl-1-oxa-4,7,10,13-tetraaza-cyclohexadec-12-yl]-propionic acid tert-butyl ester To a solution of 6 (1.61 g, 1.46 mmol, 1 eq) in THF (49 mL) at 0° C. was added a solution of LiOH (52.4 mg, 2.19 mmol, 1.5 eq) in $H_2O$ (9 mL) dropwise. The mixture was stirred for 1.5 h, then quenched with 1N HCl (12 mL) and brine (10 mL). The organic layer was isolated, and the resulting aqueous layer was further extracted with EtOAc (2×15 mL) and $CH_2Cl_2$ (15 mL). The combined organic extracts were dried over $MgSO_4$ and the solvent was removed in vacuo. The resulting carboxylic acid was then dried under high vacuum for 2 h. To a solution of MNBA (603 mg, 1.75 mmol, 1.2 eq) and DMAP (428 mg, 3.5 mmol, 2.4 eq) in $CH_2Cl_2$ (1.3 L) was added a solution of the crude carboxylic acid in $CH_2Cl_2$ (220 mL) and THF (30 mL) dropwise over 3 h. The reaction mixture was then stirred at overnight. The solvent was removed in vacuo. Purification by column chromatography on silica (eluting with hexane/EtOAc, 1:4) yielded 7 (982 mg, 0.92 mmol, 63%) as a pale yellow solid.

$^1$H NMR (400 MHz, $CDCl_3$+10% MeOD) $\delta_H$: 7.09-7.40 (m, 30H), 5.51-5.62 (m, 1H), 5.37-5.45 (m, 1H), 5.27-5.37 (m, 1H), 4.03-4.10 (m, 1H), 3.94-4.02 (m, 1H), 3.75-3.84 (m, 1H), 3.59 (t, J=6.8 Hz, 1H), 2.49-2.59 (m, 3H), 2.35-2.44 (m, 2H), 2.07-2.31 (m, 4H), 1.66-2.02 (m, 4H), 1.49 (s, 3H), 1.35 (s, 9H), 1.31 (s, 3H). MS (ES$^+$) 1095.7 (100%, [M+Na]$^+$). $R_f$ (hexane/EtOAc, 1:5)=0.25.

Compound XIV 3-((E)-(1S,10S,21R)-7,7-Dimethyl-3,6,9,19,22-pentaoxo-2-oxa-12,13-dithia-5,8,20,23-tetraaza-bicyclo[8.7.6]tricos-16-en-21-yl)-propionic acid tert-butyl ester The reaction was undertaken in two equal batches.

To a solution of $I_2$ (1.16 g, 4.55 mmol, 10 eq) in $CH_2Cl_2$/MeOH (1.30 L, 9:1) was added a solution of 7 (490 mg, 0.45 mmol, 1 eq) dropwise over 2 h at rt. The mixture was quenched with a solution of $Na_2S_2O_3$ (0.1 M, 250 mL) and brine (50 mL). Both aqueous layers were combined and extracted with $CH_2Cl_2$ (2×100 mL) and EtOAc (100 mL). The combined organic extracts were dried over $MgSO_4$ and the solvent was removed in vacuo. Purification by column chromatography on silica ($CH_2Cl_2$/MeOH, 49:1) yielded compound XIV (433 mg, 0.74 mmol, 81%) as a white solid.

$^1$H NMR (400 MHz, $CDCl_3$+10% MeOD) $\delta_H$: 5.79-5.90 (m, 1H), 5.66-5.77 (m, 2H), 4.59-4.68 (m, 1H), 4.33 (d, J=17.8 Hz, 1H), 4.04-4.09 (m, 1H), 3.77 (d, J=17.7 Hz, 1H), 3.11-3.22 (m, 1H), 2.98-3.10 (m, 2H), 2.93 (dd, J=15.7, 3.9 Hz, 1H), 2.82 (dd, J=13.1, 7.3 Hz, 1H), 2.52-2.75 (m, 3H), 2.38-2.51 (m, 2H), 1.96-2.16 (m, 2H), 1.49 (s, 3H), 1.43 (s, 9H), 1.38 (s, 3H); $^{13}$C NMR (100 MHz, $CDCl_3$+5% MeOD) δ H 174.6, 173.8, 173.7, 170.7, 170.0, 168.5, 130.9, 130.7, 82.1, 70.3, 57.1, 56.5, 56.3, 43.5, 38.7, 37.2, 32.7, 31.9, 31.5, 28.3, 27.8, 25.5, 23.0. MS (ES$^+$) 609.7 (100%, [M+Na]$^+$). $R_f$ ($CH_2Cl_2$/MeOH, 49:1)=0.35.

Compound XV 3-((E)-(1S,10S,21R)-7,7-Dimethyl-3,6,9,19,22-pentaoxo-2-oxa-12,13-dithia-5,8,20,23-tetraaza-bicyclo[8.7.6]tricos-16-en-21-yl)-propionic acid To a solution of compound XIV (387.4 mg, 0.66 mmol, 1 eq) in $CH_2Cl_2$ (5 mL) was added at 0° C. TFA (11 mL, 96 mmol, 150 eq) then triethylsilane (0.51 mL, 3.17 mmol, 4.8 eq). The reaction mixture was stirred for 2 h, then warmed up to rt. The solvent was removed in vacuo. Purification by column chromatography on silica (CH2CL2:MeOH, 19:1→12:1)/AcOH:0.1% yielded compound XV (290 mg, 0.55 mmol, 83%) as a white solid.

$^1$H NMR (400 MHz, $CDCl_3$+10% MeOD) d H 7.59 (d, J=7.3 Hz, 1H), 7.44 (s, 1H), 7.10 (d, J=4.1 Hz, 1H), 5.81-5.92 (m, 1H), 5.67-5.77 (m, 2H), 4.60-4.69 (m, 1H), 4.27-4.40 (m, 3H), 4.11 (dd, J=8.5, 6.3 Hz, 1H), 3.78 (dd, J=17.7, 2.2 Hz, 1H), 3.17 (dd, J=15.7, 11.4 Hz, 1H), 2.96-3.09 (m, 2H), 2.92 (dd, J=15.7, 3.9 Hz, 1H), 2.81 (dd, J=13.1, 7.2 Hz, 1H), 2.49-2.74 (m, 5H), 1.49 (s, 3H), 1.38 (s, 3H); $^{13}$C NMR (100 MHz, $CDCl_3$+5% MeOD) δ H 176.1, 174.8, 174.0, 170.9, 170.1, 168.5, 130.83, 130.79, 70.4, 57.2, 56.7, 56.4, 43.7, 38.7, 37.2, 34.2, 31.5, 31.3, 27.8, 25.4, 23.0. MS (ES$^+$) 553.7 (100%, [M+Na]$^+$). $R_f$ ($CH_2Cl_2$/MeOH, 15:1)=0.30.

Compound XVI 3-((E)-(1S,10S,21R)-7,7-Cyclopropyl-3,6,9,19,22-pentaoxo-2-oxa-12,13-dithia-5,8,20,23-tetraaza-bicyclo[8.7.6]tricos-16-en-21-yl)-propionic acid tert-butyl ester and

Compound XVII 3-((E)-(1S,10S,21R)-7,7-Cyclopropyl-3,6,9,19,22-pentaoxo-2-oxa-12,13-dithia-5,8,20,23-tetraaza-bicyclo[8.7.6]tricos-16-en-21-yl)-propionic acid

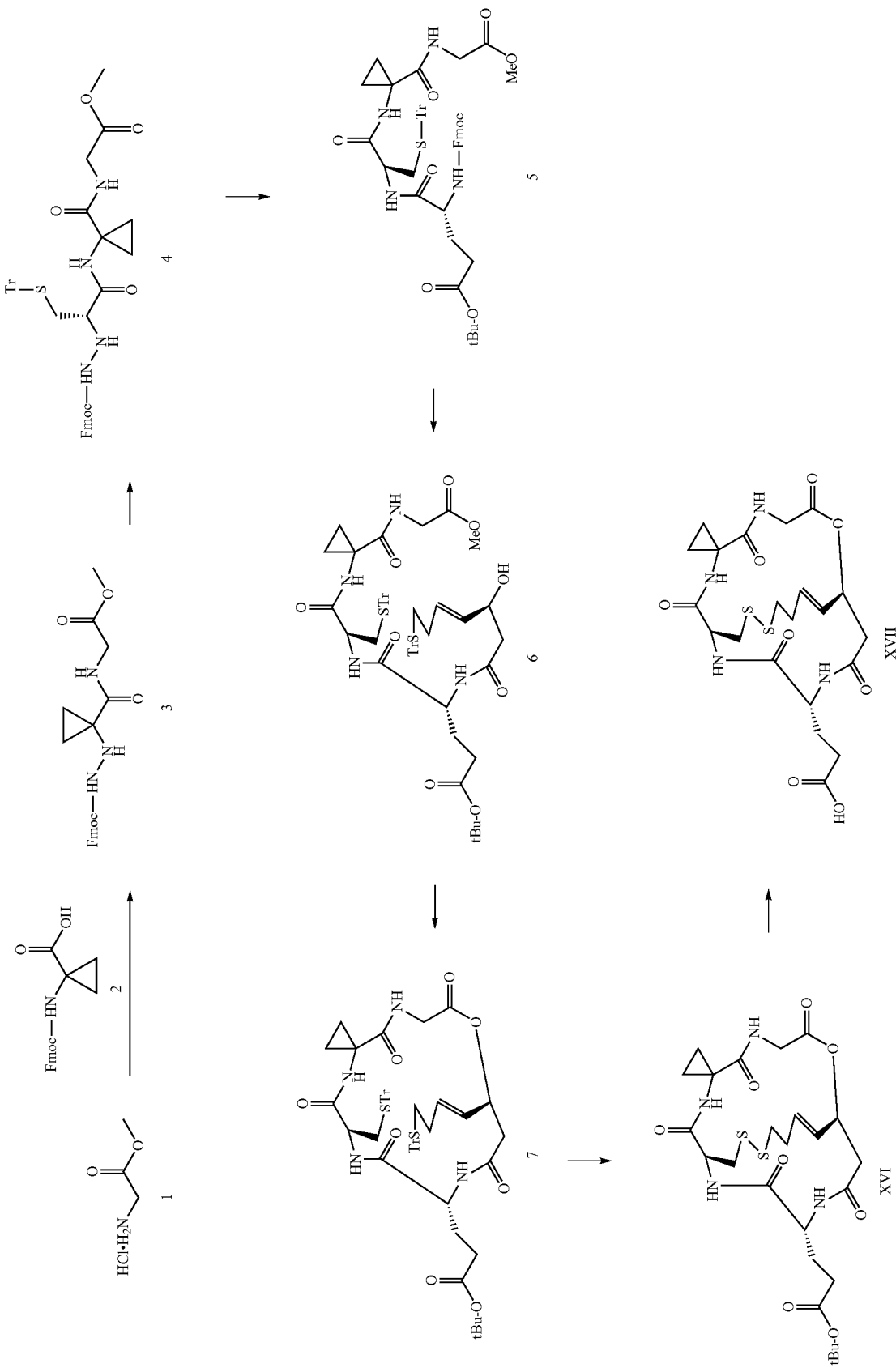

(3): {[1-(9H-Fluoren-9-ylmethoxycarbonylamino)-cyclopropanecarbonyl]-amino}-acetic acid methyl ester To a solution of commercially-available Fmoc-1-aminocyclopropanecarboxylic acid 2 (850 mg, 2.63 mmol, 1.1 eq) and PyBOP (1.37 g, 2.63 mmol, 1.1 eq) in MeCN (40 mL) was added at 0° C. diisopropylethylamine (1.25 mL, 7.17 mmol, 3.0 eq) dropwise. After 5 min, a solution of H-Gly-(OMe).HCl, 1 (300 mg, 2.39 mmol, 1 eq) in $CH_2Cl_2$ (40 mL) was added to the reaction mixture dropwise. The solution was then warmed up to rt overnight. The solvent was removed in vacuo. Purification by column chromatography on silica (eluting with hexane/EtOAc, 2:3) yielded 3 (940 mg, 2.38 mmol, 99%) as a white solid.

$^1$H NMR (300 MHz, $CDCl_3$+10% MeOD) $\delta_H$: 7.46-7.78 (m, 4H), 7.35 (t, J=7.4 Hz, 2H), 7.21-7.30 (m, 2H), 4.43 (d, J=6.3 Hz, 2H), 4.16 (t, J=6.2 Hz, 1H), 3.91 (br. s., 2H), 3.68 (br. s., 3H), 1.29-1.57 (m, 2H), 0.84-1.10 (m, 2H). MS (ES$^+$) 417.6 (100%, [M+Na]$^+$). $R_f$ (hexane/EtOAc, 2:3)=0.25.

(4): ({1-[(S)-2-(9H-Fluoren-9-ylmethoxycarbonylamino)-3-tritylsulfanyl-propionylamino]-cyclopropanecarbonyl}-amino)-acetic acid methyl ester To a solution of 3 (0.94 g, 2.38 mmol, 1 eq) in MeCN (50 mL) was added at rt diethylamine (5 mL, 10% v/v) dropwise. After 1 h, the solution was concentrated in vacuo and co-evaporated with MeCN (2×20 mL), then $CH_2Cl_2$/hexane (10 mL). The resultant oil was then dried under high vacuum for 3 h. To a solution of Fmoc-D-Cys-(Trt)-OH (1.60 g, 2.70 mmol, 1.1 eq) and PyBOP (1.35 g, 2.70 mmol, 1.1 eq) in MeCN (45 mL) was added at 0° C. diisopropylethylamine (1.03 mL, 6.2 mmol, 2.5 eq) dropwise. After 5 min, the crude amine solution in $CH_2Cl_2$ (25 mL) was added dropwise to the reaction mixture. The solution was then warmed to rt overnight. The solvent was removed in vacuo. Purification by column chromatography on silica (eluting with hexane/EtOAc, 2:3) yielded 4 (2.79 g, 3.76 mmol, 93%) as a white solid.

$^1$H NMR (400 MHz, $CDCl_3$+10% MeOD) $\delta_H$: 8.49 (s, 1H), 7.13-7.81 (m, 23H), 4.25-4.40 (m, 2H), 4.13-4.23 (m, 1H), 3.63-3.85 (m, 3H), 3.58 (s, 3H), 2.51-2.69 (m, 2H), 1.37-1.56 (m, 2H), 0.95-1.08 (m, 2H). MS (ES$^+$) 762.9 (100%, [M+Na]$^+$). $R_f$ (hexane/EtOAc, 2:3)=0.32.

(5): (R)-4-(9H-Fluoren-9-ylmethoxycarbonylamino)-4-{(S)-1-[1-(methoxycarbonylmethyl-carbamoyl)-cyclopropylcarbamoyl]-2-tritylsulfanyl-ethylcarbamoyl}-butyric acid tert-butyl ester To a solution of 4 (0.83 g, 1.12 mmol, 1 eq) in MeCN (22 mL) was added diethylamine (2.0 mL, 10% v/v) at rt dropwise. After 1 h, the solution was concentrated in vacuo and co-evaporated with MeCN (2×10 mL), then $CH_2Cl_2$/hexane (5 mL). The resultant oil was then dried under high vacuum for 3 h. To a solution of Fmoc-D-Glu-(OtBu)-OH (522 mg, 1.23 mmol, 1.1 eq) and PyBOP (638 mg, 1.23 mmol, 1.1 eq) in MeCN (20 mL) was added diisopropylethylamine (0.49 mL, 2.8 mmol, 2.5 eq) dropwise at 0° C. 5 min later, the crude amine solution in $CH_2Cl_2$ (20 mL) was added dropwise to the reaction mixture. The solution was then warmed up to rt overnight. The solvent was removed in vacuo. Purification by column chromatography on silica (hexane/EtOAc, 2:3) yielded 5 (0.97 g, 1.05 mmol, 94%) as a white solid.

$^1$H NMR (300 MHz, $CDCl_3$+10% MeOD) $\delta_H$: 7.09-7.74 (m, 23H), 4.20-4.37 (m, 2H), 3.94-4.13 (m, 2H), 3.71-3.84 (m, 3H), 3.60 (s, 3H), 2.48-2.72 (m, 2H), 2.18-2.36 (m, 2H), 1.73-1.98 (m, 2H), 1.41-1.51 (m, 2H), 1.38 (br. s., 9H), 0.96 (br. s., 2H). MS (ES$^+$) 948.0 (100%, [M+Na]$^+$). $R_f$ (hexane/EtOAc, 2:3)=0.20.

(6): (R)-4-((E)-(S)-3-Hydroxy-7-tritylsulfanyl-hept-4-enoylamino)-4-{(S)-1-[1-(methoxycarbonylmethyl-carbamoyl)-cyclopropylcarbamoyl]-2-tritylsulfanyl-ethylcarbamoyl}-butyric acid tert-butyl ester To a solution of 5 (0.97 g, 1.05 mmol, 1 eq) in MeCN (21 mL) was added at rt diethylamine (2.1 mL, 10% v/v) dropwise. After 1 h, the solution was concentrated in vacuo and co-evaporated with MeCN (2×5 mL), then $CH_2Cl_2$/hexane (5 mL). The resultant oil was then dried under high vacuum for 3 h.

To a solution of (E)-(S)-3-Hydroxy-7-tritylsulfanyl-hept-4-enoic acid (461 mg, 1.10 mmol, 1.05 eq) and PyBOP (601 mg, 1.16 mmol, 1.1 eq) in MeCN (20 mL) was added at 0° C. diisopropylethylamine (0.46 mL, 2.6 mmol, 2.5 eq) dropwise. After 5 min, the crude amine solution in $CH_2Cl_2$ (20 mL) was added dropwise to the reaction mixture. The solution was then warmed up to rt overnight. The solvent was removed in vacuo. Purification by column chromatography on silica (eluting with hexane/EtOAc, 1:4) yielded 6 (1.06 g, 0.96 mmol, 91%) as a white solid.

$^1$H NMR (400 MHz, $CDCl_3$+10% MeOD) $\delta_H$: 7.14-7.39 (m, 30H), 5.46-5.56 (m, 1H), 5.35-5.43 (m, 1H), 4.29-4.37 (m, 1H), 4.14-4.21 (m, 1H), 3.85-3.95 (m, 1H), 3.71-3.83 (m, 2H), 3.63 (s, 3H), 2.51-2.63 (m, 2H), 2.25-2.35 (m, 4H), 2.15-2.23 (m, 2H), 2.00-2.11 (m, 3H), 1.78-1.93 (m, 1H), 1.42-1.52 (m, 2H), 1.40 (s, 9H), 0.95-1.04 (m, 2H). MS (ES$^+$) 1125.6 (100%, [M+Na]$^+$). $R_f$ (hexane/EtOAc, 1:4)=0.20.

(7): 3-[(6S,9R,13S)-5,8,11,15,18-Pentaoxo-13-((E)-4-tritylsulfanyl-but-1-enyl)-6-tritylsulfanylmethyl-14-oxa-4,7,10,17-tetraaza-spiro[2.15]octadec-9-yl]-propionic acid tert-butyl ester To a solution of 6 (1.06 g, 0.96 mmol, 1 eq) in THF (32 mL) at 0° C. was added a solution of LiOH (34.5 mg, 1.44 mmol, 1.5 eq) in $H_2O$ (6 mL) dropwise. The mixture was stirred for 1.5 h, then quenched with 1N HCl (6 mL) and brine (5 mL). The organic layer was isolated and the resulting aqueous layer was further extracted with EtOAc (2×10 mL) and $CH_2Cl_2$ (10 mL). The combined organic extracts were dried over $MgSO_4$ and the solvent was removed in vacuo. The resulting carboxylic acid was then dried under high vacuum for 2 h. To a solution of MNBA (397 mg, 1.13 mmol, 1.2 eq) and DMAP (281 mg, 2.3 mmol, 2.4 eq) in $CH_2Cl_2$ (0.80 L) was added a solution of the crude carboxylic acid in $CH_2Cl_2$ (320 mL) and THF (15 mL) dropwise over 3 h. The reaction mixture was then left to stir at rt overnight. The solvent was then removed in vacuo. Purification by column chromatography on silica ($CH_2Cl_2$/MeOH, 32:1→19:1) yielded 7 (300 mg, 0.28 mmol, 29%) as a pale yellow solid.

$^1$H NMR (400 MHz, $CDCl_3$) 7.18-7.46 (m, 30H), 5.58-5.70 (m, 1H), 5.39-5.50 (m, 2H), 4.23-4.40 (m, 2H), 3.73 (dd, J=16.3, 3.8 Hz, 1H), 2.96-3.18 (m, 2H), 2.84 (dd, J=13.2, 4.5 Hz, 1H), 2.51-2.62 (m, 2H), 2.34-2.43 (m, 2H), 2.17-2.30 (m, 2H), 1.76-2.13 (m, 4H), 1.46-1.63 (m, 3H), 1.45 (s, 9H), 1.03-1.14 (m, 1H). MS (ES$^+$) 1094.0 (100%, [M+Na]$^+$). $R_f$ ($CH_2Cl_2$/MeOH, 19:1)=0.25.

Compound XVI 3-((E)-(1S,10S,21R)-7,7-Cyclopropyl-3,6,9,19,22-pentaoxo-2-oxa-12,13-dithia-5,8,20,23-tetraaza-bicyclo[8.7.6]tricos-16-en-21-yl)-propionic acid tert-butyl ester To a solution of $I_2$ (0.71 g, 2.80 mmol, 10 eq) in $CH_2Cl_2$/MeOH (700 mL, 9:1) was added a solution of 7 (300 mg, 0.28 mmol, 1 eq) over 2 h at rt dropwise. The mixture was quenched with a solution of $Na_2S_2O_3$ (0.1 M, 250 mL) and brine (50 mL). Both aqueous layers were combined and extracted with $CH_2Cl_2$ (2×100 mL) and EtOAc (100 mL). The combined organic extracts were dried over $MgSO_4$ and the solvent was removed in vacuo. Purification by column chromatography on silica ($CH_2Cl_2$/MeOH, 32:1→19:1) yielded compound XVI (107 mg, 0.18 mmol, 65%) as a white solid.

$^1$H NMR (400 MHz, $CDCl_3$+10% MeOD) 8.38 (d, J=3.7 Hz, 1H), 7.38-7.49 (m, 2H), 6.81-6.90 (m, 1H), 5.85-5.97 (m, 1H), 5.74-5.83 (m, 2H), 4.74 (ddd, J=10.2, 7.8, 3.8 Hz, 1H), 4.09-4.27 (m, 3H), 3.36 (dd, J=15.4, 10.3 Hz, 1H), 3.10 (dd, J=15.5, 3.8 Hz, 1H), 3.00-3.06 (m, 2H), 2.96 (dd, J=13.2, 7.0 Hz, 1H), 2.64 (dd, J=7.8, 2.5 Hz, 1H), 2.55 (d, J=13.1 Hz, 1H), 2.43 (s, 1H), 2.08-2.28 (m, 2H), 1.80 (ddd, J=10.2, 7.2, 4.4 Hz, 1H), 1.49 (s, 9H), 0.95-1.16 (m, 2H). MS (ES$^+$) 607.9 (100%, [M+Na]$^+$). $R_f$($CH_2Cl_2$/MeOH, 19:1)=0.30.

Compound XVII 3-((E)-(1S,10S,21R)-7,7-Cyclopropyl-3,6,9,19,22-pentaoxo-2-oxa-12,13-dithia-5,8,20,23-tetraaza-bicyclo[8.7.6]tricos-16-en-21-yl)-propionic acid To a solution of compound XVI (105 mg, 0.18 mmol, 1 eq) in TFA (1.35 mL, 18 mmol, 100 eq) was added at 0° C. triethylsilane (86 µL, 0.54 mmol, 3.0 eq). The reaction mixture was stirred for 3 h, then warmed up to rt. The solvent was removed in vacuo. Purification by column chromatography on silica (eluting with $CH_2Cl_2$/MeOH, 13:1→9:1)/AcOH: 0.1% yielded compound XVII (90.3 mg, 0.17 mmol, 95%) as a white solid.

$^1$H NMR (400 MHz, $CDCl_3$) $\delta_H$: 7.56 (s, 1H), 7.39 (d, J=7.5 Hz, 1H), 6.88 (br. s., 1H), 5.73-5.87 (m, 1H), 5.57-5.69 (m, 2H), 4.51-4.63 (m, 1H), 4.00-4.12 (m, 2H), 3.85-3.95 (m, 1H), 3.11-3.27 (m, 1H), 2.82-3.00 (m, 2H), 2.76 (dd, J=13.1, 6.9 Hz, 1H), 2.56 (br. s., 2H), 2.34-2.50 (m, 2H), 1.92-2.11 (m, 2H), 1.57-1.66 (m, 1H), 1.07-1.21 (m, 2H), 0.87-1.00 (m, 2H); $^{13}$C NMR (100 MHz, $CDCl_3$) $\delta_C$: 177.7, 174.6, 173.10, 173.08, 172.4, 169.1, 132.4, 131.9, 72.0, 58.0, 57.2, 45.0, 40.7, 38.7, 37.2, 36.7, 33.7, 32.7, 26.6, 18.2, 17.9. MS (ES$^+$) 551.7 (100%, [M+Na]$^+$). $R_f$($CH_2Cl_2$/MeOH, 9:1)=0.20.

Compound XVIII (E)-(1S,10S,21R)-7,7-Cyclopropyl-21-(3-morpholin-4-yl-3-oxo-propyl)-2-oxa-12,13-dithia-5,8,20,23-tetraaza-bicyclo[8.7.6]tricos-16-ene-3,6,9,19,22-pentaone

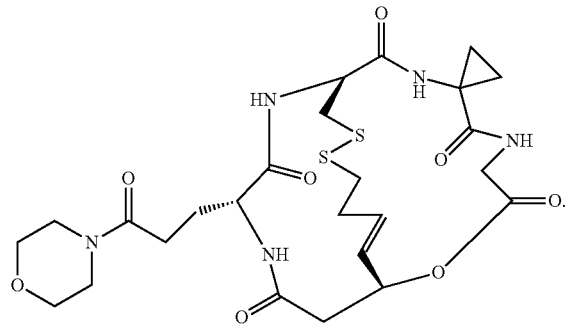

XVIII

To a solution of compound XVII (20.4 mg, 0.039 mmol, 1 eq) in MeCN (700 µL) was added PyBOP (22.0 mg, 0.042 mmol, 1.1 eq) and diisopropylethylamine (18 µL, 0.096 mmol, 2.5 eq) at 0° C. under Ar. The reaction mixture was stirred for 5 min, then a solution of morpholine (3.7 µL, 0.042 mmol, 1.05 eq) in $CH_2Cl_2$ (700 µL) was added to the mixture dropwise. The solution was left warming up to rt overnight. The solvent was removed in vacuo. Purification by column chromatography ($CH_2Cl_2$/MeOH, 1:0→32:1) followed by the use of a SCX3 cartridge with ($CH_2Cl_2$/MeOH, 1:0→99:1) yielded compound XVIII (6.1 mg, 27%) as a white solid.

$^1$H NMR (400 MHz, $CDCl_3$) $\delta_H$: 9.27 (d, J=3.1 Hz, 1H), 7.48 (s, 1H), 7.41 (d, J=8.0 Hz, 1H), 6.92 (t, J=3.9 Hz, 1H), 5.84-5.94 (m, 1H), 5.75-5.82 (m, 2H), 4.77 (ddd, J=10.3, 8.0, 4.0 Hz, 1H), 4.20 (t, J=3.6 Hz, 1H), 4.17 (d, J=4.3 Hz, 2H), 3.58-3.76 (m, 5H), 3.50 (t, J=4.8 Hz, 2H), 3.23-3.34 (m, 2H), 3.16 (dd, J=15.5, 3.9 Hz, 1H), 2.95-3.11 (m, 2H), 2.92 (dd, J=13.2, 6.9 Hz, 1H), 2.48-2.77 (m, 5H), 2.33-2.44 (m, 1H), 2.15-2.25 (m, 1H), 1.92-1.97 (m, 1H), 1.81 (m, 1H), 1.30-1.38 (m, 2H), 1.09-1.17 (m, 2H), 0.98-1.05 (m, 1H); $^{13}$C NMR (100 MHz, $CDCl_3$) δ H 174.9, 172.2, 170.8, 170.3, 170.2, 167.3, 130.6, 129.6, 70.6, 66.6, 60.6, 56.3, 47.2, 43.4, 38.9, 35.1, 34.9, 33.2, 32.7, 30.8, 16.6, 16.5. MS (ES⁺) 620.9 (100%, [M+Na]⁺). Rt (CH₂Cl₂/MeOH, 11:1)=0.35.

Compound XIX 3-((E)-(1S,10S,21R)-7,7-Cyclopropyl-3,6,9,19,22-pentaoxo-2-oxa-12,13-dithia-5,8,20,23-tetraaza-bicyclo[8.7.6]tricos-16-en-21-yl)-N-(2-methoxy-ethyl)-propionamide

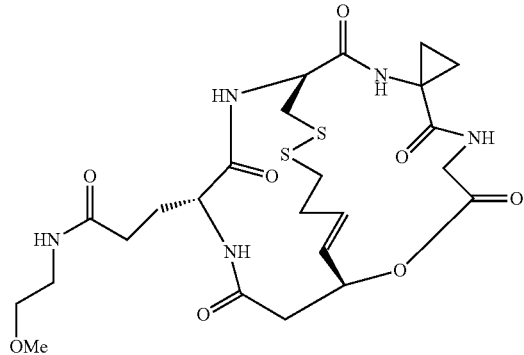

XIX

To a solution of compound XVII (26 mg, 0.05 mmol, 1 eq) in MeCN (1 mL) at 0° C. was added PyBOP (28.0 mg, 0.05 mmol, 1.1 eq) and N-ethyldiisopropylamine (22 μL, 0.12 mmol, 2.5 eq) under Ar(g). A solution of 2-methoxyethylamine (4.7 μL, 0.05 mmol, 1.1 eq) dissolved in CH₂Cl₂ (1 mL) was then added to the mixture dropwise. The reaction mixture was then left to warm to rt overnight. The mixture was then concentrated in vacuo and the residue was further purified by silica gel column chromatography with CH₂Cl₂/MeOH (1:0→19:1), then by SCX-3 cartridge with CH₂Cl₂/MeOH (1:0→32:1) to yield compound XIX as a white solid (13.5 mg, 47%).

¹H NMR (400 MHz, CDCl₃) δ$_H$: 7.46 (d, J=7.7 Hz, 1H), 5.86-5.96 (m, 1H), 5.66-5.78 (m, 2H), 4.61 (ddd, J=10.8, 7.5, 3.6 Hz, 1H), 4.11-4.19 (m, 1H), 4.05 (dd, J=9.2, 5.1 Hz, 1H), 3.95-4.02 (m, 1H), 3.40 (d, J=4.7 Hz, 2H), 3.33-3.38 (m, 2H), 3.30 (s, 3H), 3.20 (dd, J=15.5, 10.7 Hz, 1H), 3.02 (d, J=3.7 Hz, 1H), 2.97 (dd, J=6.7, 4.9 Hz, 2H), 2.83 (dd, J=13.2, 6.8 Hz, 1H), 2.69 (d, J=13.0 Hz, 1H), 2.59-2.66 (m, 2H), 2.33-2.50 (m, 2H), 2.00-2.17 (m, 2H), 1.71 (ddd, J=10.2, 7.2, 4.5 Hz, 1H), 1.20-1.28 (m, 2H) 0.92-1.07 (m, 2H). MS (ES⁺) 608.9 (100%, [M+Na]⁺).

Compound XX

N-(2-Cyano-ethyl)-3-((E)-(1S,10S,21R)-7,7-cyclopropyl-3,6,9,19,22-pentaoxo-2-oxa-12,13-dithia-5,8,20,23-tetraaza-bicyclo[8.7.6]tricos-16-en-21-yl)-propionamide

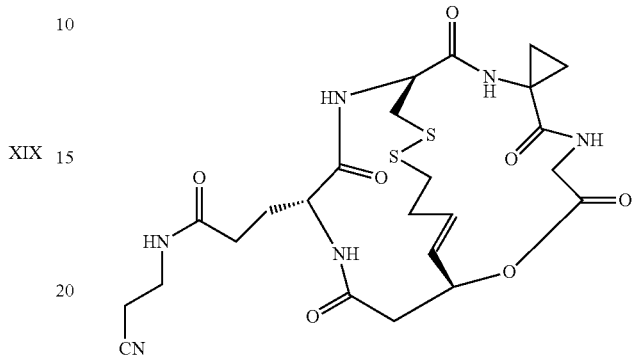

XX

To a solution of compound XVII (25 mg, 0.05 mmol, 1 eq) in MeCN (1 mL) at 0° C. was added PyBOP (27 mg of 0.05 mmol, 1.1 eq) and N-ethyldiisopropylamine (21 μL, 0.12 mmol, 2.5 eq) under Ar(g). A solution of 3-aminopropanenitrile (3.6 μL, 0.05 mmol, 1.1 eq) dissolved in CH₂Cl₂ (1 mL) was then added to the mixture dropwise. The reaction mixture was then left to warm to rt overnight. The mixture was then concentrated in vacuo and the residue was further purified by silica gel column chromatography with CH₂Cl₂/MeOH (19:1), then by SCX-3 cartridge with CH₂Cl₂/MeOH (1:0→9:1) to yield compound XX as a white solid (8.0 mg, 29%).

¹H NMR (400 MHz, CDCl₃+10% MeOH) δ$_H$: 7.46 (d, J=7.2 Hz, 1H), 5.82-5.93 (m, 1H), 5.67-5.77 (m, 2H), 4.61 (ddd, J=10.8, 7.5, 3.7 Hz, 1H), 4.10-4.18 (m, 1H), 4.04 (dd, J=8.4, 6.1 Hz, 1H), 3.95-4.02 (m, 1H), 3.36-3.44 (m, 2H), 3.21 (dd, J=15.5, 10.8 Hz, 1H), 2.94-3.04 (m, 3H), 2.83 (dd, J=13.2, 7.0 Hz, 1H), 2.59-2.69 (m, 3H), 2.55 (t, J=6.5 Hz, 2H), 2.40-2.49 (m, 1H), 2.29-2.38 (m, 1H), 2.02-2.11 (m, 2H), 1.66-1.75 (m, 1H), 1.20-1.27 (m, 2H), 0.92-1.07 (m, 2H). MS (ES⁺) 603.6 (100%, [M+Na]⁺).

Compound XXI 3-((E)-(1S,10S,21R)-7,7-Dimethyl-3,6,9,19,22-pentaoxo-2-oxa-12,13-dithia-5,8,20,23-tetraaza-bicyclo[8.7.6]tricos-16-en-21-yl)-N-(2,2,2-trifluoro-ethyl)-propionamide

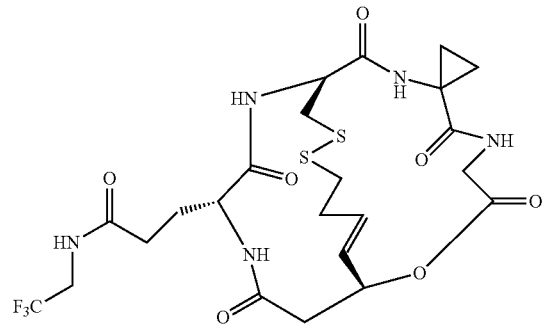

XXI

To a solution of compound XVII (26.7 mg, 0.05 mmol, 1 eq) in MeCN (1 mL) at 0° C. was added PyBOP (29 mg, 0.05 mmol, 1.1 eq) and N-ethyldiisopropylamine (22 µL, 0.12 mmol, 2.5 eq) under Ar(g). A solution of 3,3,3-trifluoropropanamine (4.8 µL, 0.05 mmol, 1.1 eq) dissolved in CH₂Cl₂ (1 mL) was then added to the mixture dropwise. The reaction mixture was then left to warm to rt overnight. The mixture was then concentrated in vacuo and the residue was further purified by silica gel column chromatography with CH₂Cl₂/MeOH (19:1), then by SCX-3 cartridge with CH₂Cl₂/MeOH (1:0→19:1) to yield compound XXI as a white solid (6.6 mg, 22%).

$^1$H NMR (400 MHz, CDCl₃) $\delta_H$: 7.39 (d, J=7.0 Hz, 2H), 5.74-5.86 (m, 1H), 5.59-5.69 (m, 2H), 4.54 (td, J=7.0, 2.9 Hz, 1H), 4.02-4.10 (m, 1H), 3.97 (dd, J=5.8, 2.2 Hz, 1H), 3.86-3.94 (m, 1H), 3.63-3.79 (m, 2H), 3.14 (ddd, J=15.3, 10.9, 1.9 Hz, 1H), 2.97-3.04 (m, 1H), 2.85-2.96 (m, 3H), 2.70-2.79 (m, 1H), 2.50-2.60 (m, 3H), 2.37-2.46 (m, 1H), 2.24-2.35 (m, 1H), 1.95-2.08 (m, 2H), 1.56-1.65 (m, 1H), 1.22-1.30 (m, 1H), 1.12-1.19 (m, 2H), 0.85-0.96 (m, 2H). MS (ES⁺) 632.9 (100%, [M+Na]⁺).

Compound XXII 3-((E)-(1S,10S,21R)-7,7-cyclopropyl-3,6,9,19,22-pentaoxo-2-oxa-12,13-dithia-5,8,20,23-tetraaza-bicyclo[8.7.6]tricos-16-en-21-yl)-N,N-diethyl-propionamide

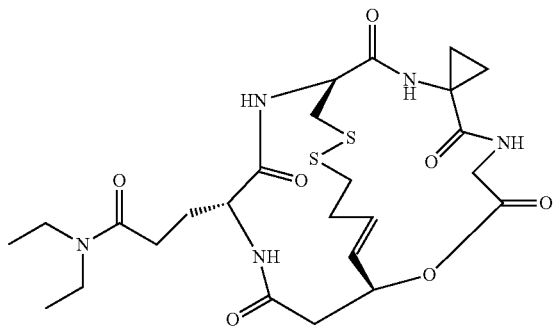

XXII

To a solution of compound XVII (25.8 mg, 0.05 mmol, 1 eq) in MeCN (1 mL) at 0° C. was added PyBOP (28 mg, 0.05 mmol, 1.1 eq) and N-ethyldiisopropylamine (21 µL, 0.12 mmol, 2.5 eq) under Ar(g). A solution of diethylamine (5.3 µL, 0.05 mmol, 1.1 eq) dissolved in CH₂Cl₂ (1 mL) was then added to the mixture dropwise. The reaction mixture was then left to warm to rt overnight. The mixture was then concentrated in vacuo and the residue was further purified by silica gel column chromatography with CH₂Cl₂/MeOH (49:1→24:1) to yield compound XXII as a white solid (13.1 mg, 46%).

$^1$H NMR (400 MHz, CDCl₃+10% MeOH) $\delta_H$: 7.58 (s, 1H), 7.44 (d, J=7.8 Hz, 1H), 5.84-5.94 (m, 1H), 5.70-5.79 (m, 2H), 4.63-4.71 (m, 1H), 4.15 (dd, J=18.4, 4.9 Hz, 1H), 4.08-4.11 (m, 1H), 4.04 (dd, J=18.5, 3.7 Hz, 1H), 3.57-3.69 (m, 3H), 3.19-3.43 (m, 4H), 3.05-3.15 (m, 4H), 2.96-3.04 (m, 2H), 2.60-2.69 (m, 3H), 2.39-2.49 (m, 1H), 2.17-2.29 (dddd, J=13.8, 9.1, 9.1, 4.4 Hz, 1H), 2.05-2.15 (m, 1H), 1.83 (ddd, J=6.4, 3.5, 3.3 Hz, 2H), 1.73 (ddd, J=10.2, 7.4, 4.6 Hz, 1H), 1.23-1.30 (m, 2H), 1.14 (t, J=7.2 Hz, 3H), 1.10 (t, J=7.1 Hz, 3H), 1.03-1.07 (m, 1H), 0.94-1.02 (m, 1H); MS (ES⁺) 607.0 (100%, [M+Na]⁺).

Compound XXIII 3-((E)-(1S,10S,21R)-7,7-cyclopropyl-3,6,9,19,22-pentaoxo-2-oxa-12,13-dithia-5,8,20,23-tetraaza-bicyclo[8.7.6]tricos-16-en-21-yl)-N-(2-morpholin-4-yl-ethyl)-propionamide

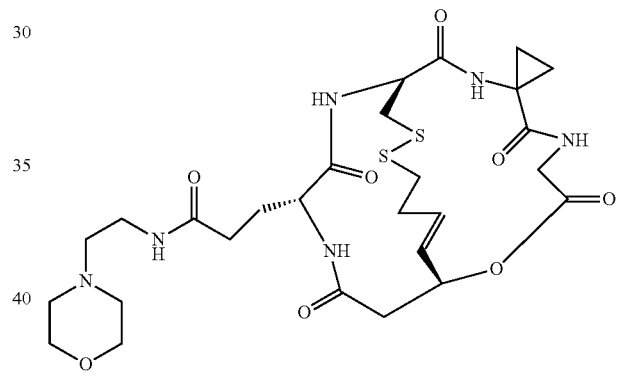

XXIII

To a solution of compound XVII (20.7 mg, 0.04 mmol, 1 eq) in MeCN (1 mL) at 0° C. was added PyBOP (22 mg, 0.04 mmol, 1.1 eq) and N-ethyldiisopropylamine (17 µL, 0.10 mmol, 2.5 eq) under Ar(g). A solution of 2-morpholinoethanamine (5.7 µL, 0.04 mmol, 1.1 eq) dissolved in CH₂Cl₂ (1 mL) was then added to the mixture dropwise. The reaction mixture was then left to warm to rt overnight. The mixture was then concentrated in vacuo and the residue was further purified by silica gel column chromatography with CH₂Cl₂/MeOH (12:1→9:1), then by SCX-3 cartridge with CH₂Cl₂/MeOH (1:0→9:1) to yield compound XXIII as a white solid (8.5 mg, 34%).

$^1$H NMR (400 MHz, CDCl₃+10% MeOH) $\delta_H$: 7.52-7.57 (m, 1H), 7.40-7.47 (m, 1H), 6.88-6.94 (m, 1H), 5.82-5.92 (m, 1H), 5.59-5.76 (m, 3H), 5.54 (dd, J=15.8, 4.5 Hz, 1H), 4.59 (ddd, J=10.8, 7.6, 3.7 Hz, 1H), 4.39 (dd, J=10.5, 3.4 Hz, 1H), 4.10-4.18 (m, 2H), 4.00-4.07 (m, 1H), 3.91 (dd, J=5.7, 2.5 Hz, 2H), 3.64-3.67 (m, 4H), 2.79-2.87 (m, 2H), 2.56-2.68 (m, 6H), 2.44-2.50 (m, 4H), 2.23-2.29 (m, 3H), 1.91-1.99 (m, 1H), 1.66-1.76 (m, 1H), 1.48 (dd, J=10.4, 3.6 Hz, 1H), 1.42 (dd, J=9.8, 3.0 Hz, 1H), 1.18-1.25 (m, 2H), 0.98-1.04 (m, 1H), 0.91-0.95 (m, 1H). MS (ES⁺) 664.0 (100%, [M+Na]⁺).

Compound XXIV (E)-(1S,10S,21R)-7,7-Cyclopropyl-21-[3-(4-methyl-piperazin-1-yl)-3-oxo-propyl]-2-oxa-12,13-dithia-5,8,20,23-tetraaza-bicyclo[8.7.6]tricos-16-ene-3,6,9,19,22-pentaone

XXIV

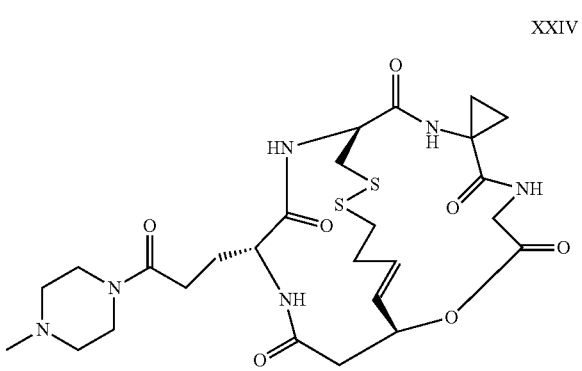 [SMILES: CN1CCN(C(=O)CC[C@H]2NC(=O)C[C@H]3/C=C/CCSSC[C@@H](NC2=O)C(=O)NC2(CC2)C(=O)NCC(=O)O3)CC1]

To a solution of compound XVII (27.6 mg, 0.05 mmol, 1 eq) in MeCN (1 mL) at 0° C. was added PyBOP (30 mg, 0.05 mmol, 1.1 eq) and N-ethyldiisopropylamine (23 µL, 0.13 mmol, 2.5 eq) under Ar(g). A solution of N-methylpiperazine (6.0 µL, 0.05 mmol, 1.1 eq) dissolved in CH$_2$Cl$_2$ (1 mL) was then added to the mixture dropwise. The reaction mixture was then left to warm to rt overnight. The mixture was then concentrated in vacuo and the residue was further purified by silica gel column chromatography with CH$_2$Cl$_2$/MeOH (19:1→9:1), then by SCX-3 cartridge with CH$_2$Cl$_2$/MeOH (1:0→0:1) and MeOH/H$_2$O/NH$_3$ (9:1:0.1) to yield compound XXIV as a white solid (15.0 mg, 47%).

$^1$H NMR (400 MHz, CDCl$_3$+10% MeOH) δ$_H$: 8.90 (d, J=3.2 Hz, 1H), 7.54 (s, 1H), 7.40 (d, J=7.7 Hz, 1H), 6.89 (t, J=3.8 Hz, 1H), 5.71-5.82 (m, 1H), 5.59-5.67 (m, 2H), 4.49-4.58 (m, 1H), 4.07 (d, J=5.2 Hz, 1H), 3.95-4.00 (m, 1H), 3.85-3.93 (m, 1H), 3.56 (s, 1H), 3.37-3.45 (m, 3H), 3.10 (dd, J=15.5, 10.9 Hz, 1H), 2.87-2.97 (m, 3H), 2.70-2.78 (m, 1H), 2.48-2.58 (m, 4H), 2.33-2.44 (m, 4H), 2.24 (br. s., 3H), 2.03-2.13 (m, 1H), 1.94 (s, 1H), 1.56-1.64 (m, 1H), 1.13-1.17 (m, 1H), 0.87-0.98 (m, 3H). MS (ES$^+$) 633.6 (100%, [M+Na]$^+$).

Compound XXV tert-Butyl 3-((1S,10S,21R, E)-3,6,9,19,22-pentaoxo-2-oxa-12,13-dithia-5,8,20,23-tetraazaspiro[bicyclo[8.7.6]tricos[16]ene-7,1'-cyclobutane]-21-yl)propanoate

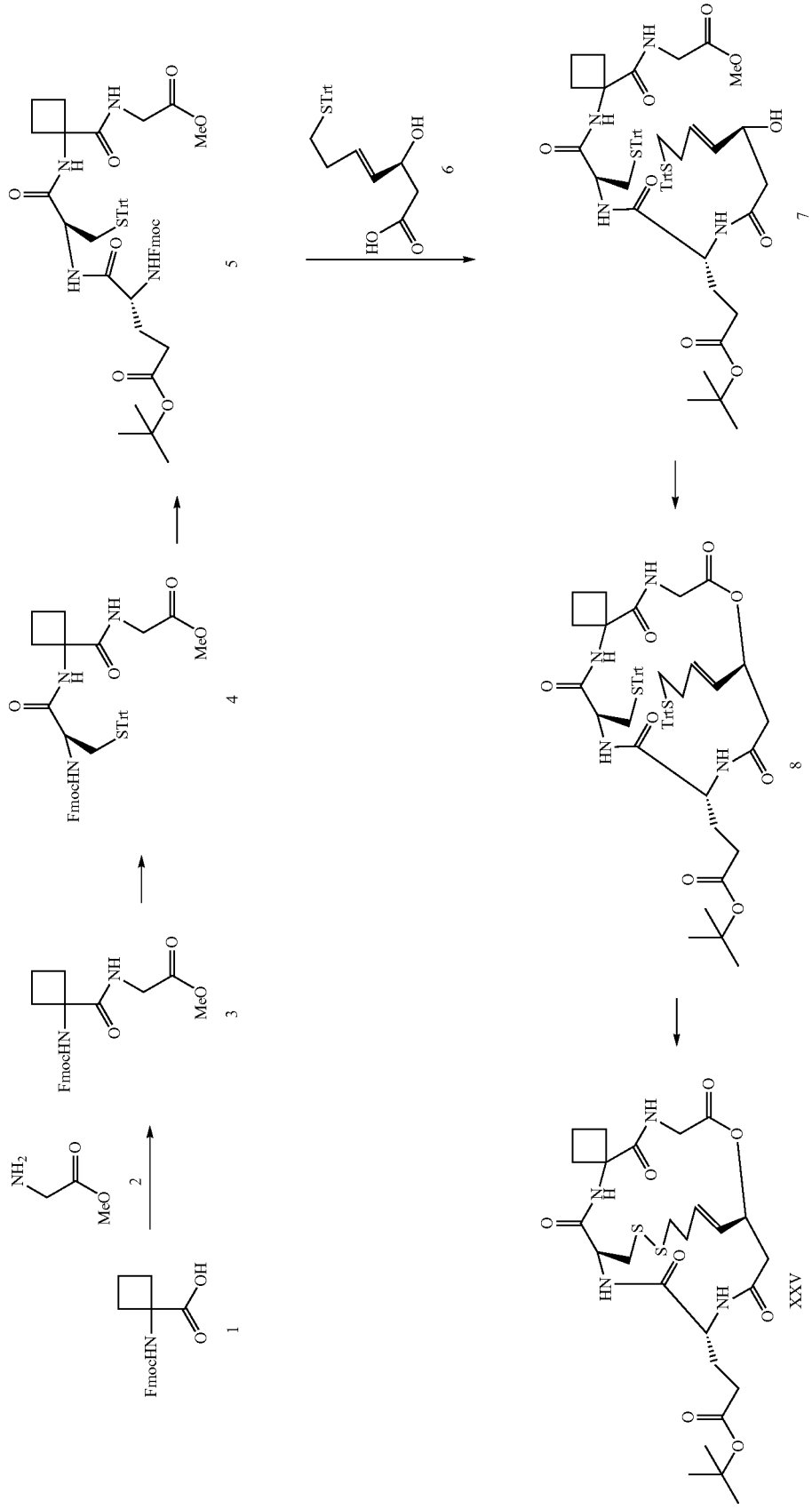

(3): {[1-(9H-fluoren-9-ylmethoxycarbonylamino)-cyclobutanecarbonyl]-amino}-acetic acid methyl ester N,N-Diisopropylethylamine (2.60 mL, 14.82 mmol) was added to 1-(9H-Fluoren-9-ylmethoxy carbonylamino)-cyclobutanecarboxylic acid, 1 (2.0 g, 5.93 mmol) and PyBOP (3.393 g, 6.52 mmol) in $CH_2Cl_2$ (150 mL) at rt under Ar(g). After 10 minutes, MeCN (150 mL) and HCl.GlyOMe, 2 (819 mg, 6.52 mmol) were added. After 16 h, the reaction mixture was concentrated under reduced pressure and the residue was purified by silica gel column chromatography eluting with hexane/EtOAc (2:1 to 1:3) to yield 3 as a white solid (2.373 g, 98%).

$^1$H NMR (300 MHz, $CDCl_3$) $\delta_H$: 7.78 (d, J=7.4 Hz, 2H), 7.59 (d, J=6.5 Hz, 2H), 7.41 (t, J=7.3 Hz, 2H), 7.32 (td, J=7.3, 0.7 Hz, 2H), 7.01 (br. s., 1H), 5.37 (br. s., 1H), 4.49 (d, J=5.8 Hz, 2H), 4.17-4.27 (m, 1H), 4.02 (br. s., 2H), 3.72 (s, 3H), 2.69 (br. s., 2H), 2.17 (br. s., 2H), 1.98 (t, J=6.6 Hz, 2H). MS (ES): 431.8 (100%, [M+Na]$^+$), 840.1 (80%, [2M+Na]$^+$).

(4): ({1-[(S)-2-(9H-Fluoren-9-ylmethoxycarbonylamino)-3-tritylsulfanyl-propionylamino]-cyclobutanecarbonyl}-amino)-acetic acid methyl ester $Et_2NH$ (2 mL) was added to 3 (2.202 g, 5.39 mmol), in MeCN (18 mL) at rt under Ar(g). After 1 h of stirring the solvent was removed under reduced pressure, then the residue was re-dissolved, evaporated with MeCN (4×20 mL) and hexane (2×20 mL). The crude product was dried under high vacuum at least 3 h. N,N-Diisopropylethylamine (2.35 mL, 13.47 mmol) was added to Fmoc-D-Cys(Trt)OH (3.473 g, 5.93 mmol) and PyBOP (3.086 g, 5.93 mmol) in $CH_2Cl_2$ (150 mL) at −10° C. under Ar(g). After 10 min of stirring, the mixture was transferred to the crude amine, solubilised in MeCN (150 mL) at −10° C. under Ar(g). The reaction mixture was then allowed to warm to rt. After 16 h, the reaction mixture was concentrated under reduced pressure and the residue was purified by silica gel column chromatography eluting with hexane/EtOAc (80:20 then 40:60) to yield 4 as a white solid (1.467 g, 36%).

$^1$H NMR (400 MHz, $CDCl_3$) $\delta_H$: 7.77 (dd, J=7.5, 3.5 Hz, 2H), 7.57 (d, J=7.5 Hz, 2H), 7.38-7.45 (m, 7H), 7.17-7.33 (m, 13H), 6.24 (s, 1H), 5.01 (d, J=6.7 Hz, 1H), 4.44 (dd, J=10.7, 6.9 Hz, 1H), 4.40 (dd, J=10.7, 6.5 Hz, 1H), 4.19 (t, J=6.4 Hz, 1H), 3.92 (dd, J=18.4, 5.9 Hz, 1H), 3.84 (dd, J=18.3, 6.1 Hz, 1H), 3.65-3.69 (m, 1H), 3.64 (s, 3H), 2.62-2.78 (m, 4H), 2.06-2.17 (m, 2H), 1.84-2.05 (m, 2H). MS (ES): 777.2 (100%, [M+Na]$^+$).

(5): (R)-4-(9H-fluoren-9-ylmethoxycarbonylamino)-4-{(S)-1-[1-(methoxycarbonylmethyl-carbamoyl)-cyclobutylcarbamoyl]-2-tritylsulfanyl-ethylcarbamoyl}-butyric acid tert-butyl ester $Et_2NH$ (2 mL) was added to 4 (1.467 g, 1.95 mmol,) in MeCN (28 mL) at rt under Ar(g). After 1 h of stirring, the solvent was removed under reduced pressure, then the residue was re-dissolved, evaporated with MeCN (4×20 mL) and hexane (2×20 mL). The crude product was dried under high vacuum at least 3 hours before use in the next step. N,N-Diisopropylethylamine (0.85 mL, 4.87 mmol) was added to Fmoc-D-Glu(tBu)OH (910 mg, 2.14 mmol) and PyBOP (1.114 g, 2.14 mmol) in $CH_2Cl_2$ (100 mL) at 0° C. under Ar(g). After 10 min of stirring, the mixture was transferred to the crude amine resulting of the deprotection 4 solubilised in MeCN (100 mL) at 0° C. under Ar(g). Then the reaction was allowed to warm to rt. After 16 h, the reaction mixture was concentrated under reduced pressure and the residue was purified by silica gel column chromatography eluting with hexane/EtOAc (70:30 to 35:65) to yield 5 as a white solid (1.485 g, 81%).

$^1$H NMR (400 MHz, $CDCl_3$) $\delta_H$: 7.77 (d, J=7.4 Hz, 2H), 7.54 (t, J=6.8 Hz, 2H), 7.37-7.44 (m, 8H), 7.10-7.34 (m, 13H), 6.68 (d, J=6.5 Hz, 1H), 6.44 (d, J=4.0 Hz, 1H), 4.33 (dd, J=10.4, 7.7 Hz, 1H), 4.24 (dd, J=9.9, 7.2 Hz, 1H), 4.08 (t, J=6.9 Hz, 1H), 3.94 (d, J=5.6 Hz, 2H), 3.65 (s, 3H), 3.02 (dd, J=13.1, 5.8 Hz, 1H), 2.74-2.84 (m, 1H), 2.63-2.73 (m, 2H), 2.52 (dd, J=12.8, 5.0 Hz, 2H), 2.37 (ddd, J=17.1, 8.7, 4.1 Hz, 2H), 2.18-2.31 (m, 2H), 1.83-2.03 (m, 4H), 1.49 (s, 9H). MS (ES): 961.8 (100%, [M+Na]$^+$).

(6): (E)-(S)-3-Hydroxy-7-tritylsulfanyl-hept-4-enoic acid

At 0° C. to a solution of (S,E)-3-hydroxy-1-((R)-4-isopropyl-2-thioxothiazolidin-3-yl)-7-(tritylthio)hept-4-en-1-one (934 mg, 1.66 mmol, prepared according to the procedure in Yurek-George, A. et al, J. Am. Chem. Soc. 2004, 126, 1030) in THF (30 mL) was added a solution of LiOH (196.1 mg, 8.19 mmol) in $H_2O$ (10 mL). The reaction mixture was allowed to warm to rt over 1 h, whereupon 1M HCl was added until the pH reached 2. EtOAc (30 mL) was then added and the layers were separated. The aqueous layer was extracted with EtOAc (20 mL) the organic layers were combined, dried ($MgSO_4$) and concentrated in vacuo. Purification by flash column chromatography (eluant 3:7-1:1-1:0 EtOAc/Hexane) gave the 6 as a white solid (600 mg, 1.43 mmol, 86%).

$^1$H NMR (300 MHz, $CDCl_3$) $\delta_H$: 7.48-7.38 (m, 6H), 7.35-7.18 (m, 9H), 5.60 (m, 1H), 5.43 (m, 1H), 4.46 (q, J=6.28, 1H), 2.59-2.51 (m, 2H), 2.28-2.19 (m, 2H), 2.09 (q, J=6.47 Hz, 2H). MS (ES$^-$) 417 (100%, [M−H]$^-$). R$_f$ 0.52 EtOAc+2 drops AcOH; [α]$_D^{27}$ −4.15 (c 0.975, $CH_2Cl_2$).

(7) (R)-4-(E)-(S)-3-hydroxy-7-tritylsulfanyl-hept-4-enoylamino)-4-{(S)-1-[1-(methoxy carbonylmethyl-carbamoyl)-cyclobutylcarbamoyl]-2-tritylsulfanyl-ethylcarbamoyl}-butyric acid tert-butyl ester $Et_2NH$ (3 mL) was added to 5 (1.480 g, 1.57 mmol) in MeCN (27 mL) at rt under Ar(g). After 1 h of stirring the solvent was removed under reduced pressure then the residue was re-dissolved and evaporated with MeCN (4×20 mL) and hexane (2×20 mL). The crude product was dried under high vacuum at least 3 h prior to use in the next step. N,N-Diisopropylethylamine (0.685 mL, 3.92 mmol) was added to a solution of 6 (724 mg, 1.73 mmol) and PyBOP (899 mg, 1.73 mmol) in $CH_2Cl_2$ (100 mL) at 0° C. under Ar(g). After 10 min of stirring, the mixture was transferred to the crude amine resulting of the deprotection of 5 dissolved in MeCN (100 mL) at 0° C. under Ar(g), then the reaction mixture was left to warm to rt. After 18.5 h the reaction was completed and the mixture was concentrated under reduced pressure. The resulting residue was purified by silica gel column chromatography eluting with hexane/EtOAc (80:20 to 20:80) to yield 7 as a white solid (1.322 g, 75%).

$^1$H NMR (400 MHz, $CDCl_3$) $\delta_H$: 7.66 (d, J=5.0 Hz, 1H), 7.39-7.44 (m, 6H), 7.34-7.39 (m, 6H), 7.27-7.33 (m, 8H), 7.16-7.27 (m, 12H), 5.52 (dt, J=15.2, 6.5 Hz, 1H), 5.36 (dd, J=15.4, 6.7 Hz, 1H), 4.45 (sxt, J=4.4 Hz, 1H), 4.28-4.35 (m, 1H), 4.19 (dt, J=7.6, 4.8 Hz, 1H), 4.08 (d, J=6.9 Hz, 1H), 3.69 (d, J=4.8 Hz, 1H), 3.65 (d, J=4.8 Hz, 1H), 3.51 (s, 3H), 2.69-2.77 (m, 1H), 2.67 (d, J=8.5 Hz, 1H), 2.64 (d, J=8.3 Hz, 1H), 2.60 (dd, J=8.4, 4.3 Hz, 1H), 2.56 (dd, J=9.2, 4.3 Hz, 1H), 2.54 (t, J=4.5 Hz, 1H), 2.43 (dd, J=7.9, 4.4 Hz, 1H), 2.38 (dd, J=7.4, 4.5 Hz, 1H), 2.27-2.35 (m, 3H), 2.14-2.26 (m, 4H), 2.06-2.12 (m, 2H), 1.87-2.00 (m, 2H), 1.41 (s, 9H). MS (ES): 1140.5 (100%, [M+Na]$^+$).

(8) 3-[(7R,10R,14R)-6,9,12,16,19-pentaoxo-14-((E)-4-tritylsulfanyl-but-1-enyl)-7-trityl sulfanylmethyl-15-oxa-5,8,11,18-tetraaza-spiro[3.15]nonadec-10-yl]-propionic acid tert-butyl ester LiOH (42 mg, 1.77 mmol) in water (4 mL) was added to 7 (1.322 g, 1.18 mmol) in THF (16 mL) at 0° C. After 1.5 h of stirring at 0° C. the reaction mixture was neutralized with aqueous 0.5 M HCl then brine (50 mL) and EtOAc (50 mL) were added. The phases were separated and the aqueous phase was extracted with EtOAc (4×25 mL). The organic phases were combined, dried over MgSO4, filtered then concentrated under reduced pressure. The crude product was dried under high vacuum before being used in the next step. The crude carboxylic acid in CH$_2$Cl$_2$/THF (740 mL, 12:1 v/v) was added dropwise over a period of 3 h to 2-methyl-6-nitrobenzoic anhydride (487 mg, 1.42 mmol) and 4-(dimethylamino)pyridine (346 mg, 2.83 mmol) in CH$_2$Cl$_2$ (300 mL) at rt under Ar(g). After 16 h, the reaction mixture was concentrated under reduced pressure and the residue was purified by silica gel column chromatography eluting with CH$_2$Cl$_2$/isopropanol (100:4 then 100:8) to yield 8 as a white solid (648 mg, 51%).

$^1$H NMR (400 MHz, CDCl$_3$) δ$_H$: 7.42 (dd, J=16.0, 8.2 Hz, 12H), 7.27-7.33 (m, 8H), 7.25-7.27 (m, 5H), 7.18-7.25 (m, 6H), 7.06 (t, J=5.3 Hz, 1H), 6.83 (d, J=5.4 Hz, 1H), 6.79 (d, J=6.8 Hz, 1H), 6.67 (s, 1H), 5.58-5.69 (m, 1H), 5.36-5.47 (m, 2H), 4.18 (dd, J=17.0, 6.7 Hz, 1H), 3.98-4.12 (m, 2H), 3.86 (dd, J=17.3, 4.2 Hz, 1H), 3.34 (q, J=7.8 Hz, 1H), 2.93 (dd, J=13.6, 8.3 Hz, 1H), 2.82 (d, J=5.6 Hz, 1H), 2.78 (d, J=5.3 Hz, 1H), 2.54 (dd, J=14.8, 4.1 Hz, 1H), 2.47 (dd, J=14.8, 6.1 Hz, 1H), 2.37 (d, 1H), 2.34 (d, J=7.0 Hz, 1H), 2.17-2.30 (m, 3H), 2.08 (d, J=6.9 Hz, 1H), 2.05 (d, J=6.8 Hz, 1H), 1.84-1.98 (m, 2H), 1.72-1.84 (m, 2H), 1.44 (s, 9H). MS (ES): 1107.8 (100%, [M+Na]$^+$).

Compound XXV 3-((E)-(1S,10S,21R)-7-cyclobutyl-3,6,9,19,22-pentaoxo-2-oxa-12,13-dithia-5,8,20,23-tetraaza-bicyclo[8.7.6]tricos-16-en-21-yl)-propionic acid tert-butyl ester Compound 8 (648 mg, 0.60 mmol) in CH$_2$Cl$_2$/CH$_3$OH (472 mL, 9:1, v/v) was added dropwise over a period of 30 min to I$_2$ (1.515 mg, 6.0 mmol) in CH$_2$Cl$_2$/CH$_3$OH (828 mL, 9:1 v/v) at rt under Ar(g). After 2 h of stirring, aqueous 0.1 M Na$_2$S$_2$O$_3$ (500 mL) and brine (150 mL) were added. The phases were separated then the aqueous phase was extracted with CH$_2$Cl$_2$ (200 mL) and EtOAc (2×100 mL). The organic phases were combined, dried over MgSO$_4$, filtered then concentrated under reduced pressure. The residue was purified by silica gel column chromatography eluting with CH$_2$Cl$_2$/CH$_3$OH (100:3) to yield compound XXV as a white solid (335 mg, 93%).

$^1$H NMR (400 MHz, CDCl$_3$) δ$_H$: 8.33 (d, J=3.4 Hz, 1H), 7.41 (s, 1H), 7.35 (d, J=7.9 Hz, 1H), 6.81 (d, J=3.9 Hz, 1H), 5.82-5.94 (m, 1H), 5.71-5.80 (m, 2H), 4.83 (ddd, J=10.4, 7.9, 3.7 Hz, 1H), 4.37 (dd, J=18.1, 6.4 Hz, 1H), 4.16 (m, J=9.8, 4.3, 4.3 Hz, 1H), 3.96 (dd, J=18.1, 2.6 Hz, 1H), 3.30 (dd, J=15.6, 10.4 Hz, 1H), 2.95-3.10 (m, 4H), 2.90 (dd, J=13.1, 7.1 Hz, 1H), 2.59-2.78 (m, 3H), 2.47-2.55 (m, 2H), 2.42 (ddd, J=18.3, 9.5, 2.9 Hz, 1H), 2.08-2.26 (m, 4H), 1.91-2.07 (m, 2H), 1.48 (s, 9H). (100 MHz, CDCl$_3$) δ$_C$: 175.55, 172.53, 172.20, 169.62, 169.51, 168.07, 130.33, 130.26, 82.41, 69.31, 59.13, 57.24, 55.07, 42.98, 38.56, 38.21, 35.97, 32.80, 32.15, 32.08, 30.14, 28.02, 24.35 (3C), 15.65. MS (ES): 621.4 (100%, [M+Na]$^+$).

Compound XXVI 3-((E)-(1S,10S,21R)-7-cyclobutyl-3,6,9,19,22-pentaoxo-2-oxa-12,13-dithia-5,8,20,23-tetraaza-bicyclo[8.7.6]tricos-16-en-21-yl)-propionic acid

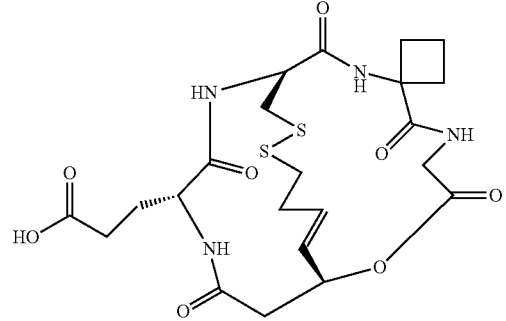

To compound XXV (273 mg, 0.416 mmol) was added Et$_3$SiH (0.37 mL, 2.3 mmol) followed by trifluoroacetic acid (1 mL). The reaction mixture was stirred at rt for 1 h 15 min, then was concentrated under reduced pressure. The remaining trifluoroacetic acid was removed by co-evaporating the crude product with toluene (4×5 mL) under reduced pressure. The residue was then purified by silica gel column chromatography eluting with CH$_2$Cl$_2$/CH$_3$OH (100:5) to yield compound XXVI as a white solid (191 mg, 76%).

$^1$H NMR (400 MHz, 9/1 CDCl$_3$/CD$_3$OD) δ$_H$: 7.65 (s, 1H), 7.49 (d, J=7.7 Hz, 1H), 6.94 (d, J=5.5 Hz, 1H), 5.82-5.95 (m, 1H), 5.68-5.80 (m, 2H), 4.78 (ddd, J=10.9, 7.6, 3.7 Hz, 1H), 4.40 (dd, J=18.0, 6.6 Hz, 1H), 4.17 (dd, J=8.7, 5.8 Hz, 1H), 3.88 (dd, J=17.9, 2.3 Hz, 4H), 3.25 (dd, J=15.6, 10.8 Hz, 1H), 2.95-3.10 (m, 4H), 2.86 (dd, J=13.2, 7.0 Hz, 1H), 2.64-2.75 (m, 2H), 2.61 (dt, J=17.6, 6.9 Hz, 1H), 2.54 (dt, J=17.4, 6.8 Hz, 1H), 2.37-2.47 (m, 1H), 2.07-2.25 (m, 4H), 1.98 (quin, J=8.5 Hz, 2H). (100 MHz, 9/1 CDCl$_3$/CD$_3$OD) δ$_C$: 175.93, 172.80, 172.71, 170.11, 169.59, 167.90, 130.27, 130.09, 69.74, 58.97, 56.03, 55.19, 42.69, 38.46, 36.76, 34.68, 32.02, 31.46, 30.82, 29.81, 24.55, 15.31.

Compound XXVII
(E)-(1S,7R,10S)-7-Isopropyl-21,21-dimethyl-2-oxa-12,13-dithia-5,8,20,23-tetraaza-bicyclo[8.7.6]tricos-16-ene-3,6,9,19,22-pentaone
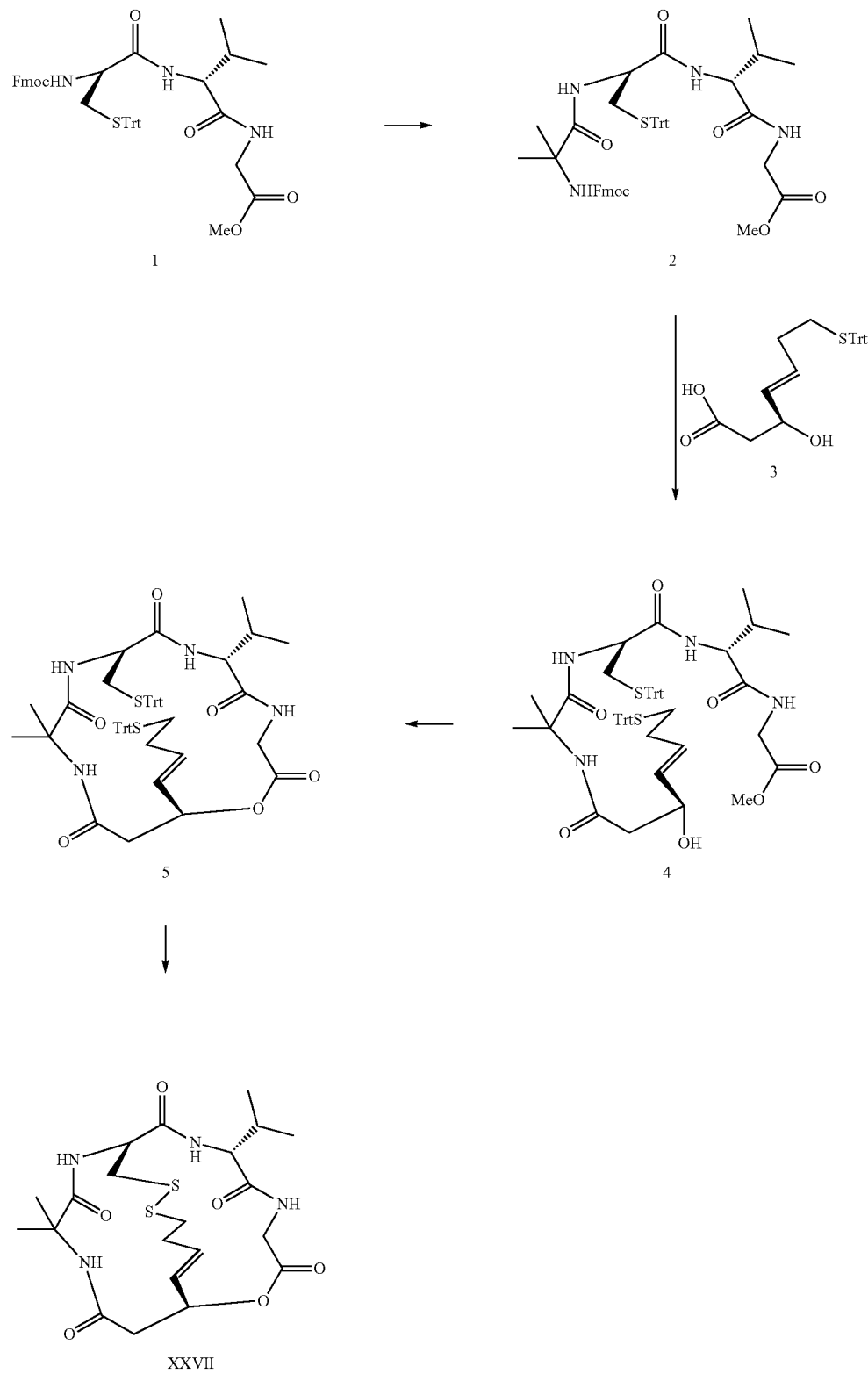

(2) ((R)-2-{(S)-2-[2-(9H-Fluoren-9-ylmethoxycarbonylamino)-2-methyl-propionylamino]-3-tritylsulfanyl-propionylamino}-3-methyl-butyrylamino)-acetic acid methyl ester Et$_2$NH (3 mL) was added to {(R)-2-[(S)-2-(9H-Fluoren-9-ylmethoxycarbonylamino)-3-tritylsulfanyl-propionylamino]-3-methyl-butyrylamino}-acetic acid methyl ester 1 (500 mg, 0.66 mmol, prepared according to WO 2006/129105) in MeCN (27 mL) at rt under Ar(g). After 1 h of stirring the solvent was removed under reduced pressure, then the residue was re-dissolved, evaporated with MeCN (4×20 mL) and hexane (2×20 mL). The crude product was dried under high vacuum at least 3 h before being used in the next step. N,N-Diisopropylethylamine (0.29 mL, 1.65 mmol) was added to Fmoc-Me-Ala-OH (237 mg, 0.73 mmol) and PyBOP (378 mg, 0.73 mmol) in CH$_2$Cl$_2$ (30 mL) at 0° C. under Ar(g). After 10 min of stirring, the mixture was transferred to the crude amine resulting of the deprotection of {(R)-2-[(S)-2-(9H-Fluoren-9-ylmethoxycarbonylamino)-3-trityl sulfanyl-propionylamino]-3-methyl-butyrylamino}-acetic acid methyl ester 1 solubilised in MeCN (30 mL) at 0° C. under Ar(g). Then the reaction was allowed to warm to rt. After 16 h, the reaction mixture was concentrated under reduced pressure and the residue was purified by silica gel column chromatography eluting with hexane/EtOAc (50:50 then 20:80) to yield 2 as a white solid (410 mg, 74%).

$^1$H NMR (400 MHz, CDCl$_3$) $\delta_H$: 7.69 (d, J=7.5 Hz, 2H), 7.00-7.58 (m, 23H), 6.77 (d, J=5.4 Hz, 1H), 4.46-4.60 (m, 1H), 4.30-4.35 (m, 1H), 4.24 (dd, J=9.7, 7.9 Hz, 1H), 3.98-4.18 (m, 3H), 3.73 (d, J=17.4 Hz, 1H), 3.59 (s, 3H), 2.83-3.03 (m, 1H), 2.35-2.42 (m, 1H), 2.31 (dd, J=12.5, 4.1 Hz, 1H), 1.97 (d, J=1.8 Hz, 1H), 1.32 (s, 3H), 1.26 (s, 3H), 0.97 (t, J=7.5 Hz, 6H). MS (ES): 863.7 (100%, [M+Na]$^+$).

(3): (E)-(S)-3-Hydroxy-7-tritylsulfanyl-hept-4-enoic acid

At 0° C. to a solution of (S,E)-3-hydroxy-1-((R)-4-isopropyl-2-thioxothiazolidin-3-yl)-7-(tritylthio)hept-4-en-1-one (934 mg, 1.66 mmol, prepared according to the procedure in Yurek-George, A. et al, J. Am. Chem. Soc. 2004, 126, 1030) in THF (30 mL) was added a solution of LiOH (196.1 mg, 8.19 mmol) in H$_2$O (10 mL). The reaction mixture was allowed to warm to rt over 1 h, whereupon 1M HCl was added until the pH reached 2. EtOAc (30 mL) was then added and the layers were separated. The aqueous layer was extracted with EtOAc (20 mL) the organic layers were combined, dried (MgSO$_4$) and concentrated in vacuo. Purification by flash column chromatography (eluant 3:7-1:1-1:0 EtOAc/Hexane) gave the 3 as a white solid (600 mg, 1.43 mmol, 86%).

$^1$H NMR (300 MHz, CDCl$_3$) $\delta_H$: 7.48-7.38 (m, 6H), 7.35-7.18 (m, 9H), 5.60 (m, 1H), 5.43 (m, 1H), 4.46 (q, J=6.28, 1H), 2.59-2.51 (m, 2H), 2.28-2.19 (m, 2H), 2.09 (q, J=6.47 Hz, 2H). MS (ES) 417 (100%, [M−H]$^-$). R$_f$ 0.52 EtOAc+2 drops AcOH; [α]$_D^{27}$ −4.15 (c 0.975, CH$_2$Cl$_2$).

(4): ((R)-2-{(S)-2-[2-((E)-(S)-3-Hydroxy-7-tritylsulfanyl-hept-4-enoylamino)-2-methyl-propionylamino]-3-tritylsulfanyl-propionylamino}-3-methyl-butyrylamino)-acetic acid methyl ester Et$_2$NH (4 mL) was added to 2 (410 mg, 0.49 mmol) in MeCN (36 mL) at rt under Ar(g). After 1 h 15 min of stirring, the solvent was removed under reduced pressure then the residue was re-dissolved and evaporated with MeCN (4×20 mL) and hexane (2×20 mL). The crude product was dried under high vacuum at least 3 h before being used in the next step. N,N-Diisopropylethylamine (0.214 mL, 1.22 mmol) was added to a solution of 3 (226 mg, 0.54 mmol) and PyBOP (279 mg, 0.54 mmol) in CH$_2$Cl$_2$ (40 mL) at 0° C. under Ar(g). After 10 min of stirring, the mixture was transferred to the crude amine resulting of the deprotection of 2 dissolved in MeCN (40 mL) at 0° C. under Ar(g), then the reaction mixture was left to warm to rt. After 2.5 h, the reaction mixture was concentrated under reduced pressure. The residue was further purified by silica gel column chromatography eluting with EtOAc to yield 4 as a white solid (257 mg, 51%).

$^1$H NMR (400 MHz, 9/1 CDCl$_3$/CD$_3$OD) $\delta_H$: 7.09-7.44 (m, 33H) 5.39 (dt, J=15.4, 5.9 Hz, 1H) 5.30 (dd, J=15.3, 5.9 Hz, 1H) 4.21-4.29 (m, 1H) 4.19 (d, J=6.0 Hz, 1H) 3.95-3.99 (m, 1H) 3.92 (d, J=17.6 Hz, 1H) 3.61 (s, 3H) 2.69 (d, J=8.0 Hz, 1H) 2.66 (d, J=8.0 Hz, 1H) 2.48 (d, J=4.9 Hz, 1H) 2.45 (d, J=5.0 Hz, 1H) 2.33-2.42 (m, 2H) 2.29 (quin, J=6.7 Hz, 2H) 2.11-2.22 (m, 4H) 1.40 (s, 3H) 1.32 (s, 3H) 0.92 (d, J=1.4 Hz, 3H) 0.90 (d, J=1.5 Hz, 3H). MS (ES): 1042.0 (100%, [M+Na]$^+$).

(5): (6R,9S,16R)-6-Isopropyl-12,12-dimethyl-16-((E)-4-tritylsulfanyl-but-1-enyl)-9-tritylsulfanylmethyl-1-oxa-4,7,10,13-tetraaza-cyclohexadecane-2,5,8,11,14-pentaone LiOH (9 mg, 0.37 mmol) in water (2 mL) was added to 4 (255 mg, 0.25 mmol) in THF (8 mL) at 0° C. After 45 minutes of stirring at 0° C. the reaction mixture was neutralized with aqueous 0.5M HCl, then brine (40 mL) and EtOAc (40 mL) were added. The phases were separated and the aqueous phase was extracted with EtOAc (20 mL). The organic extracts were combined, dried over MgSO$_4$, filtered then concentrated under reduced pressure. The crude product was dried under high vacuum before being used in the next step. The crude carboxylic acid in CH$_2$Cl$_2$/THF (200 mL, 12:1 v/v) was added dropwise over a period of 3 h to 2-methyl-6-nitrobenzoic anhydride (103 mg, 0.30 mmol) and 4-(dimethylamino)pyridine (73 mg, 0.60 mmol) in CH$_2$Cl$_2$ (50 mL) at rt under Ar(g). After 15 h, the reaction mixture was concentrated under reduced pressure and the residue was purified by silica gel column chromatography eluting with CH$_2$Cl$_2$/isopropanol (100:2.5 then 100:5) to yield 5 as a white solid (117 mg, 47%).

$^1$H NMR (400 MHz, CDCl$_3$) $\delta_H$: 7.36-7.47 (m, 10H), 7.14-7.36 (m, 21H), 7.02 (d, J=10.0 Hz, 1H), 6.45 (d, J=4.6 Hz, 1H), 5.80-5.91 (m, 1H), 5.62 (dt, J=14.9, 6.7 Hz, 1H), 5.31-5.38 (m, 1H), 5.26 (ddd, J=10.7, 7.0, 3.9 Hz, 1H), 4.73 (dd, J=16.7, 10.0 Hz, 1H), 4.68 (dd, J=10.9, 3.8 Hz, 1H), 3.98-4.00 (m, 1H), 3.39 (dd, J=15.4, 1.3 Hz, 1H), 2.95 (dd, J=12.5, 7.3 Hz, 1H), 2.63-2.73 (m, 2H), 2.59 (dd, J=12.5, 4.3 Hz, 1H), 2.52 (dd, J=14.2, 3.9 Hz, 1H), 2.36 (dd, J=14.2, 10.9 Hz, 1H), 2.14-2.23 (m, 2H), 1.94-2.14 (m, 2H), 1.55 (s, 3H), 1.32 (s, 3H), 0.99 (t, J=8.0 Hz, 6H). MS (ES): 1009.8 (100%, [M+Na]$^+$).

Compound XXVII (E)-(1S,7R,10S)-7-Isopropyl-21,21-dimethyl-2-oxa-12,13-dithia-5,8,20,23-tetraaza-bicyclo[8.7.6]tricos-16-ene-3,6,9,19,22-pentaone Compound 5 (115 mg, 0.117 mmol) in CH$_2$Cl$_2$/CH$_3$OH (80 mL, 9:1, v/v) was added dropwise over a period of 30 min to I$_2$ (295 mg, 1.16 mmol) in CH$_2$Cl$_2$/CH$_3$OH (170 mL, 9:1, v/v) at rt under Ar(g). After 2 h of stirring, aqueous 0.1 M Na$_2$S$_2$O$_3$ (500 mL) and brine (150 mL) were added. The phases were separated then the aqueous phase was extracted with CH$_2$Cl$_2$ (2×40 mL) and EtOAc (2×40 mL). The organic phases were combined, dried over MgSO$_4$, filtered, and concentrated under reduced pressure. The residue was purified by silica gel column chromatography eluting with CH$_2$Cl$_2$/CH$_3$OH (100:1 to 100:5) to yield compound XXVII as a white solid (41 mg, 70%).

$^1$H NMR (400 MHz, 9/1 CDCl$_3$/CD$_3$OD) δ$_H$: 7.33 (d, J=7.7 Hz, 1H), 5.68-5.80 (m, 1H), 5.57-5.67 (m, 2H), 4.69 (ddd, J=10.0, 7.7, 4.0 Hz, 1H), 4.16 (d, J=17.4 Hz, 1H), 3.85 (d, J=17.3 Hz, 1H), 3.26 (dd, J=15.3, 10.0 Hz, 1H), 2.94-3.05 (m, 2H), 2.80-2.92 (m, 2H), 2.57-2.68 (m, 1H), 2.52-2.57 (m, 2H), 2.36-2.49 (m, 1H), 1.50 (s, 3H), 1.43 (s, 3H), 0.91 (t, J=6.8 Hz, 6H). $^{13}$C NMR (100 MHz, 9/1 CDCl$_3$/CD$_3$OD) δ$_C$: 174.88, 172.31, 170.57, 169.71, 168.18, 129.05, 129.02, 69.67, 64.93, 57.12, 55.47, 42.04, 39.73, 37.42, 31.72, 26.95, 26.37, 22.66, 20.38, 20.00. MS (ES): 523.4 (100%, [M+Na]$^+$), 1024.0 (70%, [2M+Na]$^+$).

Compound XXIX (E)-(1S,10S)-7-Isopropyl-21,21-cyclopropyl-2-oxa-12,13-dithia-5,8,20,23-tetraaza-bicyclo[8.7.6]tricos-16-ene-3,6,9,19,22-pentaone the flask was dried under high vacuum for 2 h. To a solution of Fmoc-cyclopropylamino acid (141 mg, 0.44 mmol, 1.1 eq) in MeCN (6 mL) at 0° C. was added PyBOP (227 mg 0.44 mmol, 1.1 eq) and N-ethyldiisopropylamine (173 μL, 0.99 mmol, 2.5 eq) under Ar(g). The crude amine, dissolved in CH$_2$Cl$_2$ (6 mL) was added to the mixture dropwise. The reaction mixture was then left to warm to rt overnight. The mixture was then concentrated in vacuo and the residue was further purified by silica gel column chromatography with hexane/EtOAc (1:3→0:1) to yield 2 as a white solid (344 mg, 98%).

$^1$H NMR (400 MHz, CDCl$_3$+10% MeOD) δ$_H$: 7.70 (d, J=7.5 Hz, 2H), 7.44-7.51 (m, 1H), 7.42 (d, J=7.4 Hz, 1H), 7.31-7.36 (m, 2H), 7.20-7.27 (m, 8H), 7.12-7.18 (m, 7H), 7.05-7.10 (m, 3H), 4.32 (dd, J=10.5, 6.8 Hz, 1H), 4.14-4.22 (m, 2H), 3.99-4.05 (m, 1H), 3.83-3.93 (m, 1H), 3.63 (s, 3H), 2.66-2.80 (m, 1H), 2.37-2.49 (m, 1H), 2.18-2.31 (m, 1H), 1.38-1.49 (m, 2H), 1.22-1.28 (m, 1H), 1.03-1.12 (m, 1H), 0.87-0.97 (m, 6H). MS (ES$^+$) 862.1 (100%, [M+Na]$^+$).

(4): [2-((S)-2-{[1-((E)-(S)-3-Hydroxy-7-tritylsulfanyl-hept-4-enoylamino)-cyclopropanecarbonyl]-amino}-3-tritylsulfanyl-propionylamino)-3-methyl-butyrylamino]-acetic acid methyl ester To a solution of 2 (344 mg, 0.41 mmol, 1 eq) in MeCN (9 mL) was added Et$_2$NH (0.9 mL, 10% v/v) dropwise at rt under

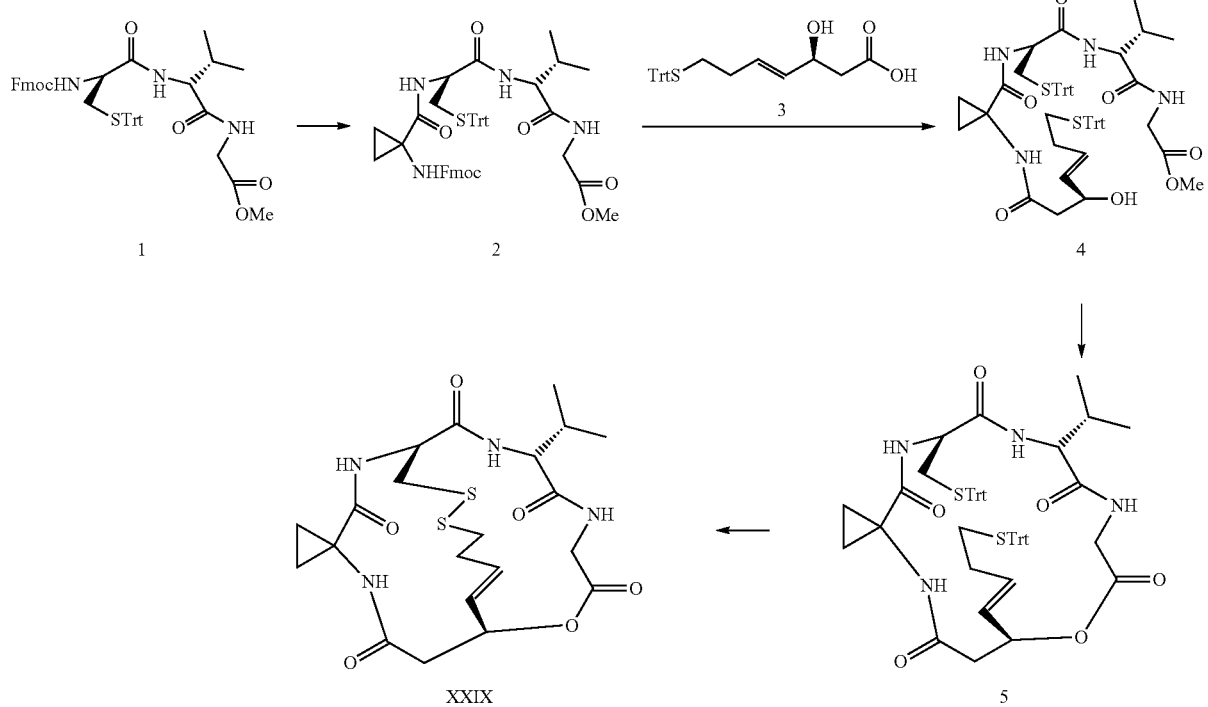

(2): [2-((S)-2-{([1-(9H-Fluoren-9-ylmethoxycarbonylamino)-cyclopropanecarbonyl]-amino}-3-tritylsulfanyl-propionylamino)-3-methyl-butyrylamino]-acetic acid methyl ester To a solution of 1 (300 mg, 0.40 mmol, 1 eq) in MeCN (8 mL) was added 0.8 mL of Et$_2$NH (10% v/v) dropwise at rt under Ar(g). The solution was stirred at rt for 2 h, then the solvent was removed in vacuo. The excess of amine was co-evaporated with MeCN (3×5 mL), then with a 1:5 mixture of CH$_2$Cl$_2$/hexane (10 mL). A white solid was obtained and Ar(g). The solution was stirred at rt for 2 h, then the solvent was removed in vacuo. The excess of amine was co-evaporated with MeCN (3×5 mL), then a 1:5 mixture of CH$_2$Cl$_2$/hexane (10 mL). A white solid was obtained and the flask was dried on the high-vacuum pump for 2 h. To a solution of □-hydroxy acid 3 (189 mg, 0.45 mmol, 1.1 eq) in MeCN (8 mL) at 0° C. was added PyBOP (235 mg, 0.45 mmol, 1.1 eq) and N-ethyldiisopropylamine (179 μL. 1.02 mmol, 2.5 eq) under Ar(g). The crude amine, dissolved in CH$_2$Cl$_2$ (8 mL) was added to the mixture dropwise. The reaction mixture was then left to warm to rt overnight. The mixture was then concentrated in vacuo and the residue was further purified by silica gel column chromatography with hexane/EtOAc (1:4) to yield 4 as a white solid (171 mg, 41%).

$^1$H NMR (400 MHz, CDCl$_3$+10% MeOD) δ$_H$: 7.31-7.38 (m, 8H), 7.28-7.30 (m, 3H), 7.06-7.25 (m, 22H), 5.36-5.45 (m, 1H), 5.32 (dd, J=15.6, 6.1 Hz, 1H), 4.26-4.33 (m, 1H), 4.03-4.13 (m, 2H), 3.62 (s, 3H), 2.55 (dd, J=12.7, 7.9 Hz, 1H), 2.46 (dd, J=12.4, 6.1 Hz, 1H), 2.07-2.26 (m, 6H), 1.96-2.06 (m, 3H), 1.49-1.57 (m, 1H), 1.25-1.33 (m, 1H), 0.92-1.00 (m, 1H), 0.88 (dd, J=6.8, 2.8 Hz, 6H), 0.75-0.80 (m, 1H). MS (ES$^+$) 1039.8 (100%, [M+Na]$^+$).

(5): (7S,16S)-13-Isopropyl-7-((E)-4-tritylsulfanyl-but-1-enyl)-16-tritylsulfanylmethyl-8-oxa-4,11,14,17-tetraaza-spiro[2.15]octadecane-5,9,12,15,18-pentaone To a solution of 4 (171 mg, 0.17 mmol, 1 eq) in THF (6 mL) at 0° C. was added a solution of LiOH (6.0 mg, 0.25 mmol, 1.5 eq) in H$_2$O (2 mL) dropwise. The mixture was stirred for 2 h, then quenched with 1N HCl (2 mL) and brine (10 mL). The organic layer was separated and the resulting aqueous layer was further extracted with EtOAc (2×15 mL) and CH$_2$Cl$_2$ (15 mL). The combined organic extracts were dried over MgSO$_4$ and the solvent was removed in vacuo. The resulting carboxylic acid was then dried under high vacuum for 2 h, To a solution of MNBA (69 mg, 0.21 mmol, 1.2 eq) and DMAP (49.3 mg, 0.40 mmol, 2.4 eq) in CH$_2$Cl$_2$ (150 mL) was added a solution of the crude carboxylic acid in CH$_2$Cl$_2$ (60 mL) and THF (10 mL) dropwise over 3 h. The reaction mixture was then left to stir at rt overnight. The solvent was then removed in vacuo and the residue was further purified by silica gel column chromatography with hexane/EtOAc (2:3) to yield 5 as a white solid (83 mg, 50%).

$^1$H NMR (400 MHz, CDCl$_3$) δ$_H$: 7.36-7.45 (m, 13H), 7.27-7.35 (m, 15H), 7.18-7.27 (m, 8H), 5.54-5.64 (m, 1H), 5.49 (dd, J=15.5, 7.2 Hz, 1H), 5.28-5.36 (m, 1H), 4.65 (dd, J=17.2, 9.6 Hz, 1H), 4.55 (dd, J=9.6, 3.8 Hz, 1H), 3.87-3.96 (m, 1H), 3.43-3.53 (m, 1H), 2.93 (dd, J=12.7, 7.2 Hz, 1H), 2.61-2.70 (m, 1H), 2.58 (dd, J=14.9, 4.7 Hz, 1H), 2.51 (dd, J=12.6, 4.5 Hz, 1H), 2.44 (dd, J=14.7, 8.5 Hz, 1H), 2.14-2.22 (m, 2H), 1.94-2.11 (m, 2H), 1.04-1.14 (m, 1H), 0.92-1.03 (m, 9H). MS (ES$^+$) 1008.2 (100%, [M+Na]$^+$).

Compound XXIX (E)-(1S,10S)-7-Isopropyl-21,21-cyclopropyl-2-oxa-12,13-dithia-5,8,20,23-tetraaza-bicyclo[8.7.6]tricos-16-ene-3,6,9,19,22-pentaone To a solution of I$_2$ (216 mg, 0.85 mmol, 10 eq) in CH$_2$Cl$_2$/MeOH (200 mL, 9:1) was added a solution of 5 (84 mg, 0.085 mmol, 1 eq) dropwise over 2 h at rt. The mixture was quenched with a solution of Na$_2$S$_2$O$_3$ (0.1 M, 200 mL) and brine (10 mL). The organic layer was separated and the resulting aqueous layer was further extracted with CH$_2$Cl$_2$ (2×50 mL) and EtOAc (50 mL). The combined organic extracts were dried over MgSO$_4$ and the solvent was removed in vacuo. Purification by silica gel column chromatography with CH$_2$Cl$_2$/MeOH (19:1→9:1) yielded compound XXIX (34.0 mg, 0.07 mmol, 76%) as a white solid.

$^1$H NMR (400 MHz, CDCl$_3$) δ$_H$: 7.11 (d, J=8.9 Hz, 1H), 6.57-6.70 (m, 1H), 6.03-6.16 (m, 1H), 5.65-5.85 (m, 2H), 5.01 (t, J=8.2 Hz, 1H), 4.18 (dd, J=17.6, 4.8 Hz, 1H), 4.07 (dd, J=17.6, 5.8 Hz, 1H), 3.61 (dd, J=13.7, 8.8 Hz, 1H), 3.26 (dd, J=10.0, 6.7 Hz, 1H), 2.93-3.03 (m, 1H), 2.77-2.91 (m, 5H), 2.67-2.75 (m, 2H), 2.57 (d, J=13.4 Hz, 1H), 1.35-1.44 (m, 1H), 1.14-1.22 (m, 1H), 0.89-1.00 (m, 8H). MS (ES$^+$) 521.3 (100%, [M+Na]$^+$).

Compound XXX (E)-(1S,10S)-7,7-Cyclopropyl-2-oxa-12,13-dithia-5,8,20,23-tetraaza-bicyclo[8.7.6]tricos-16-ene-3,6,9,19,22-pentaone

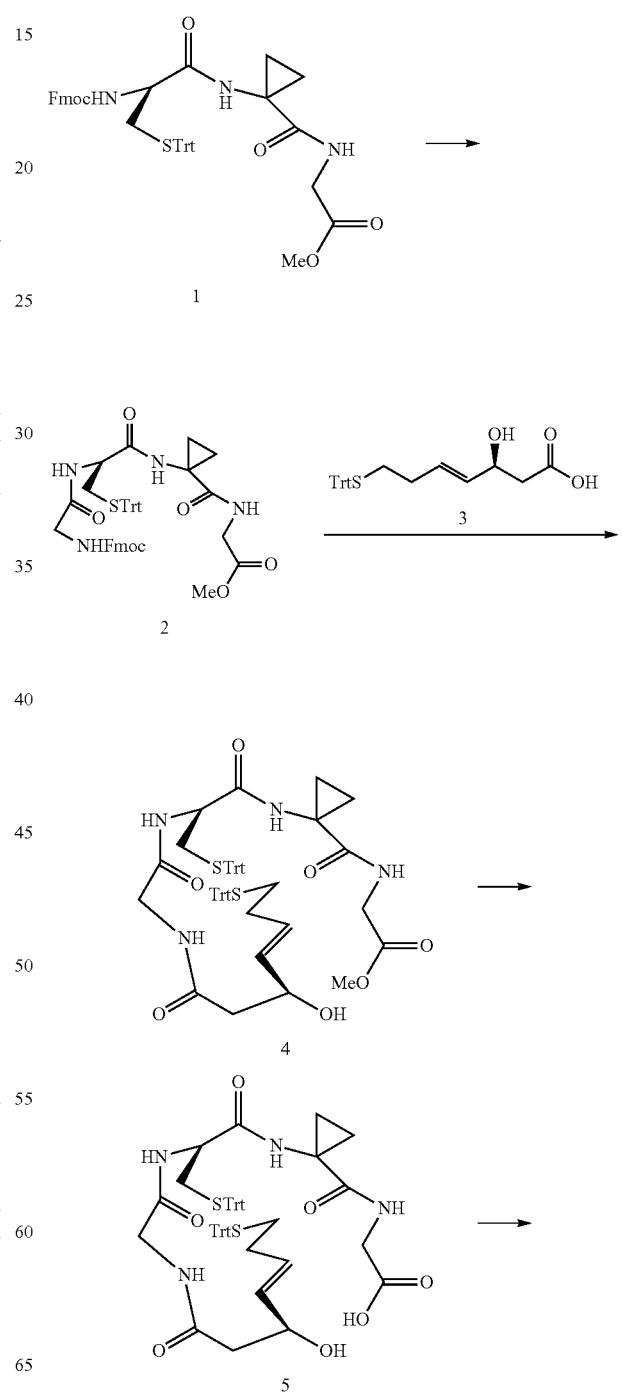

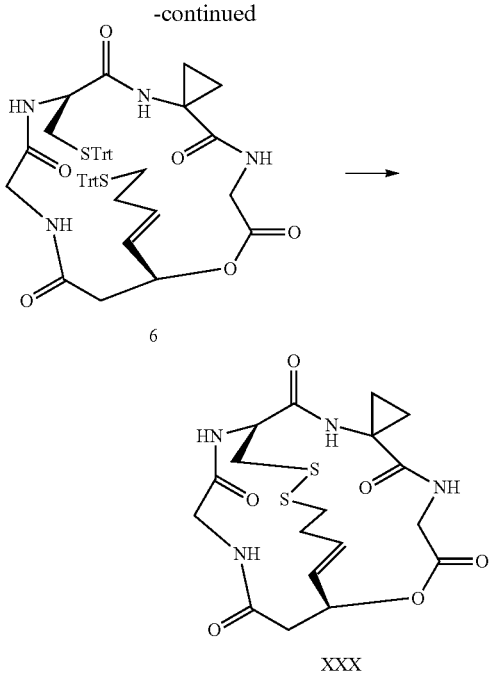

(2): {[1-((S)-2-Formylamino-3-tritylsulfanyl-propionylamino)-cyclopropanecarbonyl]-amino}-acetic acid methyl ester; compound with ethyl-carbamic acid 9H-fluoren-9-ylmethyl ester To a solution of 1 (310.5 mg, 0.420 mmol) in MeCN/CH$_2$Cl$_2$ (10 mL/19 mL) under Ar(g) was added diethylamine (2.9 mL, 10% v/v) and the reaction mixture stirred at rt for 1 h 50 min. The solvent was removed in vacuo, the crude mixture treated with MeCN (3×20 mL) and the solvent was removed under reduced pressure. The crude amine was then dried under high vacuum for 1 h. Then to a solution of PyBOP (234.9 mg, 0.451 mmol) and FmocGly-OH (133.86 mg, 0.450 mmol) in CH$_2$Cl$_2$ (20 mL) was added diisopropylethylamine (0.25 mL, 1.44 mmol) under Ar(g) with stirring for 3 min. A solution of the resultant deprotected amine of 1 in MeCN (20 mL) was added, and the resulting mixture was allowed to stir at rt for 16 h. The solvent was then removed in vacuo. Purification by flash column chromatography on silica (eluant 1:99-3:97-5:95 MeOH/CH$_2$Cl$_2$) gave a white solid. The material was washed with 1M HCl (aq), dried (MgSO$_4$) and concentrated in vacuo to give 2 (228.6 mg, 0.289 mmol, 68%) as a white solid.

$^1$H NMR (400 MHz, CDCl$_3$) $\delta_H$: 7.76 (d, J=7.53 Hz, 2H), 7.55 (t, J=6.78 Hz, 2H), 7.43-7.35 (m, 7H), 7.33-7.24 (m, 9H), 7.24-7.18 (m, 3H), 6.96 (br s, 1H), 6.50 (d, J=6.27 Hz, 1H), 5.70 (br s, 1H), 4.37 (dd, J=6.90, 1.63 Hz, 2H), 4.17 (t, J=6.84 Hz, 1H), 3.92 (m, 1H), 3.86-3.73 (m, 3H), 3.61 (s, 3H), 2.80 (m, 1H), 2.63 (dd, J=13.11, 5.84 Hz, 1H), 1.54 (q, J=3.97 Hz, 2H), 1.27 (s, 2H), 1.00 (d, J=2.51 Hz, 2H). MS (ES$^+$) 820.2 (100%, [M+Na]$^+$). R$_f$ 0.35 MeOH/CH$_2$Cl$_2$ (5:95).

(4): [(1-{(S)-2-[2-((E)-(S)-3-Hydroxy-7-tritylsulfanyl-hept-4-enoylamino)-acetylamino]-3-tritylsulfanyl-propionylamino}-cyclopropanecarbonyl)-amino]-acetic acid methyl ester To a solution of 2 (228.6 mg, 0.287 mmol) in MeCN (20 mL) under Ar(g) was added diethylamine (2.0 mL, 10% v/v) and the reaction mixture was allowed to stir at rt for 2 h. The solvent was removed in vacuo, the crude mixture treated with MeCN (3×20 mL) and the solvent was removed under reduced pressure. The crude amine was then dried under high vacuum. Then to a solution of PyBOP (150.37 mg, 0.289 mmol) and the chiral acid 3 (121.49 mg, 0.290 mmol) in CH$_2$Cl$_2$ (15 mL) was added diisopropylethylamine (0.18 mL, 1.03 mmol) under Ar(g). A solution of the resultant deprotected amine of 2 in MeCN (15 mL) was added and the reaction was allowed to stir at rt for 16 h. The solvent was then removed in vacuo and the solid formed was purified by flash column chromatography on silica (eluant 1:99-3:97-5:95 MeOH/CH$_2$Cl$_2$) to give 4 (157.3 mg, 0.161 mmol, 56%) as a white solid.

$^1$H NMR (300 MHz, CDCl$_3$) $\delta_H$: 7.45-7.32 (m, 11H), 7.32-7.16 (m, 20H), 7.11 (d, J=7.44 Hz, 1H), 6.94 (t, J=5.27 Hz, 1H), 5.52 (m, 1H), 5.39 (m, 1H), 4.39 (m, 1H), 4.06 (m, 1H), 3.98-3.52 (m, 7H), 2.78 (dd, J=12.57, 6.73 Hz, 1H), 2.57 (dd, J=12.53, 5.27 Hz, 1H), 2.45-2.15 (m, 4H), 2.11-1.99 (m, 2H), 1.56-1.46 (m, 2H), 1.43-1.35 (m, 2H), 1.09-0.94 (m, 2H). MS (ES$^+$) 998.2 (100%, [M+Na]$^+$). R$_f$ 0.26 MeOH/CH$_2$Cl$_2$ (5:95).

(5): [(1-{(S)-2-[2-((E)-(S)-3-Hydroxy-7-tritylsulfanyl-hept-4-enoylamino)-acetylamino]-3-tritylsulfanyl-propionylamino}-cyclopropanecarbonyl)-amino]-acetic acid To 4 (157.3 mg, 0.154 mmol) in THF (2.45 mL) at 0° C. was added LiOH (9.19 mg, 0.384 mmol) in water (0.65 mL) dropwise and the reaction was stirred for 55 min. The reaction mixture was then quenched with 1M HCl (aq) (10 mL) and diluted with water (10 mL). EtOAc (30 mL) was added the layers separated and the aqueous layer was extracted with EtOAc (3×30 mL). The organic layers were combined, washed with saturated brine (20 mL), separated, dried (MgSO$_4$) and concentrated in vacuo to give 5 (153 mg, 0.154 mmol, 100%) as a white solid, which was used without further purification [MS (ES$^-$) 959.2 (100%, [M−H]$^-$)].

(6): (6S,13S)-13-((E)-4-Tritylsulfanyl-but-1-enyl)-6-tritylsulfanylmethyl-14-oxa-4,7,10,17-tetraaza-spiro[2.15]octadecane-5,8,11,15,18-pentaone To a solution of MNBA (65.48 mg, 0.190 mmol) and DMAP (46.24 mg, 0.378 mmol) in CH$_2$Cl$_2$ (38 mL) was added dropwise a solution of the acid 5 (153 mg, 0.159 mmol) in CH$_2$Cl$_2$ (148 mL) over 3 h 55 min and the resulting mixture was then stirred overnight at rt. The reaction mixture was subsequently concentrated in vacuo to give an orange/yellow solid. Purification by column chromatography on silica (eluant 1:99-2:98 MeOH/CH$_2$Cl$_2$) gave 6 (68.2 mg, 0.0723 mmol, 45%) as a orange/yellow solid.

$^1$H NMR (400 MHz, CDCl$_3$) $\delta_H$: 7.55 (br s, 1H) 7.49 (d, J=7.40 Hz, 1H), 7.45-7.36 (m, 12H), 7.32-7.17 (m, 18H), 7.02 (br s, 1H), 5.57 (m, 1H), 5.50 (m, 1H), 5.36 (dd, J=15.50, 6.34 Hz, 1H), 4.08 (br s, 1H), 3.87 (d, J=13.68 Hz, 1H), 3.74 (m, 1H), 3.46 (dd, J=15.75, 3.70 Hz, 1H), 2.81 (dd, J=7.03 Hz, 1H), 2.60 (m, 1H), 2.53 (d, J=2.89 Hz, 1H), 2.49-2.40 (m, 2H), 2.19 (t, J=7.09 Hz, 2H), 2.07-1.99 (m, 2H), 1.87 (br s, 1H), 1.55 (br s, 2H), 1.08-0.97 (m, 2H). MS (ES$^+$) 966.1 (100%, [M+Na]$^+$). R$_f$ 0.27 (MeOH/CH$_2$Cl$_2$ (5:95).

Compound XXX (E)-(1S,10S)-7,7-Cyclopropyl-2-oxa-12,13-dithia-5,8,20,23-tetraaza-bicyclo[8.7.6]tricos-16-ene-3,6,9,19,22-pentaone To a solution of iodine (188.95 mg, 0.744 mmol) in CH$_2$Cl$_2$/MeOH (9:1) (248 mL) was added dropwise a solution of 6 (68.2 mg, 0.0723 mmol) in $CH_2Cl_2$/MeOH (9:1) (122.5 mL) over 30 min. The reaction mixture was then allowed to stir for a further 30 min after which time saturated sodium thiosulfate (10 mL) was added, and then water (30 mL). The layers were separated and the product was extracted with EtOAc (3×100 ml) and then with $CH_2Cl_2$ (100 mL), and dried ($MgSO_4$). The solvent was then removed in vacuo. Purification was performed by flash column chromatography on silica (eluant 5:95-7:93 MeOH/$CH_2Cl_2$) to give compound XXX (17.6 mg, 0.0386 mmol, 53%) as a white solid: $R_f$ 0.48 $CH_2Cl_2$/MeOH (9:1); $^1$H NMR (400 MHz, $CDCl_3$+ 10% MeOD) $\delta_H$: 8.45 (br s, 1H), 7.60 (br s, 1H), 7.32 (d, J=7.65 Hz, 1H), 6.93 (br s, 1H), 5.97 (m, 1H), 5.80-5.68 (m, 2H), 4.72 (m, 1H), 4.19 (m, 1H), 4.11-3.94 (m, 2H), 3.65 (m, 1H), 3.36 (m, 1H), 3.05-2.92 (m, 2H), 2.90-2.74 (m, 2H), 2.66 (br s, 2H), 1.70 (m, 1H), 1.29-1.16 (m, 2H), 1.09-0.96 (m, 2H). MS ($ES^+$) 479.8 (100%, $[M+Na]^+$).

Compound XXXI (E)-(1S,10S,21R)-7,7-Cyclopropyl-21-pyridin-3-ylmethyl-2-oxa-12,13-dithia-5,8,20,23-tetraaza-bicyclo[8.7.6]tricos-16-ene-3,6,9,19,22-pentaone

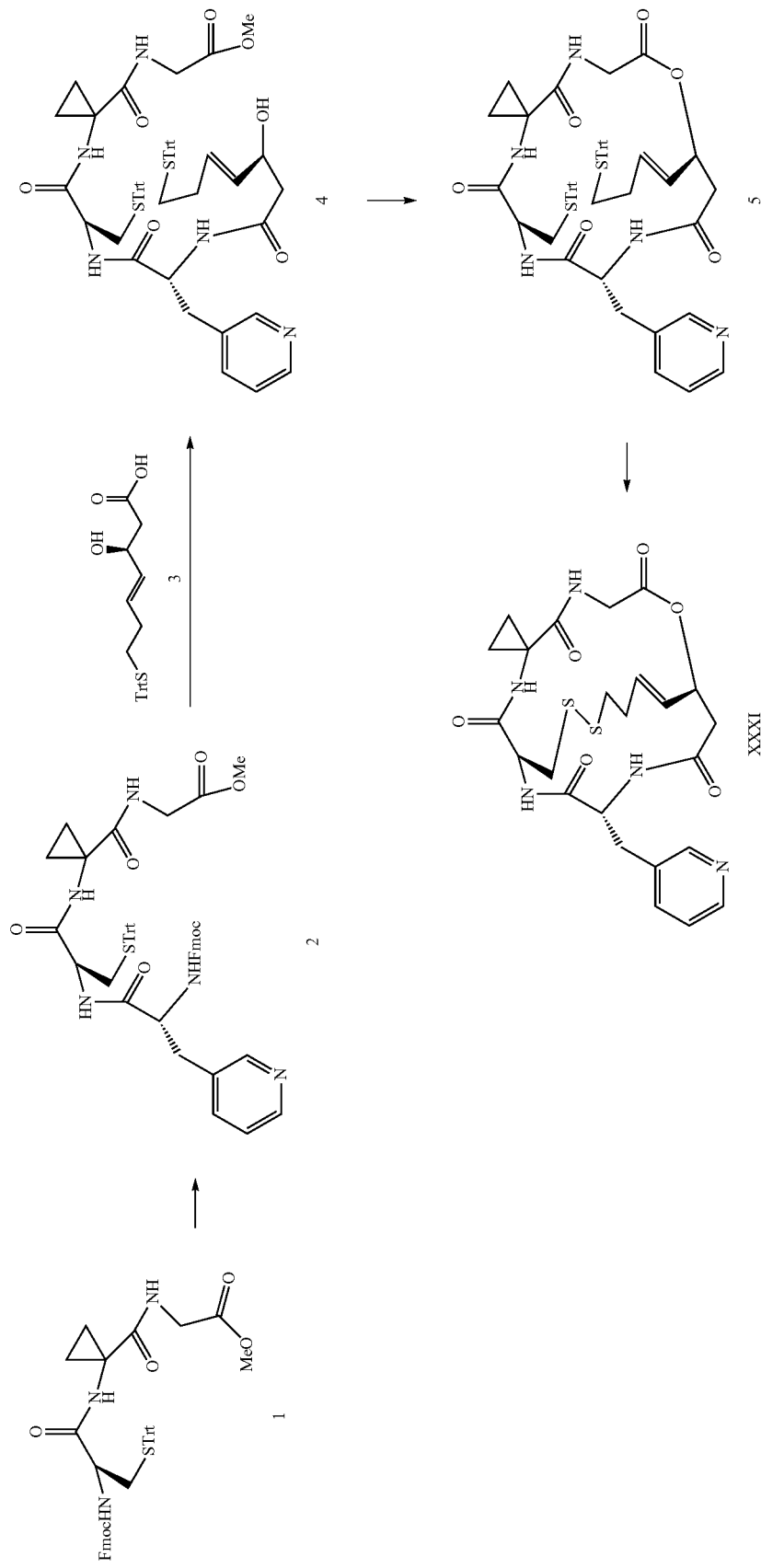

(2): (2-{(S)-2-[(R)-2-(9H-Fluoren-9-ylmethoxycarbonylamino)-3-pyridin-3-yl-propionylamino]-3-tritylsulfanyl-propionylamino}-2-methyl-propionylamino)-acetic acid methyl ester To a solution of 1 (300 mg, 0.40 mmol, 1 eq) in MeCN (8 mL) was added Et$_2$NH (0.8 mL, 10% v/v) dropwise at rt under Ar(g). The solution was stirred at rt for 2 h, then the solvent was removed in vacuo. The excess of amine was co-evaporated with MeCN (3×5 mL), then with a 1:5 mixture of CH$_2$Cl$_2$/hexane (10 mL). A white solid was obtained and the flask was dried under high vacuum for 2 h. To a solution of Fmoc-D-3-pyridinealanine (173 mg, 0.45 mmol, 1.1 eq) in MeCN (7 mL) at 0° C. was added PyBOP (232 mg, 0.45 mmol, 1.1 eq) and N-ethyldiisopropylamine (176 µL, 1.01 mmol, 2.5 eq) under Ar. The crude amine, dissolved in CH$_2$Cl$_2$ (6 mL) was added to the mixture dropwise. The reaction mixture was then left to warm to rt overnight. The mixture was then concentrated in vacuo and the residue was further purified by silica gel column chromatography using EtOAc/MeOH (1:0→19:1) as eluant to yield 2 as a yellow oil (316 mg, 88%).

$^1$H NMR (400 MHz, CDCl$_3$+10% MeOD) $\delta_H$: 8.32 (d, 2H), 7.74-7.79 (m, 1H), 7.70 (d, J=7.5 Hz, 2H), 7.55 (t, J=5.5 Hz, 2H), 7.43-7.48 (m, 2H), 7.33 (t, J=7.4 Hz, 2H), 7.12-7.29 (m, 18H), 4.17-4.36 (m, 3H), 4.07 (t, J=6.8 Hz, 1H), 3.67-3.72 (m, 3H), 3.61 (s, 3H), 2.98-3.09 (m, 1H), 2.76-2.92 (m, 1H), 2.41-2.59 (m, 2H), 1.41-1.53 (m, 2H), 0.87-1.05 (m, 2H). MS (ES$^+$) 910.7 (100%, [M+Na]$^+$).

(4): (2-{(S)-2-[(R)-2-((E)-(S)-3-Hydroxy-7-tritylsulfanyl-hept-4-enoylamino)-3-pyridin-3-yl-propionylamino]-3-tritylsulfanyl-propionylamino}-2-methyl-propionylamino)-acetic acid methyl ester To a solution of 2 (316 mg, 0.36 mmol, 1 eq) in MeCN (8 mL) was added Et$_2$NH (10% v/v) dropwise at rt under Ar(g). The solution was stirred at rt for 2 h, then the solvent was removed in vacuo. The excess of amine was co-evaporated with MeCN (3×5 mL), then with a 1:5 mixture of CH$_2$Cl$_2$/hexane (5 mL). A white solid was obtained and the flask was dried under high vacuum for 2 h. To a solution of β-hydroxy acid 3 (157 mg, 0.37 mmol, 1.1 eq) in MeCN (6 mL) at 0° C. was added PyBOP (204 mg, 0.37 mmol, 1.1 eq) and of N-ethyldiisopropylamine (155 µL, 0.89 mmol, 2.5 eq) under Ar(g). The crude amine, dissolved in CH$_2$Cl$_2$ (6 mL) was added to the mixture dropwise. The reaction mixture was then left to warm to rt overnight. The mixture was then concentrated in vacuo and the residue was further purified by silica gel column chromatography with CH$_2$Cl$_2$/MeOH (49:1→13:1) to yield 4 as a white solid (375 mg, 95%).

$^1$H NMR (400 MHz, CDCl$_3$) $\delta_H$: 8.42-8.49 (m, 2H), 7.67 (d, J=7.9 Hz, 1H), 7.38-7.43 (m, 7H), 7.33-7.37 (m, 5H), 7.27-7.31 (m, 8H), 7.25-7.27 (m, 4H), 7.18-7.24 (m, 7H), 7.07 (s, 1H), 6.67 (d, J=6.8 Hz, 1H), 5.45 (dt, J=15.4, 6.6 Hz, 1H), 5.34 (d, J=6.2 Hz, 1H), 4.52-4.60 (m, 1H), 4.29-4.37 (m, 1H), 4.01 (dd, J=17.9, 6.4 Hz, 1H), 3.85-3.92 (m, 1H), 3.66-3.76 (m, 3H), 3.60 (s, 3H), 3.18-3.23 (m, 1H), 3.00 (dd, J=14.6, 8.9 Hz, 1H), 2.70 (dd, J=12.9, 7.5 Hz, 1H), 2.63 (dd, J=12.9, 5.6 Hz, 1H), 2.26-2.32 (m, 1H), 2.16-2.26 (m, 3H), 2.00-2.06 (m, 3H), 1.53-1.58 (m, 1H), 1.48-1.52 (m, 1H), 0.92-1.10 (m, 2H). MS (ES$^+$) 1089.4 (100%, [M+Na]$^+$).

(5): (9S,12R,16S)-6,6-Cyclopropyl-12-pyridin-3-ylmethyl-16-((E)-4-tritylsulfanyl-but-1-enyl)-9-tritylsulfanylmethyl-1-oxa-4,7,10,13-tetraaza-cyclohexadecane-2,5,8,11,14-pentaone To a solution of 4 (375 mg, 0.35 mmol, 1 eq) in THF (15 mL) at 0° C. was added a solution of LiOH (12.3 mg, 0.51 mmol, 1.5 eq) in H$_2$O (3 mL) dropwise. The mixture was stirred for 2 h, then quenched with 1N HCl (4 mL) and brine (10 mL). The organic layer was separated and the resulting aqueous layer was further extracted with EtOAc (2×15 mL) and CH$_2$Cl$_2$ (15 mL). The combined organic extracts were dried over MgSO$_4$ and the solvent was removed in vacuo. The resulting carboxylic acid was then dried under high vacuum for 2 h. To a solution of MNBA (141 mg, 0.41 mmol, 1.2 eq) and DMAP (100.2 mg, 0.82 mmol, 2.4 eq) in CH$_2$Cl$_2$ (350 mL) was added a solution of the crude carboxylic acid in CH$_2$Cl$_2$ (150 mL) and THF (20 mL) dropwise over 3 h. The reaction mixture was then left to stir at rt overnight. The solvent was then removed in vacuo and the residue was further purified by silica gel column chromatography, eluting with CH$_2$Cl$_2$/MeOH (24:1) to yield 5 as a white solid (357 mg, 96%).

$^1$H NMR (400 MHz, CDCl$_3$) $\delta_H$: 8.39-8.46 (m, 2H), 8.06 (d, J=7.5 Hz, 1H), 7.31-7.43 (m, 15H), 7.13-7.26 (m, 17H), 6.79 (d, J=7.5 Hz, 1H), 6.71-6.77 (m, 1H), 5.41-5.57 (m, 2H), 5.30 (dd, J=15.6, 6.6 Hz, 1H), 4.65-4.75 (m, 1H), 4.20 (dd, J=16.4, 7.4 Hz, 1H), 3.72 (dd, J=16.8, 3.9 Hz, 1H), 2.88 (dd, J=14.2, 9.0 Hz, 1H), 2.72-2.83 (m, 1H), 2.42-2.52 (m, 1H), 2.32-2.40 (m, 1H), 2.13-2.19 (m, 3H), 1.96-2.03 (m, 5H), 1.39-1.52 (m, 3H), 1.01-1.10 (m, 1H). MS (ES$^+$) 1057.4 (100%, [M+Na]$^+$).

Compound XXXI

(E)-(1S,10S,21R)-7,7-Cyclopropyl-21-pyridin-3-ylmethyl-2-oxa-12,13-dithia-5,8,20,23-tetraaza-bicyclo[8.7.6]tricos-16-ene-3,6,9,19,22-pentaone To a solution of I$_2$ (877 mg, 3.46 mmol, 10 eq) in CH2CL2: MeOH (1.0 L, 9:1) was added a solution of 5 (357 mg, 0.35 mmol, 1 eq) dropwise over 2 h at rt. The mixture was quenched with a solution of Na$_2$S$_2$O$_3$ (0.1 M, 300 mL) and brine (10 mL). The organic layer was separated and the resulting aqueous layer was further extracted with extracted with CH$_2$Cl$_2$ (2×50 mL) and EtOAc (50 mL). The combined organic extracts were dried over MgSO$_4$ and the solvent was removed in vacuo. Purification by silica gel column chromatography with CH$_2$Cl$_2$/MeOH (16:1→12:1) yielded compound XXXI (45.0 mg, 24%) as a white solid.

$^1$H NMR (400 MHz, CDCl$_3$+10% MeOD) $\delta_H$: 8.40 (br. s., 2H), 7.66 (d, J=8.0 Hz, 1H), 7.52-7.58 (m, 2H), 7.31 (dd, J=7.7, 5.0 Hz, 1H), 6.89-6.95 (m, 1H), 5.82-5.92 (m, 1H), 5.70 (d, J=16.5 Hz, 1H), 5.63-5.68 (m, 1H), 4.63 (ddd, J=11.2, 7.5, 3.9 Hz, 1H), 4.52 (dd, J=9.7, 4.9 Hz, 1H), 4.24 (dd, J=18.5, 5.9 Hz, 1H), 3.92 (dd, J=18.5, 2.6 Hz, 1H), 3.19-3.31 (m, 2H), 2.94-3.09 (m, 3H), 2.80-2.92 (m, 1H), 2.59-2.71 (m, 3H), 1.71-1.78 (m, 1H), 1.21-1.27 (m, 2H), 0.94-1.03 (m, 2H). MS (ES$^+$) 570.6 (100%, [M+Na]$^+$).

85

Compound XXXII (E)-(1S,10S,21R)-21-(3-Chloro-benzyl)-7,7-cyclo-propyl-2-oxa-12,13-dithia-5,8,20,23-tetraaza-bicyclo[8.7.6]tricos-16-ene-3,6,9,19,22-pentaone

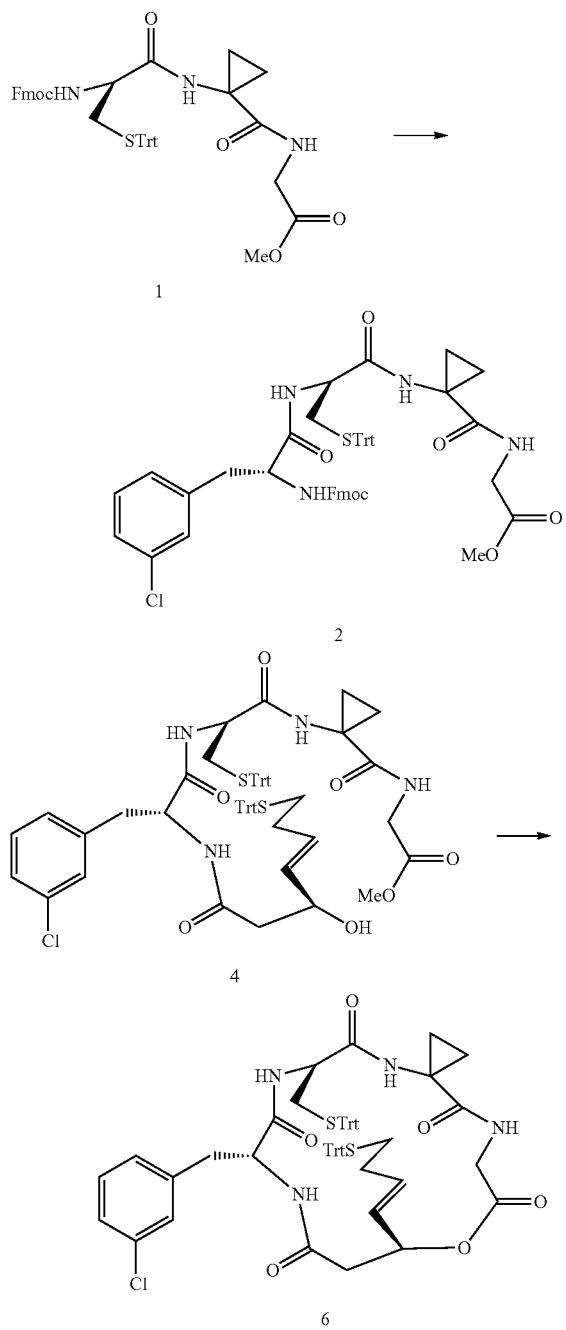

(2) [(1-{(S)-2-[(R)-3-(3-Chloro-phenyl)-2-(9H-fluoren-9-ylmethoxycarbonylamino)-propionylamino]-3-tritylsulfanyl-propionylamino}-cyclopropanecarbonyl)-amino]-acetic acid methyl ester To a solution of 1 (299.75 mg, 0.405 mmol) in MeCN/CH₂Cl₂ (10 mL/20 mL) under Ar(g) was added diethylamine (2.5 mL, 8.3% v/v) and the reaction mixture stirred at rt for 2 h 20 min. The solvent was removed in vacuo, was treated with MeCN (3×25 mL) and the solvent was then removed under reduced pressure. The crude amine was then dried under high vacuum for 2 h. Then to a solution of PyBOP (222.4 mg, 0.427 mmol) and Fmoc-D 3-chloroPhe-OH (179.94 mg, 0.425 mmol) in CH₂Cl₂ (15 mL) was added diisopropylethylamine (0.22 mL, 1.26 mmol) under Ar(g) with stirring for 2 min at 0° C. A solution of the resultant deprotected amine of 1 in MeCN (15 mL) was added and the reaction mixture was allowed to stir at rt for 16 h. Purification was then carried out by flash column chromatography on silica (eluant 4:6-6:4-7:3 EtOAc/Hexane) which gave 2 (201.6 mg, 0.219 mmol, 54%) as a white solid.

¹H NMR (400 MHz, CDCl₃) δ_H: 7.74 (d, J=7.40 Hz, 2H), 7.48 (d, J=7.53 Hz, 2H), 7.41-7.11 (m, 23H), 7.04 (br s, 1H), 4.38 (m, 1H), 4.30-4.22 (m, 2H), 4.11 (m, 1H), 3.79 (br s, 1H), 3.65 (s, 2H), 3.64-3.58 (m, 2H), 3.02 (br s, 1H), 2.88 (br s, 1H), 2.61 (br s, 2H), 1.51 (br s, 2H), 0.95 (br s, 2H). MS (ES⁺) 943.0 (100%, [M+Na]⁺). R_f 0.35 CH₂Cl₂/MeOH (95:5).

(4): [(1-{(S)-2-[(R)-3-(3-Chloro-phenyl)-2-((E)-(S)-3-hydroxy-7-tritylsulfanyl-hept-4-enoylamino)-propionylamino]-3-tritylsulfanyl-propionylamino}-cyclopropanecarbonyl)-amino]-acetic acid methyl ester To a solution of 2 (200 mg, 0.217 mmol) in MeCN/CH₂Cl₂ (10 mL/5 mL) under Ar(g) was added diethylamine (1.0 mL, 7% v/v) and the reaction mixture was allowed to stir at rt for 1 h 30 min. The solvent was removed in vacuo, was treated with MeCN (4×20 mL) and the solvent was then removed under reduced pressure. The crude amine was dried under high vacuum. To a solution of PyBOP (121.7 mg, 0.234 mmol) and the chiral acid 3 (105.4 mg, 0.252 mmol) in CH₂Cl₂ (15 mL) was added diisopropylethylamine (0.13 mL, 0.746 mmol) under Ar(g). A solution of the resultant deprotected amine in MeCN (15 mL) was added, and the reaction was allowed to stir at rt for 16 h. The solvent was then removed in vacuo and the crude product purified by flash column chromatography on silica (eluant 1:1-7:3 EtOAc/Hexane) to give 4 (190 mg, 0.173 mmol, 80%) as a white solid.

¹H NMR (400 MHz, CDCl₃+10% MeOD) δ_H: 7.37-7.10 (m, 37H), 7.01 (d, J=7.03 Hz, 1H), 5.42 (m, 1H), 5.28 (m, 1H), 4.44 (m, 1H), 4.24 (m, 1H), 3.85-3.67 (m, 3H), 3.59 (s, 3H), 3.37 (s, 1H), 3.33 (dt, J=3.17, 1.62 Hz, 1H), 3.02 (d, J=5.14 Hz, 2H), 2.80 (dd, J=14.31, 8.78 Hz, 1H), 2.53 (dd, J=6.90, 2.01 Hz, 1H), 2.24-2.10 (m, 5H), 2.01 (q, J=7.19 Hz, 2H), 1.52-1.40 (m, 2H), 0.95 (d, J=2.76 Hz, 2H). MS (ES⁺) 1121.7 (100%, [M+Na]⁺). R_f 0.22 MeOH/CH₂Cl₂ (5:95).

(5): [(1-{(S)-2-[(R)-3-(3-Chloro-phenyl)-2-(E)-(S)-3-hydroxy-7-tritylsulfanyl-hept-4-enoylamino)-propionylamino]-3-tritylsulfanyl-propionylamino}-cyclopropanecarbonyl)-amino]-acetic acid To 4 (188.5 mg, 0.172 mmol) in THF (2.9 mL) at 0° C. was added LiOH (8.5 mg, 0.355 mmol) in water (0.70 mL) and the reaction was stirred for 1 h 30 min. The mixture was then quenched with 1M HCl (aq) (10 mL), diluted with water (10 mL) and EtOAc (30 mL) was added. The layers were separated and the product was extracted with EtOAc (3×25 mL); the organics were combined, washed with saturated brine (20 mL), dried (MgSO₄), and concentrated in vacuo to give the product 5 (182 mg, 98%) as a white solid. The product was used without further purification [MS (ES⁻) 1083.6 (100%, [M−H]⁻)].

(6): (6S,9R,13S)-9-(3-Chloro-benzyl)-13-((E)-4-tritylsulfanyl-but-1-enyl)-6-tritylsulfanylmethyl-14-oxa-4,7,10,17-tetraaza-spiro[2.15]octadecane-5,8,11,15,18-pentaone To a solution of MNBA (69.29 mg, 0.201 mmol) and DMAP (48.76 mg, 0.40 mmol) in CH₂Cl₂ (31 mL) was added dropwise a solution of the acid 5 (180 mg, 0.166 mmol) in CH₂Cl₂ (125 mL) over 3 h; the reaction mixture was subsequently stirred overnight at rt, and then concentrated in vacuo to give a brown solid. Purification by column chromatography on silica (eluant 0:1-0.5:99.5-1:99-1.5:98.5-2:98-3; 97 MeOH/CH₂Cl₂) gave 6 (70.0 mg, 0.0656 mmol, 40%) as a white solid.

¹H NMR (400 MHz, CDCl₃) δ_H: 7.41-7.35 (m, 10H), 7.31-7.03 (m, 23H), 6.96 (d, J=7.65 Hz, 1H), 6.82 (br s, 1H), 6.26 (br s, 1H), 5.61-5.52 (m, 1H), 5.44-5.32 (m, 2H), 4.39 (br s, 1H), 4.23 (dd, J=16.63, 7.47 Hz, 1H), 3.84-0.75 (m, 1H), 3.50 (s, 2H), 3.01 (br s, 1H), 2.97-2.90 (m, 1H), 2.88-2.79 (m, 2H), 2.71-2.78 (m, 1H), 2.52-2.39 (m, 2H), 2.26-2.16 (m, 2H), 2.05 (br s, 2H), 1.49 (d, J=4.02 Hz, 2H), 1.05 (dd, J=9.79, 3.64 Hz, 1H), 0.86 (dd, J=10.04, 3.89 Hz, 1H). MS (ES⁺) 1089.3 (100%, [M+Na]⁺). R_f 0.42 MeOH/CH₂Cl₂ (5:95).

Compound XXXII (E)-(1S,10S,21R)-21-(3-Chloro-benzyl)-7,7-cyclopropyl-2-oxa-12,13-dithia-5,8,20,23-tetraaza-bicyclo[8.7.6]tricos-16-ene-3,6,9,19,22-pentaone To a solution of iodine (171.3 mg, 0.155 mmol) in CH₂Cl₂/MeOH (9:1) (113.5 mL) was added dropwise a solution of 6 (70.0 mg, 0.0656 mmol) in CH₂Cl₂/MeOH (9:1) (228.9 mL) over 40 min. The reaction mixture was then allowed to stir for a further 50 min, after which time sodium thiosulfate (100 mL, 0.05 M) was added. The layers were separated and the product was extracted with EtOAc (3×65 mL) separated, the organic layers were combined, dried (MgSO₄) and the solvent was removed in vacuo. Purification was carried out by flash column chromatography on silica (eluant 1:99-2:98-3:97-4:96-5:95 MeOH/CH₂Cl₂) to give compound XXXII (17.6 mg, 0.0343 mmol, 32%) as a white solid.

¹H NMR (400 MHz, CDCl₃+10% MeOD) δ_H: 7.77 (d, J=3.89 Hz, 1H), 7.62 (s, 1H), 7.47 (d, J=7.53 Hz, 1H), 7.21 (dd, J=5.52, 1.76 Hz, 2H), 7.08 (m, 1H), 6.92 (br s, 1H), 5.84 (m, 1H), 5.70-5.61 (m, 2H), 4.64 (ddd, J=10.76, 7.31, 3.89 Hz, 1H), 4.48 (m, 1H), 4.18 (dd, J=18.45, 5.65 Hz, 1H), 3.94 (dd, J=18.45, 3.14 Hz, 1H), 3.37-3.29 (m, 2H), 3.17 (dd, J=14.68, 5.27 Hz, 1H), 3.04-2.95 (m, 2H), 2.90 (dd, J=15.50, 3.83 Hz, 1H), 2.85-2.71 (m, 2H), 2.66-2.57 (m, 3H), 1.71 (m, 1H), 1.21 (m, 1H), 0.98 (q, J=3.05 Hz, 2H). MS (ES⁺) 603.2 (100%, [M+Na]⁺). R_f 0.34 CH₂Cl₂/MeOH (94:6).

Compound XXXIII (E)-(1S,10S,21R)-21-Benzyl-7,7-cyclopropyl-2-oxa-12,13-dithia-5,8,20,23-tetraaza-bicyclo[8.7.6]tricos-16-ene-3,6,9,19,22-pentaone

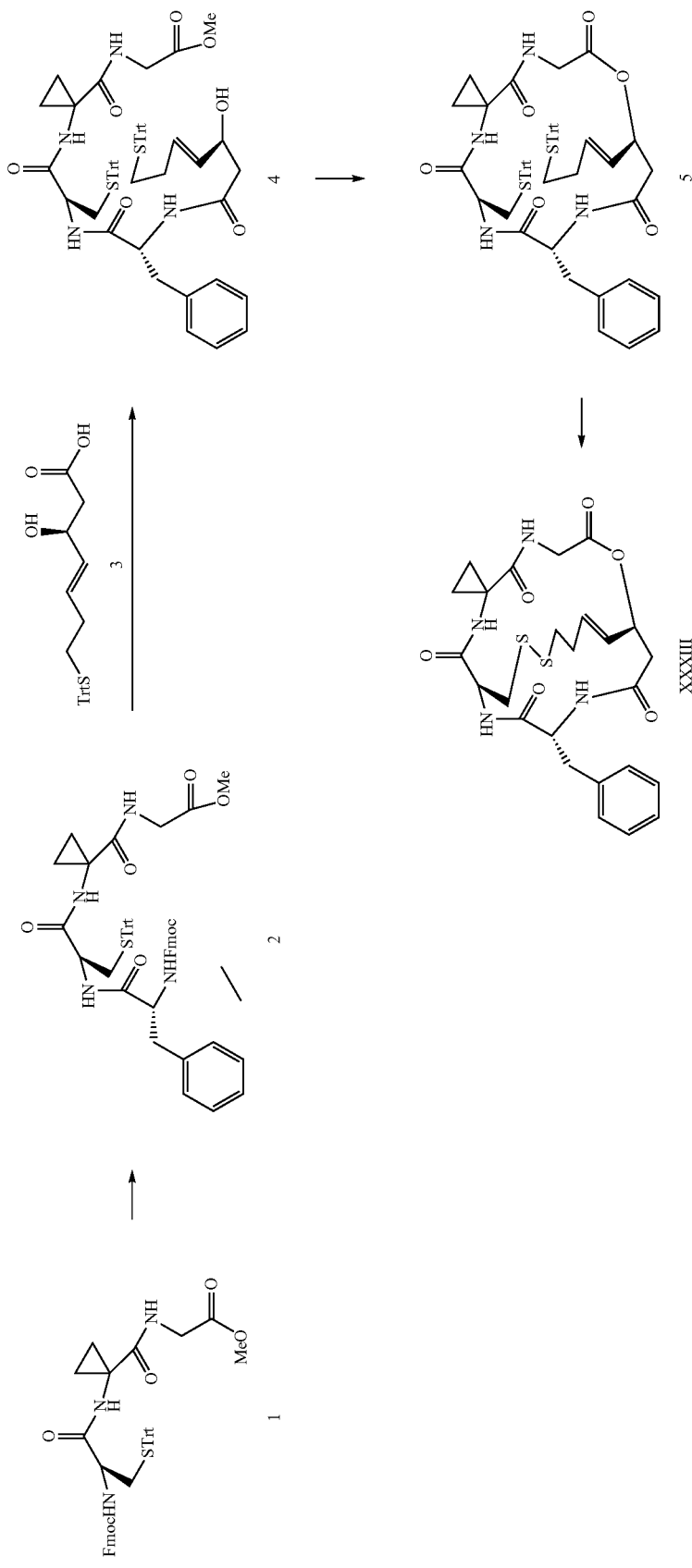

(2): [(1-{(S)-2-[(R)-2-(9H-Fluoren-9-ylmethoxycarbonylamino)-3-phenyl-propionylamino]-3-tritylsulfanyl-propionylamino}-cyclopropanecarbonyl)-amino]-acetic acid methyl ester To a solution of 1 (300 mg, 0.40 mmol, 1 eq) in MeCN (8 mL) was added Et$_2$NH (0.8 mL, 10% v/v) dropwise at rt under Ar(g). The solution was stirred at rt for 2 h, then the solvent was removed in vacuo. The excess of amine was co-evaporated with MeCN (3×5 mL), then with a 1:5 mixture of CH$_2$Cl$_2$/hexane (10 mL). A white solid was obtained and the flask was dried under high vacuum for 2 h. To a solution of Fmoc-D-Phenylalanine (173 mg, 0.45 mmol, 1.1 eq) in MeCN (7 mL) at 0° C. was added PyBOP (233 mg, 0.45 mmol, 1.1 eq) and 176 µL of N-ethyldiisopropylamine (1.01 mmol, 2.5 eq) under Ar(g). The crude amine, dissolved in CH$_2$Cl$_2$ (6 mL) was added to the mixture dropwise. The reaction mixture was then left to warm to rt overnight. The mixture was then concentrated in vacuo and the residue was further purified by silica gel column chromatography with hexane/EtOAc (1:2→0:1) to yield 2 as a white solid (294 mg, 82%).

$^1$H NMR (400 MHz, CDCl$_3$+10% MeOD) $\delta_H$: 7.70 (d, J=7.3 Hz, 2H), 7.45 (d, J=7.0 Hz, 2H), 7.34 (t, J=7.4 Hz, 2H), 7.05-7.29 (m, 25H), 4.15-4.37 (m, 3H), 4.08 (t, J=6.8 Hz, 2H), 3.66-3.74 (m, 3H), 3.60 (s, 3H), 2.80-3.06 (m, 2H), 2.38-2.56 (m, 2H), 1.41-1.51 (m, 2H), 0.88-0.99 (m, 2H). MS (ES$^+$) 909.2 (100%, [M+Na]$^+$).

(4): [(1-{(S)-2-[(R)-2-((E)-(S)-3-Hydroxy-7-tritylsulfanyl-hept-4-enoylamino)-3-phenyl-propionylamino]-3-tritylsulfanyl-propionylamino}-cyclopropanecarbonyl)-amino]-acetic acid methyl ester To a solution of 2 (294 mg, 0.33 mmol, 1 eq) in MeCN (7 mL) was added Et$_2$NH (0.7 mL, 10% v/v) dropwise at rt under Ar(g). The solution was stirred at rt for 2 h, then the solvent was removed in vacuo. The excess of amine was co-evaporated with MeCN (3×5 mL), then with a 1:5 mixture of CH$_2$Cl$_2$/hexane (5 mL). A white solid was obtained and the flask was dried under high vacuum for 2 h. To a solution of β-hydroxy acid 3 (145 mg, 0.35 mmol, 1.1 eq) in MeCN (5 mL) at 0° C. was added PyBOP (189 mg, 0.36 mmol, 1.1 eq) and N-ethyldiisopropylamine (143 µL, 0.83 mmol, 2.5 eq) under Ar(g). The crude amine, dissolved in CH$_2$Cl$_2$ (5 mL) was added to the mixture dropwise. The reaction mixture was then left to warm to rt overnight. The mixture was then concentrated in vacuo and the residue was further purified by silica gel column chromatography with hexane/EtOAc (2:3→0:1) to yield 4 as a white solid (305 mg, 87%).

$^1$H NMR (400 MHz, CDCl$_3$+10% MeOD) $\delta_H$: 7.49 (s, 1H), 7.33-7.39 (m, 7H), 7.28-7.33 (m, 4H), 7.12-728 (m, 27H), 5.39-5.49 (m, 1H), 5.26-5.35 (m, 1H), 4.27 (q, J=6.3 Hz, 1H), 3.86 (t, J=6.8 Hz, 1H), 3.72 (d, J=5.9 Hz, 2H), 3.62 (s, 3H), 3.05 (dd, 1H), 2.85 (dd, J=14.1, 8.6 Hz, 1H), 2.57 (dd, J=12.4, 6.9 Hz, 1H), 2.50 (dd, J=12.3, 7.1 Hz, 1H), 2.22 (d, J=6.8 Hz, 2H), 2.16 (t, J=7.2 Hz, 2H), 1.97-2.07 (m, 2H), 1.39-1.52 (m, 2H), 0.94-1.03 (m, 2H). MS (ES$^+$) 1087.8 (100%, [M+Na]$^+$).

(5): (6S,9R,13S)-9-Benzyl-13-((E)-4-tritylsulfanyl-but-1-enyl)-6-tritylsulfanylmethyl-14-oxa-4,7,10,17-tetraaza-spiro[2.15]octadecane-5,8,11,15,18-pentaone To a solution of 4 (305 mg, 0.29 mmol, 1 eq) in THF (10 mL) at 0° C. was added a solution of LiOH (10.3 mg, 0.43 mmol, 1.5 eq) in H$_2$O (2 mL) dropwise. The mixture was stirred for 2 h, then quenched with 1N HCl (3 mL) and brine (10 mL). The organic layer was separated and the resulting aqueous layer was further extracted with EtOAc (2×15 mL) and (15 mL). The combined organic extracts were dried over MgSO$_4$ and the solvent was removed in vacuo. The resulting carboxylic acid was then dried on the high-vacuum pump for 2 h. To a solution of MNBA (118 mg, 0.34 mmol, 1.2 eq) and DMAP (84 mg, 0.69 mmol, 2.4 eq) in CH2CL2 (200 mL) was added a solution of the crude carboxylic acid in CH$_2$Cl$_2$ (130 mL) and THF (20 mL) dropwise over 3 h. The reaction mixture was then left to stir up at rt overnight. The solvent was then removed in vacuo and the residue was further purified by silica gel column chromatography with hexane/EtOAc (1:9→0:1) to yield 5 as a white solid (171 mg, 58%).

$^1$H NMR (400 MHz, CDCl$_3$+10% MeOD) $\delta_H$: 7.50 (br. s., 1H), 7.34-7.40 (m, 7H), 7.18-7.33 (m, 30H), 5.42-5.52 (m, 1H), 5.40 (d, J=16.5 Hz, 1H), 5.33-5.39 (m, 1H), 4.61 (m, 1H), 4.51 (m, 1H), 4.19 (m, 1H), 3.82 (m, 1H), 3.17-3.21 (m, 2H), 2.84-2.99 (m, 3H), 2.70-2.82 (m, 2H), 2.49-2.60 (m, 2H), 1.65-1.58 (m, 1H), 1.39-1.52 (m, 2H), 0.94-1.03 (m, 2H). MS (ES$^+$) 1056.7 (100%, [M+Na]$^+$).

Compound XXXIII

(E)-(1S,10S,21R)-21-Benzyl-7,7-cyclopropyl-2-oxa-12,13-dithia-5,8,20,23-tetraaza-bicyclo[8.7.6]tricos-16-ene-3,6,9,19,22-pentaone To a solution of I$_2$ (420 mg, 1.65 mmol, 10 eq) in CH$_2$Cl$_2$/MeOH (400 mL, 9:1) was added a solution of 5 (171 mg, 0.17 mmol, 1 eq) dropwise over 2 h at rt. The mixture was quenched with a solution of Na$_2$S$_2$O$_3$ (0.1 M, 200 mL) and brine (10 mL). The organic layer was separated and the resulting aqueous layer was further extracted with extracted with CH$_2$Cl$_2$ (2×50 mL) and EtOAc (50 mL). The combined organic extracts were dried over MgSO$_4$ and the solvent was removed in vacuo. Purification by silica gel column chromatography with CH$_2$Cl$_2$/MeOH (32:1→12:1) yielded compound XXXIII (73.0 mg, 81%) as a white solid.

$^1$H NMR (400 MHz, CDCl$_3$) $\delta_H$: 7.50 (s, 1H), 7.44 (d, J=7.7 Hz, 1H), 7.36-7.42 (m, 2H), 7.30-7.35 (m, 1H), 7.23 (d, J=6.9 Hz, 2H), 6.82 (t, J=3.9 Hz, 1H), 6.00 (d, J=3.8 Hz, 1H), 5.80-5.91 (m, 1H), 5.74 (d, J=5.6 Hz, 1H), 5.65 (dd, J=16.0, 1.2 Hz, 1H), 4.78 (ddd, J=10.0, 7.7, 4.0 Hz, 1H), 4.59 (dt, J=9.5, 4.7 Hz, 1H), 4.19 (dd, J=18.4, 5.0 Hz, 1H), 4.11 (dd, J=18.5, 4.0 Hz, 1H), 3.51 (dd, J=15.4, 10.0 Hz, 1H), 3.33 (dd, J=14.6, 5.0 Hz, 1H), 2.88-3.10 (m, 4H), 2.64-2.81 (m, 2H), 2.53-2.63 (m, 1H), 2.45 (d, J=13.3 Hz, 1H), 1.79 (ddd, J=10.2, 7.2, 4.4 Hz, 1H), 1.35 (ddd, J=10.2, 7.2, 4.0 Hz, 1H), 1.07-1.14 (m, J=10.2, 7.7, 4.7 Hz, 1H), 0.99-1.06 (m, J=10.2, 7.2, 3.9 Hz, 1H). MS (ES$^+$) 579.7 (100%, [M+Na]$^+$).

Compound XXXIV
(E)-(1S,10S,21R)-7-cyclopropyl-21-pyridin-4-ylmethyl-2-oxa-12,13-dithia-5,8,20,23-tetraaza-bicyclo[8.7.6]tricos-16-ene-3,6,9,19,22-pentaone
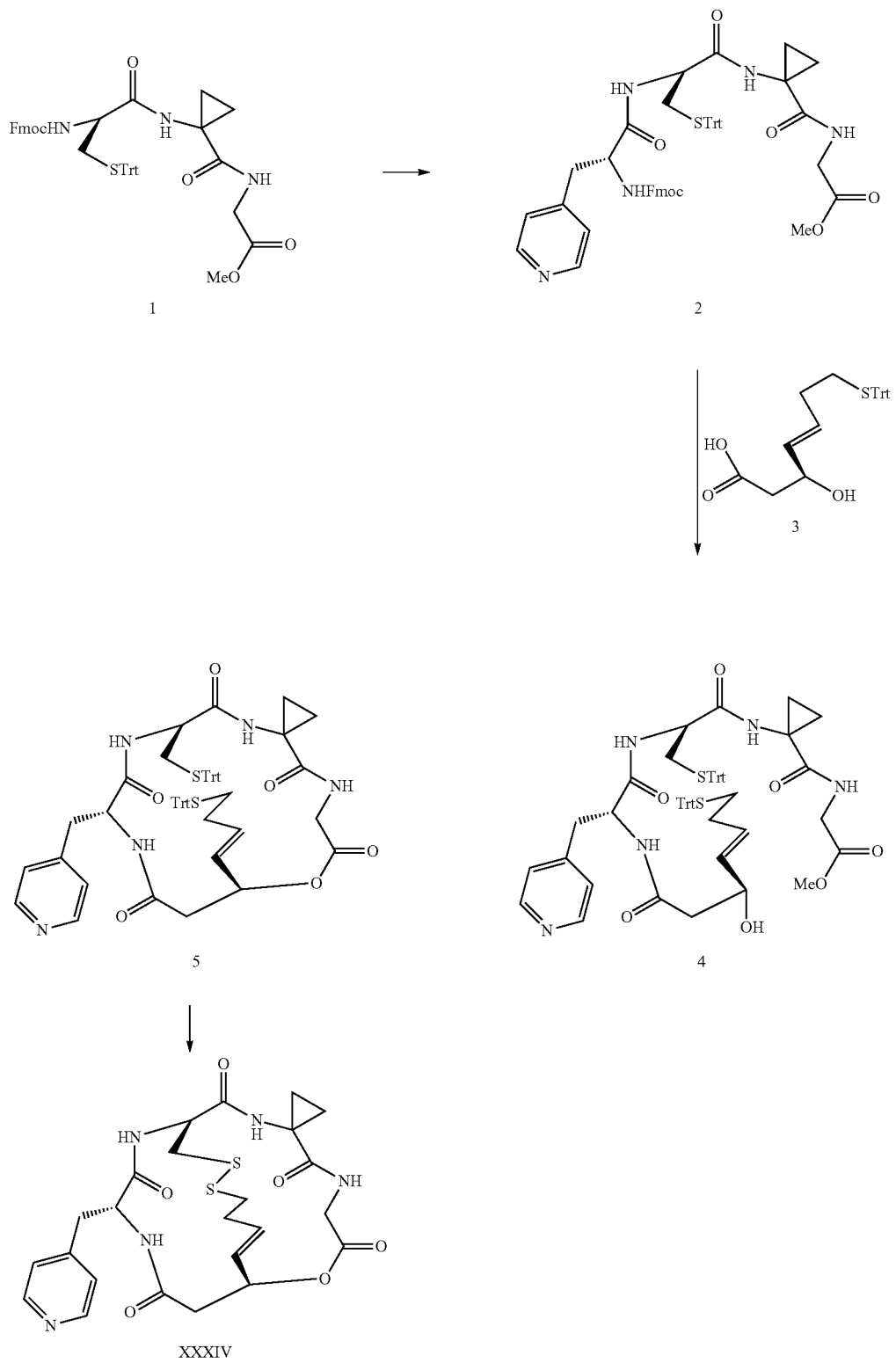

(2): [(1-{(S)-2-[(R)-2-(9H-Fluoren-9-ylmethoxycarbonylamino)-3-pyridin-4-yl-propionylamino]-3-tritylsulfanyl-propionylamino}-cyclopropanecarbonyl)-amino]-acetic acid methyl ester Et$_2$NH (2 mL) was added to ({1-[(S)-2-(9H-Fluoren-9-ylmethoxycarbonylamino)-3-tritylsulfanyl-propionylamino}-cyclopropanecarbonyl]-amino)-acetic acid methyl ester 1 (548 mg, 0.72 mmol) in MeCN (18 mL) at rt under Ar(g). After 3 h of stirring, the solvent was removed under reduced pressure, then the residue was re-dissolved, evaporated with MeCN (4×20 mL) and hexane (2×20 mL). The crude product was dried under high vacuum at least 3 h prior to being used in the next step. N,N-Diisopropylethylamine (0.26 mL, 1.50 mmol) was added to (R)-2-(9H-Fluoren-9-ylmethoxycarbonylamino)-3-pyridin-4-yl-propionic acid (254 mg, 0.65 mmol) and PyBOP (338 mg, 0.65 mmol) in CH$_2$Cl$_2$ (20 mL) at 0° C. under Ar(g). After 10 min of stirring, the mixture was transferred to the crude amine resulting of the deprotection of ({1-[(S)-2-(9H-Fluoren-9-ylmethoxycarbonylamino)-3-tritylsulfanyl-propionylamino]-cyclopropanecarbonyl}-amino)-acetic acid methyl ester 1, solubilised in MeCN (20 mL) at 0° C. under Ar(g). The reaction mixture was then allowed to warm to rt. After 17 h, the reaction mixture was concentrated under reduced pressure and the residue was purified by silica gel column chromatography eluting with EtOAc/CH$_3$OH (100:0 then 100:0.5 to 100:4) to yield 2 as a white solid (522 mg, 99%).

$^1$H NMR (400 MHz, 400 MHz, 9/1 CDCl$_3$/CD$_3$OD) δ$_H$: 8.46 (d, J=6.0 Hz, 1H), 7.69 (d, J=4.8 Hz, 1H), 7.64 (m, J=7.2 Hz, 2H), 7.38-7.51 (m, 2H), 7.24-7.34 (m, 10H), 7.05-7.23 (m, 15H), 4.33-4.39 (m, 1H), 4.21-4.31 (m, 2H), 3.65-3.78 (m, 2H), 3.62 (t, J=6.9 Hz, 1H), 3.54 (s, 3H), 2.96-3.14 (m, 2H), 2.44 (d, J=6.9 Hz, 1H), 1.36-1.49 (m, 2H), 1.34 (d, J=6.8 Hz, 1H), 1.29 (d, J=6.8 Hz, 1H), 0.80-0.96 (m, 2H). MS (ES): 888.7 (100%, [M+H]$^+$).

(4): [(1-{(S)-2-[(R)-2-((E)-(S)-3-Hydroxy-7-tritylsulfanyl-hept-4-enoylamino)-3-pyridin-4-yl-propionylamino]-3-tritylsulfanyl-propionylamino}-cyclopropanecarbonyl)-amino]-acetic acid methyl ester Et$_2$NH (2 mL) was added to 2 (523 mg, 0.59 mmol) in MeCN (18 mL) at rt under Ar(g). After 4 h of stirring the solvent was removed under reduced pressure then the residue was re-dissolved and evaporated with MeCN (4×20 mL) and hexane (2×20 mL). The crude product was dried under high vacuum at least 3 h prior to being used in the next step. N,N-Diisopropylethylamine (0.247 mL, 1.47 mmol) was added to a solution of 3 (272 mg, 0.65 mmol) and PyBOP (338 mg, 0.65 mmol) in CH$_2$Cl$_2$ (20 mL) at 0° C. under Ar(g). After 10 min of stirring, the mixture was transferred to the crude amine resulting of the deprotection of 2 dissolved in MeCN (10 mL) at 0° C. under Ar(g), then the reaction mixture was left to warm to rt. After 16.5 h, the reaction mixture was concentrated under reduced pressure. The residue was further purified by silica gel column chromatography eluting with CH$_2$Cl$_2$/CH$_3$OH (100:1 to 100:4) to yield 4 as a white solid (384 mg, 61%).

$^1$H NMR (400 MHz, CDCl$_3$) δ$_H$: 8.50 (d, J=6.5 Hz, 2H), 8.03 (d, J=6.9 Hz, 1H), 7.83-7.89 (m, 2H), 7.10-7.42 (m, 34H), 5.42 (dt, J=14.1, 6.1 Hz, 1H), 5.32 (dd, J=15.7, 6.3 Hz, 1H), 4.64-4.73 (m, 1H), 4.21-4.28 (m, 1H), 3.83 (d, J=17.7 Hz, 1H), 3.74 (d, J=17.8 Hz, 1H), 3.61-3.68 (m, 2H), 3.59 (s, 3H), 3.22-3.29 (m, 1H), 2.60 (d, J=7.4 Hz, 2H), 2.19-2.31 (m, 2H), 2.08-2.19 (m, 2H), 2.01 (q, J=6.9 Hz, 2H), 1.35-1.54 (m, 4H). MS (ES): 1066.9 (40%, [M+H]$^+$), 1088.8 (100%, [M+Na]$^+$).

(5): (6S,9R,13R)-9-Pyridin-4-ylmethyl-13-((E)-4-tritylsulfanyl-but-1-enyl)-6-tritylsulfanylmethyl-14-oxa-4,7,10,17-tetraaza-spiro[2.15]octadecane-5,8,11,15,18-pentaone LiOH (13 mg, 0.54 mmol) in water (2 mL) was added to 4 (384 mg, 0.36 mmol) in THF (8 mL) at 0° C. After 1.5 h of stirring at 0° C. the reaction mixture was neutralized with aqueous 0.5 M HCl then brine (50 mL) and EtOAc (50 mL) were added. The phases were separated and the aqueous phase was extracted with EtOAc (3×10 mL). The organic phases were combined, dried over MgSO$_4$, filtered then concentrated under reduced pressure. The crude product was dried under high vacuum before to be use for the next step. The crude carboxylic acid in CH$_2$Cl$_2$/THF (250 mL, 12:1 v/v) was added dropwise over a period of 3 h to 2-methyl-6-nitrobenzoic anhydride (149 mg, 0.43 mmol) and 4-(dimethylamino)pyridine (105 mg, 0.86 mmol) in CH$_2$Cl$_2$ (120 mL) at rt under Ar(g). After 19 h the reaction mixture was concentrated under reduced pressure and the residue was purified by silica gel column chromatography eluting with CH$_2$Cl$_2$/CH$_3$OH (100:2 then 100:10) to yield 5 as a white solid (203 mg, 54%).

$^1$H NMR (400 MHz, 9/1 CDCl$_3$/CD$_3$OD) δ$_H$: 8.37 (d, J=6.5 Hz, 2H), 7.75 (d, J=6.7 Hz, 2H), 6.90-7.22 (m, 33H), 5.34 (dt, J=14.8, 6.8 Hz, 1H), 5.08-5.21 (m, 2H), 4.50 (dd, J=10.8, 4.5 Hz, 1H), 3.84 (d, J=15.9 Hz, 1H), 3.57 (d, J=15.9 Hz, 1H), 3.22 (dd, J=14.1, 4.5 Hz, 1H), 3.15 (dd, J=9.4, 5.1 Hz, 1H), 2.59 (d, J=9.4 Hz, 1H), 2.56 (d, J=9.3 Hz, 1H), 2.45 (d, J=5.0 Hz, 1H), 2.42 (d, J=5.1 Hz, 1H), 2.38 (d, J=10.7 Hz, 1H), 2.34 (d, J=10.8 Hz, 1H), 2.02 (dd, J=14.8, 2.1 Hz, 1H), 1.89-1.96 (m, 2H), 1.74-1.83 (m, 2H), 1.24-1.35 (m, 2H), 1.19 (ddd, J=9.8, 7.9, 4.0 Hz, 2H). MS (ES): 1056.8 (100%, [M+Na]$^+$).

Compound XXXIV (E)-(1S,10S,21R)-7-cyclopropyl-21-pyridin-4-ylmethyl-2-oxa-12,13-dithia-5,8,20,23-tetraaza-bicyclo[8.7.6]tricos-16-ene-3,6,9,19,22-pentaone Compound 5 (201 mg, 0.19 mmol) in CH$_2$Cl$_2$/CH$_3$OH (143 mL, 9:1 v/v) was added dropwise over a period of 30 minutes to I$_2$ (502 mg, 1.94 mmol) in CH$_2$Cl$_2$/CH$_3$OH (297 mL, 9:1 v/v) at rt under Ar(g). After 3 h of stirring, aqueous 0.5 M Na$_2$S$_2$O$_3$ (500 mL) and brine (150 mL) were added. The phases were separated then the aqueous phase was extracted with CH$_2$Cl$_2$ (2×50 mL) and EtOAc (50 mL). The organic phases were combined, dried over MgSO$_4$, filtered then concentrated under reduced pressure. The residue was purified by silica gel column chromatography eluting with CH$_2$Cl$_2$/CH$_3$OH (100:3) to yield compound XXXIV as a white solid (2 mg, 2%).

$^1$H NMR (400 MHz, 9/1 CDCl$_3$/CD$_3$OD) δ$_H$: 8.88 (d, J=3.4 Hz, 1H), 8.49 (d, J=6.5 Hz, 2H), 8.07 (d, J=6.5 Hz, 1H), 7.96 (d, J=6.5 Hz, 2H), 7.51-7.59 (m, 1H), 6.86 (d, J=6.0 Hz, 1H), 5.83-5.94 (m, 1H), 5.75 (dd, J=18.6, 15.8 Hz, 1H), 5.53-5.65 (m, 1H), 4.82 (ddd, J=9.6, 4.0, 2.5 Hz, 1H), 4.51-4.58 (m, 1H), 4.48 (dt, J=8.8, 4.6 Hz, 1H), 4.25 (d, J=18.6 Hz, 1H), 4.14-4.21 (m, 1H), 3.79 (dd, J=14.8, 2.3 Hz, 1H), 3.76 (d, J=18.3 Hz, 1H), 3.70 (d, J=18.4 Hz, 1H), 3.48-3.59 (m, 2H), 3.39 (dd, J=15.6, 5.0 Hz, 2H), 3.23-3.33 (m, 2H), 1.55-1.70 (m, 2H), 1.16-1.25 (m, 2H). MS (ES): 570.8 (100%, [M+Na]⁺).

The invention claimed is:

1. A Compound of structure IX or X:

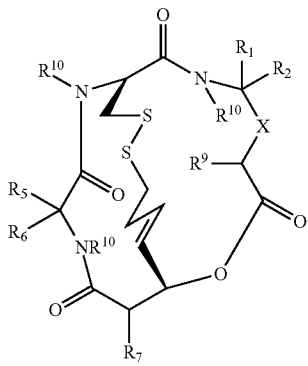

Structure IX

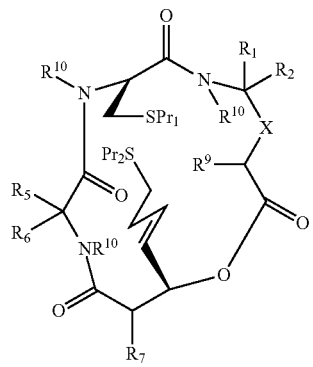

Structure X or a pharmaceutically acceptable salt thereof,
wherein:
X is —C(=O)N($R_{10}$)— or —CH(O$Pr_3$) —;
$R_7$, $R_9$ and $R_{10}$ are the same or different and represent hydrogen or an amino acid side chain moiety from either a natural or an unnatural amino acid;
$Pr_1$ and $Pr_2$ are the same or different and represent hydrogen or a thiol protecting group;
$Pr_3$ is hydrogen or an alcohol protecting group;
$R_1$, $R_2$, $R_5$ and $R_6$ are the same or different and represent hydrogen or an amino acid side chain moiety from either a natural or an unnatural amino acid, or $R_1$ and $R_2$ and/or $R_5$ and $R_6$, taken together with the carbon atom to which they are attached, form a spirocyclic moiety,
with the proviso that:
both $R_1$ and $R_2$ or both $R_5$ and $R_6$ are not hydrogen.

2. The compound according to claim 1, wherein $R_1$ and $R_2$ and/or $R_5$ and $R_6$, taken together with the carbon atom to which they are attached, form a cycloalkyl which has between 3 and 8 carbon atoms.

3. The compound according to claim 1, wherein the natural or unnatural amino acid side chain moiety is —CH₃ (Alanine), —CH(CH₃)₂ (Valine), —CH₂CH(CH₃)₂ (Leucine), —CH(CH₃)CH₂CH₃ (Isoleucine), —(CH₂)₄NH₂ (Lysine), —(CH₂)₃NHC(=NH)NH₂ (Arginine), —CH₂-(5-1H-imidazolyl) (Histidine), —CH₂CONH₂ (Asparagine), —CH₂CH₂CONH₂ (Glutamine), —CH₂COOH (Aspartic acid), —CH₂CH₂COOH (Glutamic acid), —CH₂-phenyl (Phenylalanine), —CH₂-(4-OH-phenyl) (Tyrosine), —CH₂-(3-1H-indolyl) (Tryptophan), —CH₂SH (Cysteine), —CH₂CH₂SCH₃ (Methionine), —CH₂OH (Serine), and —CH(OH)CH₃ (Threonine), —(CH₂)₂—C(O)—O—C(CH₃)₃ (glutamic acid t-butyl ester), —(CH₂)₄—NH—C(O)—O—C(CH₃)₃ ($N_\epsilon$-(tert-butoxycarbonyl)-lysine), —(CH₂)₃—NH—C(O)NH₂ (citrulline), —CH₂—CH₂OH (homoserine) and —(CH₂)₃NH₂ (ornithine), —H(Glycine), $C_1$-$C_6$ alkyl, $C_2$-$C_6$ alkenyl, $C_2$-$C_6$ alkynyl, aryl or a saturated or unsaturated heterocycle which can be functionalized or unfunctionalized.

4. The compound according to claim 3, wherein the natural or unnatural amino acid side chain moiety is —H (Glycine), —CH₃ (Alanine), —CH(CH₃)₂ (Valine), —CH₂CH(CH₃)₂ (Leucine), —CH(CH₃)CH₂CH₃ (Isoleucine), —(CH₂)₄NH₂ (Lysine), —(CH₂)₃NHC(=NH)NH₂ (Arginine), —CH₂-(5-1H-imidazolyl) (Histidine), —CH₂CONH₂ (Asparagine), —CH₂CH₂CONH₂ (Glutamine), —CH₂COOH (Aspartic acid), —CH₂CH₂COOH (Glutamic acid), —CH₂-phenyl (Phenylalanine), —CH₂-(4-OH-phenyl) (Tyrosine), —CH₂-(3- 1H-indolyl) (Tryptophan), —CH₂SH (Cysteine), —CH₂CH₂SCH₃ (Methionine), —CH₂OH (Serine), or —CH(OH)CH₃ (Threonine).

5. The compound according to claim 1, wherein X is —C(=O)N($R_{10}$)—.

6. The compound according to claim 5, which has one of Structures shown below:

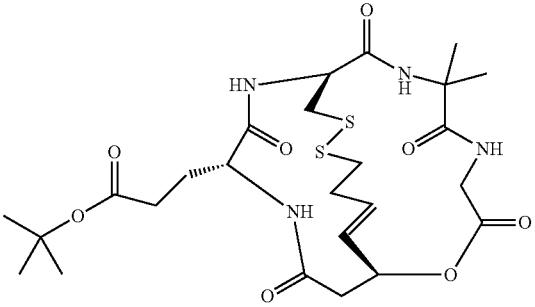

Compound XIV

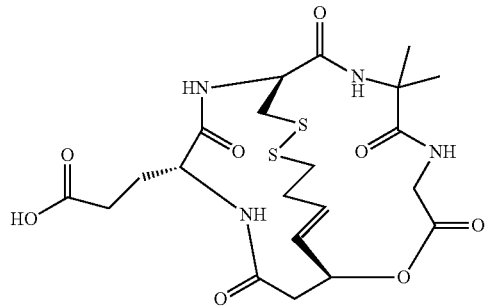

Compound XV

Compound XVI
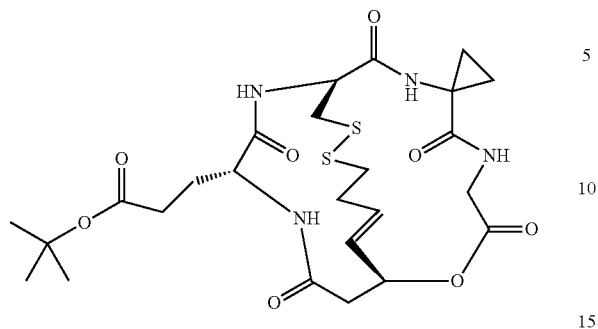
Compound XVII
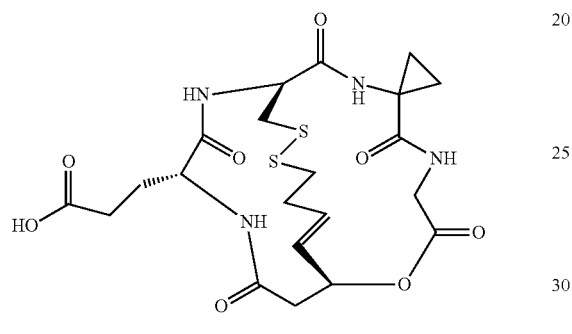
Compound XVIII
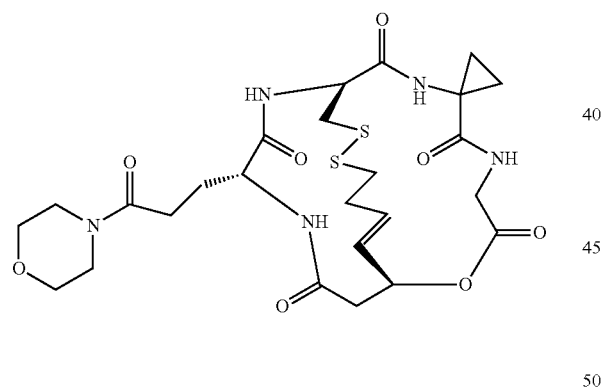
Compound XIX
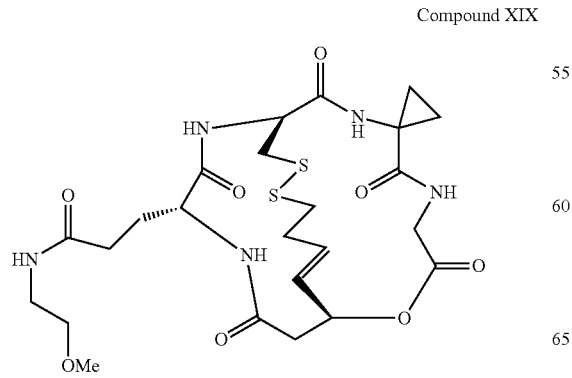
Compound XX
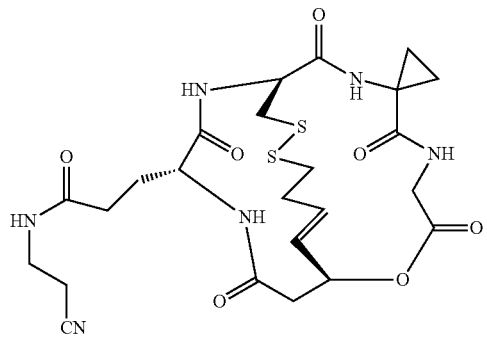
Compound XXI
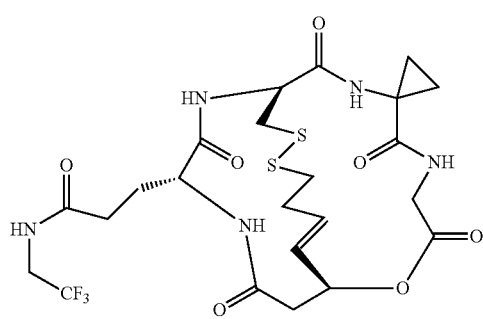
Compound XXII
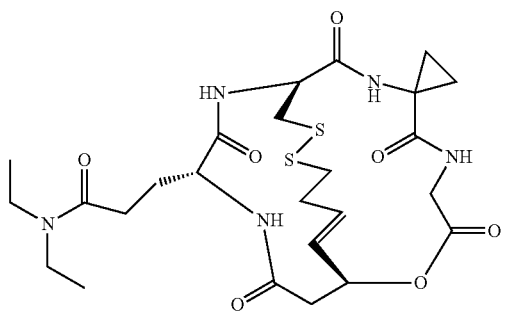
Compound XXIII
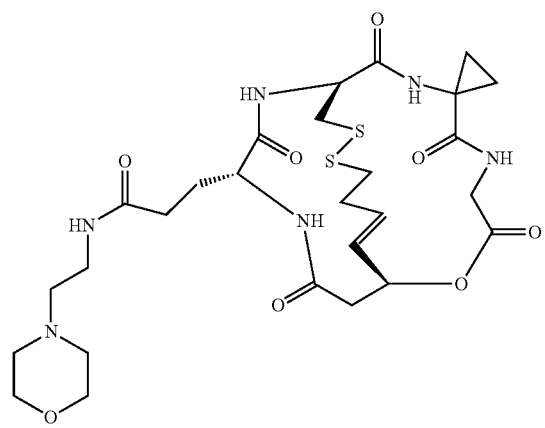

101
-continued
Compound XXIV
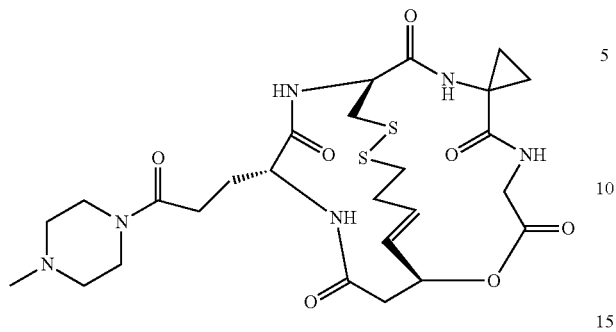
Compound XXV
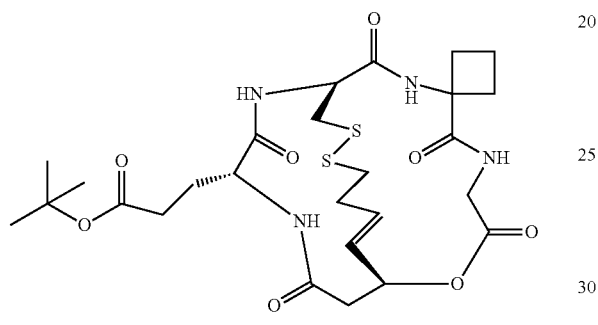
Compound XXVI
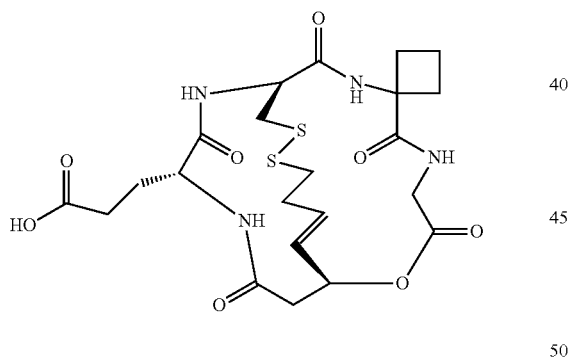
Compound XXVII
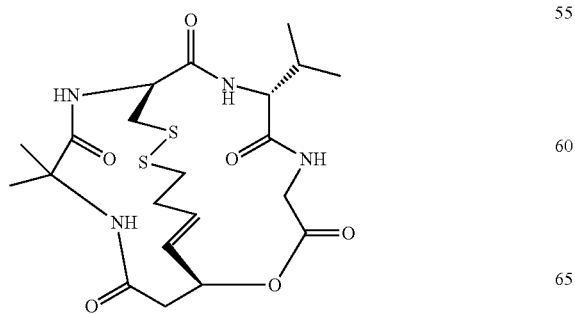
102
-continued
Compound XXIX
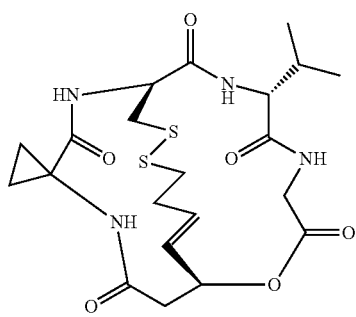
Compound XXX
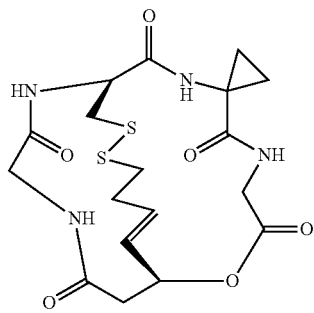
Compound XXXI
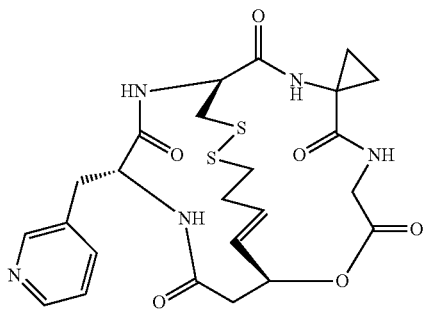
Compound XXXII
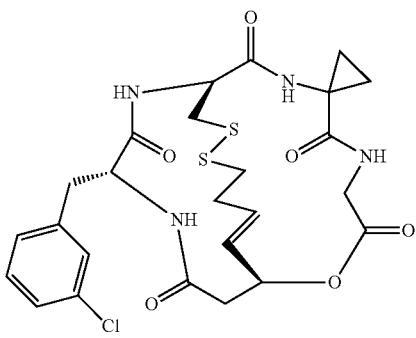

Compound XXXIII

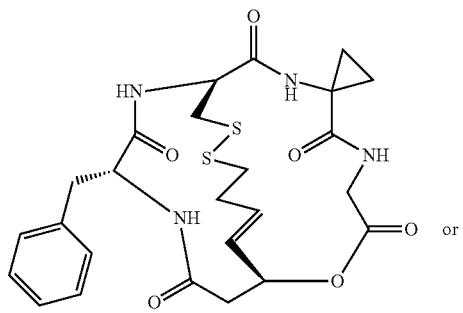

or

Compound XXXIV

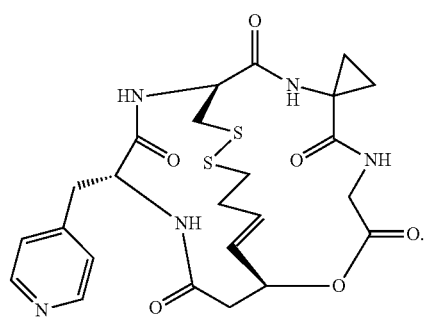

7. The compound according to claim 1, wherein X is —CH(OPr₃)—.

8. The compound according to claim 7, which has one of the Structures shown below:

Compound XI

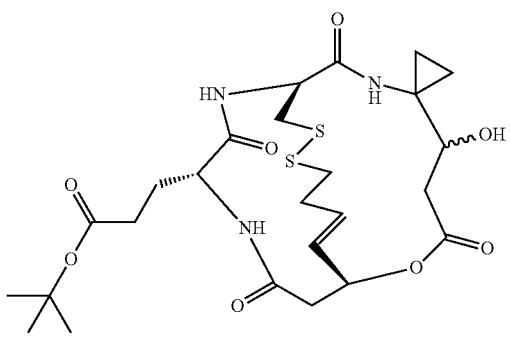

Compound XII

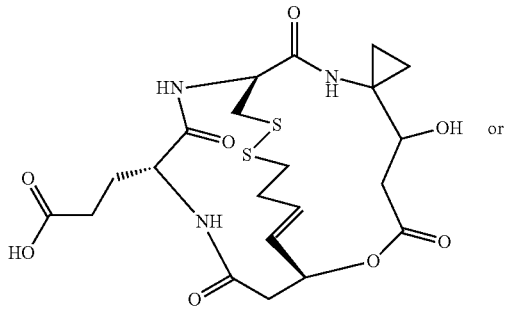

or

Compound XIII

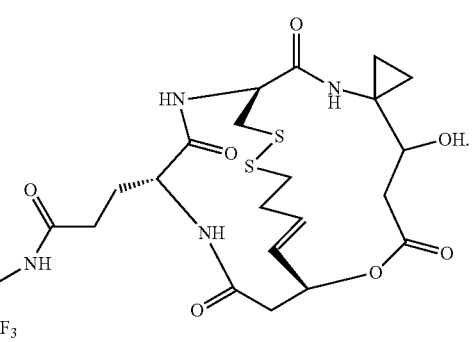

9. A method for the treatment of a condition mediated by histone deacetylate (HDAC), wherein the condition is selected from the group consisting of chronic lymphocytic leukemia, breast cancer, prostate cancer, ovarian cancer, mesothelioma, T-cell lymphoma, cardiac hypertrophy, chronic heart failure, or a skin inflammatory condition, wherein the method comprises administering, to a subject in need of such treatment, a compound of claim 1.

10. A method for accelerating wound healing, protecting hair follicles, or for providing an immunosuppressant wherein said method comprises administering to a subject a compound of claim 1.

11. A pharmaceutical composition comprising a compound according to claim 1 and a pharmaceutically acceptable carrier or diluent.

12. The composition according to claim 11, which is in a form suitable for oral, rectal, parenteral, intranasal or transdermal administration or administration by inhalation or by suppository.

13. The composition according to claim 12, which is in the form of granules, a tablet, a capsule, a troche, a lozenge, an aqueous or oily suspension, or a dispersible powder.

14. A product containing (a) a compound according to claim 1, and (b) another inhibitor of HDAC.

15. A product containing (a) a compound according to claim 1, and (b) a chemotherapeutic or antineoplastic agent.

* * * * *

UNITED STATES PATENT AND TRADEMARK OFFICE
CERTIFICATE OF CORRECTION

PATENT NO.         : 8,614,193 B2                                                          Page 1 of 1
APPLICATION NO.    : 12/991491
DATED              : December 24, 2013
INVENTOR(S)        : Shuttleworth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this
Twenty-second Day of September, 2015

Michelle K. Lee
*Director of the United States Patent and Trademark Office*